(12) United States Patent
Horan et al.

(10) Patent No.: US 9,833,304 B2
(45) Date of Patent: Dec. 5, 2017

(54) VASCULAR FILTER DEVICE

(75) Inventors: Steven Horan, Knocknacarra (IE); Paul Gilson, Moycullen (IE); Karl Keating, Oughterard (IE); Jerome Henry, Castlebar (IE); Jacqueline O'Gorman, Cratloe (IE); Ronan O'Connor, Claregalway (IE); Shane Molloy, Corrandulla (IE)

(73) Assignee: Novate Medical Limited, Dublin (IE)

( * ) Notice: Subject to any disclaimer, the term of this patent is extended or adjusted under 35 U.S.C. 154(b) by 680 days.

(21) Appl. No.: 12/688,616

(22) Filed: Jan. 15, 2010

(65) Prior Publication Data
US 2010/0185230 A1  Jul. 22, 2010

Related U.S. Application Data

(60) Provisional application No. 61/145,382, filed on Jan. 16, 2009, provisional application No. 61/145,303, filed on Jan. 16, 2009.

(51) Int. Cl.
*A61F 2/01* (2006.01)

(52) U.S. Cl.
CPC .......... *A61F 2/01* (2013.01); *A61F 2002/016* (2013.01); *A61F 2210/0004* (2013.01);
(Continued)

(58) Field of Classification Search
CPC ...... A61F 2/01; A61F 2/013; A61F 2002/016; A61F 2210/0004; A61F 2230/0067; A61F 2250/0004; A61F 2250/0006; A61F 2250/008; A61F 2250/0031; A61F 2250/0059; A61F 2250/006; A61F 2/82;
(Continued)

(56) References Cited

U.S. PATENT DOCUMENTS 4,727,873 A * 3/1988 Mobin-Uddin .............. 606/200
4,832,055 A * 5/1989 Palestrant .................... 128/899
(Continued)

FOREIGN PATENT DOCUMENTS

CN         2635045 Y      8/2004
CN      201123855 Y     10/2008
(Continued)

OTHER PUBLICATIONS

International Search Report and Written Opinion for PCT/IE2010/000002 dated Apr. 28, 2010.
U.S. Appl. No. 12/688,173, filed Jan. 15, 2010 (72 pages).

*Primary Examiner* — Anh Dang
*Assistant Examiner* — Erin Colello
(74) *Attorney, Agent, or Firm* — Bookoff McAndrews, PLLC

(57) ABSTRACT

A vascular filter device comprises a support; and a filter comprising one or more filter elements configured to capture thrombus passing through a blood vessel. A holder holds the filter in a closed filtering state and releases to convert the filter to an open state after a period of time. The filter is adapted to retain thrombus after said conversion. In one case the filter elements are arranged to remain in a closed state after release by the holder, because they are blocked by a retained clot from opening fully, and the filter elements are biased to the open state with a bias level which is counter balanced by force exerted by a retained clot under action of blood flow.

3 Claims, 85 Drawing Sheets

(52) U.S. Cl.
CPC ... *A61F 2230/005* (2013.01); *A61F 2230/006* (2013.01); *A61F 2230/0058* (2013.01); *A61F 2230/0067* (2013.01); *A61F 2230/0078* (2013.01); *A61F 2250/0059* (2013.01)

(58) Field of Classification Search
CPC ............ A61F 2250/0071; A61F 2/2418; A61F 2002/068; A61F 2/86; A61F 2230/005; A61F 2230/0058; A61F 2230/006; A61F 2230/0078; A61B 17/221; A61B 2017/2215; A61B 2017/2217; A61B 2019/307
USPC ........ 606/200, 113, 114, 127, 128; 623/1.11, 623/1.12, 1.24
See application file for complete search history.

(56) References Cited

U.S. PATENT DOCUMENTS

| | | | |
|---|---|---|---|
| 5,344,427 A | 9/1994 | Cottenceau et al. | |
| 5,370,657 A * | 12/1994 | Irie | 606/200 |
| 5,375,612 A * | 12/1994 | Cottenceau et al. | 128/899 |
| 5,383,887 A * | 1/1995 | Nadal | 606/200 |
| 5,626,605 A * | 5/1997 | Irie et al. | 623/1.1 |
| 5,634,942 A * | 6/1997 | Chevillon et al. | 623/1.1 |
| 5,709,704 A * | 1/1998 | Nott et al. | 606/200 |
| 5,725,550 A | 3/1998 | Nadal | |
| 5,800,525 A | 9/1998 | Bachinski et al. | |
| 5,810,874 A * | 9/1998 | Lefebvre | 606/200 |
| 5,853,420 A | 12/1998 | Chevillon et al. | |
| 5,968,071 A * | 10/1999 | Chevillon et al. | 606/200 |
| 6,080,178 A * | 6/2000 | Meglin | 606/200 |
| 6,193,739 B1 | 2/2001 | Chevillon et al. | |
| 6,214,025 B1 * | 4/2001 | Thistle et al. | 606/200 |
| 6,241,746 B1 | 6/2001 | Bosma et al. | |
| 6,248,128 B1 | 6/2001 | Berry et al. | |
| 6,267,776 B1 * | 7/2001 | O'Connell | 606/200 |
| 6,267,777 B1 * | 7/2001 | Bosma et al. | 606/200 |
| 6,312,461 B1 | 11/2001 | Unsworth et al. | |
| 6,383,206 B1 * | 5/2002 | Gillick et al. | 606/200 |
| 6,436,120 B1 * | 8/2002 | Meglin | 606/200 |
| 6,482,227 B1 | 11/2002 | Solovay | |
| 6,517,559 B1 * | 2/2003 | O'Connell | 606/158 |
| 6,527,962 B1 | 3/2003 | Nadal | |
| 6,582,447 B1 * | 6/2003 | Patel et al. | 606/200 |
| 6,605,111 B2 | 8/2003 | Bose et al. | |
| 6,652,558 B2 * | 11/2003 | Patel et al. | 606/200 |
| 6,666,882 B1 | 12/2003 | Bose et al. | |
| 6,669,721 B1 | 12/2003 | Bose et al. | |
| 6,800,080 B1 * | 10/2004 | Bates | 606/127 |
| 6,852,076 B2 | 2/2005 | Nikolic et al. | |
| 6,881,218 B2 * | 4/2005 | Beyer et al. | 606/200 |
| 6,918,921 B2 * | 7/2005 | Brady et al. | 606/200 |
| 6,932,832 B2 | 8/2005 | Patel et al. | |
| 6,966,923 B2 | 11/2005 | Gittings | |
| 6,972,025 B2 | 12/2005 | WasDyke | |
| 7,001,424 B2 | 2/2006 | Patel et al. | |
| 7,094,248 B2 | 8/2006 | Bachinski et al. | |
| 7,261,731 B2 | 8/2007 | Patel et al. | |
| 7,279,007 B2 | 10/2007 | Nikolic et al. | |
| 7,316,692 B2 * | 1/2008 | Huffmaster | 606/127 |
| 7,329,269 B2 * | 2/2008 | Shapiro et al. | 606/200 |
| 7,534,251 B2 | 5/2009 | WasDyke | |
| 8,025,675 B2 * | 9/2011 | Shirley | A61F 2/01 606/200 |
| 8,734,481 B2 * | 5/2014 | O'Connell | A61F 2/01 606/202 |
| 2001/0044652 A1 | 11/2001 | Moore | |
| 2002/0116024 A1 * | 8/2002 | Goldberg et al. | 606/200 |
| 2003/0120303 A1 | 6/2003 | Boyle et al. | |
| 2003/0176888 A1 * | 9/2003 | O'Connell | 606/200 |
| 2003/0208227 A1 * | 11/2003 | Thomas | 606/200 |
| 2003/0208253 A1 * | 11/2003 | Beyer et al. | 623/1.1 |
| 2004/0019374 A1 * | 1/2004 | Hojeibane et al. | 623/1.13 |
| 2004/0059373 A1 * | 3/2004 | Shapiro et al. | 606/200 |
| 2004/0220611 A1 | 11/2004 | Ogle | |
| 2005/0033314 A1 * | 2/2005 | Sakurai et al. | 606/127 |
| 2005/0096735 A1 * | 5/2005 | Hojeibane et al. | 623/1.24 |
| 2005/0107822 A1 | 5/2005 | WasDyke | |
| 2005/0165442 A1 * | 7/2005 | Thinnes et al. | 606/200 |
| 2005/0209632 A1 * | 9/2005 | Wallace | 606/200 |
| 2005/0222604 A1 | 10/2005 | Schaeffer | |
| 2005/0234504 A1 | 10/2005 | WasDyke | |
| 2006/0025852 A1 | 2/2006 | Armstrong et al. | |
| 2006/0122522 A1 * | 6/2006 | Chavan et al. | 600/505 |
| 2006/0241675 A1 * | 10/2006 | Johnson et al. | 606/200 |
| 2007/0032816 A1 | 2/2007 | O'Connell et al. | |
| 2007/0112372 A1 * | 5/2007 | Sosnowski et al. | 606/200 |
| 2007/0203571 A1 | 8/2007 | Kaplan et al. | |
| 2008/0027481 A1 * | 1/2008 | Gilson | A61F 2/01 606/200 |
| 2008/0188887 A1 * | 8/2008 | Batiste | 606/200 |
| 2008/0208245 A1 | 8/2008 | Hoffman | |
| 2010/0185227 A1 | 7/2010 | Horan et al. | |
| 2010/0185229 A1 | 7/2010 | Horan et al. | |
| 2010/0204772 A1 * | 8/2010 | Holzer et al. | 623/1.11 |

FOREIGN PATENT DOCUMENTS

| | | |
|---|---|---|
| DE | 40 30 998 A1 | 4/1991 |
| DE | 102008031299 A1 | 1/2010 |
| EP | 0 565 395 A1 | 10/1993 |
| EP | 0 598 635 A1 | 5/1994 |
| EP | 0 655 228 A1 | 5/1995 |
| EP | 0678284 A1 | 10/1995 |
| EP | 0 582 493 A1 | 7/1997 |
| EP | 0 935 975 A1 | 8/1999 |
| EP | 0 605 276 A1 | 2/2000 |
| EP | 1 103 233 A1 | 5/2001 |
| EP | 1 258 228 A1 | 11/2002 |
| EP | 0 759 287 A1 | 2/2003 |
| EP | 0 737 451 A1 | 9/2003 |
| EP | 1 616 530 A1 | 1/2006 |
| FR | 2 718 950 | 10/1995 |
| FR | 2 764 503 | 12/1998 |
| FR | 2 814 670 | 4/2002 |
| WO | WO 00/56390 | 9/2000 |
| WO | WO 00/66031 | 11/2000 |
| WO | WO 01/62184 A2 | 8/2001 |
| WO | WO 02/22048 A2 | 3/2002 |
| WO | WO 03092537 A2 * | 11/2003 |
| WO | WO 2006/020425 A1 | 2/2006 |
| WO | WO 2006/074163 A2 | 7/2006 |
| WO | WO 2006/107939 A1 | 10/2006 |
| WO | WO 2006/116636 A1 | 11/2006 |
| WO | WO 2007079407 A2 * | 7/2007 ............ A61F 2/01 |
| WO | WO 2008/010197 A2 | 1/2008 |

* cited by examiner

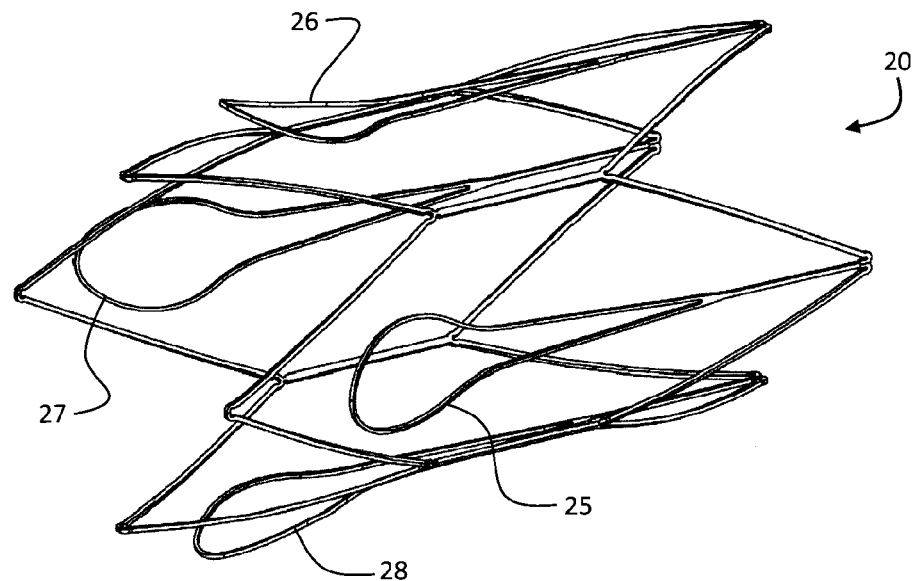
Fig.5
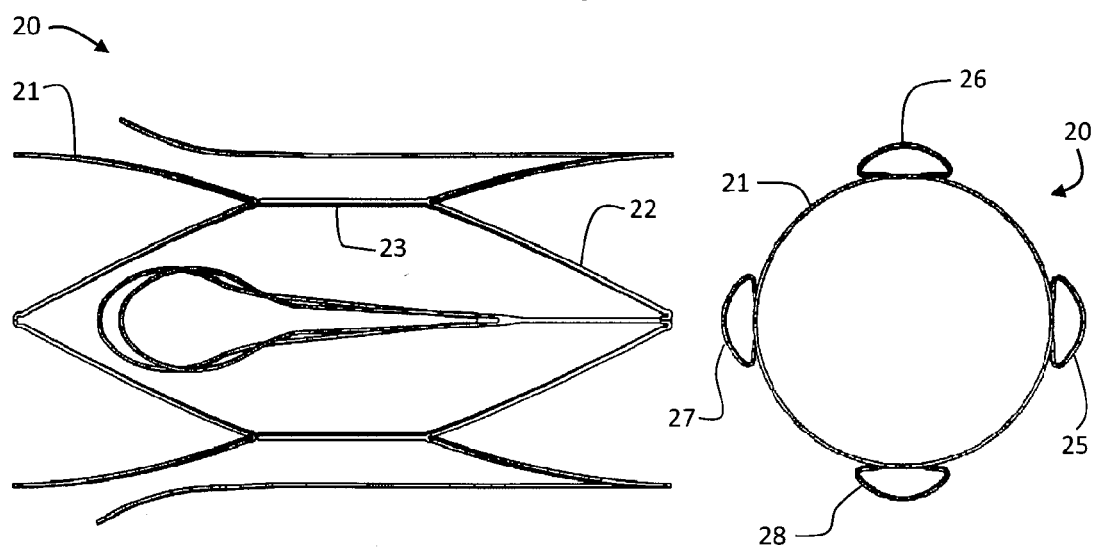
Fig.6
Fig.7

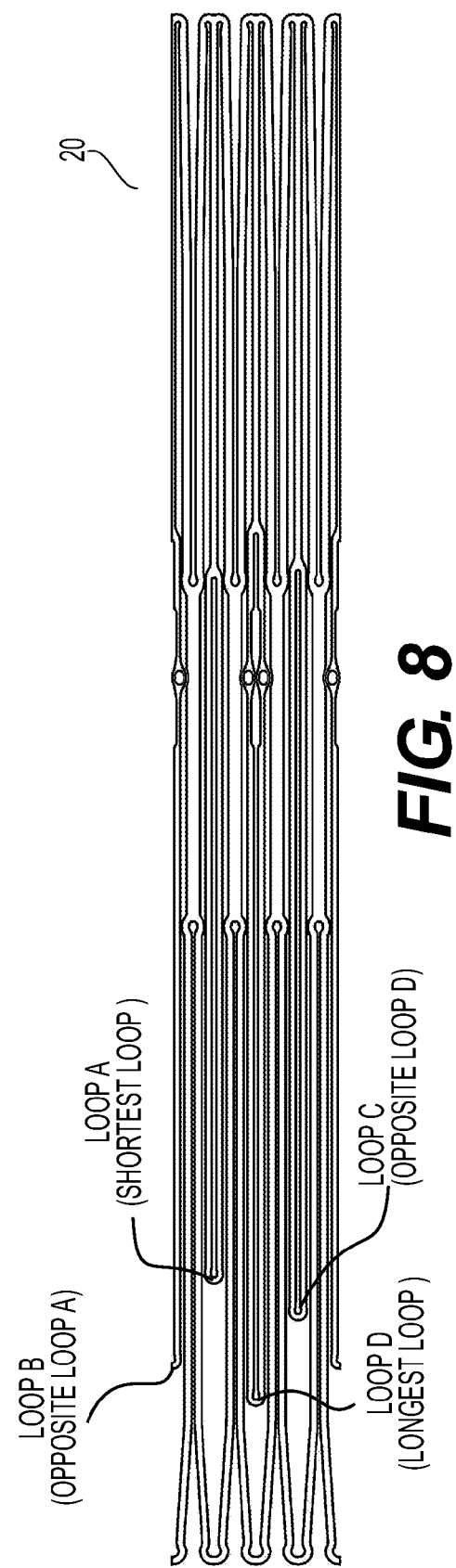

Retainer

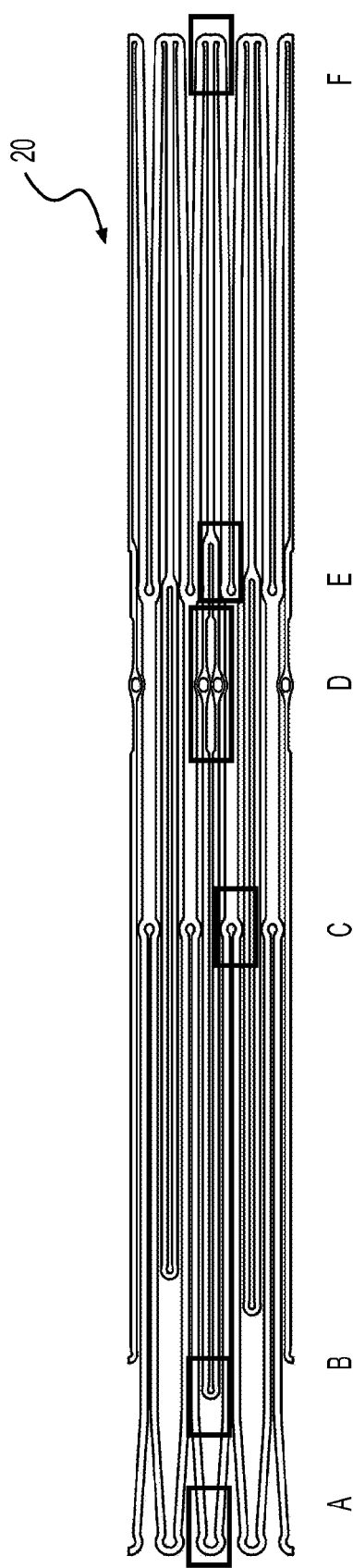
FIG. 19
FIG. 20 — DETAIL A
FIG. 21 — DETAIL B

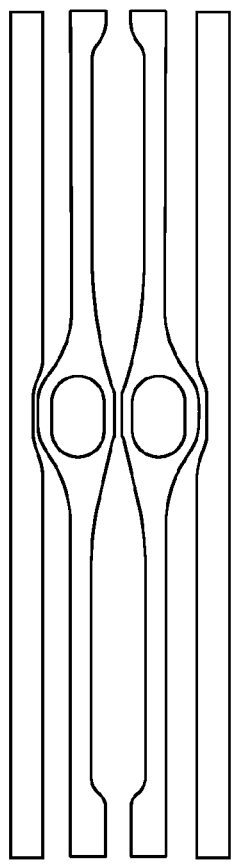
FIG. 22 DETAIL C
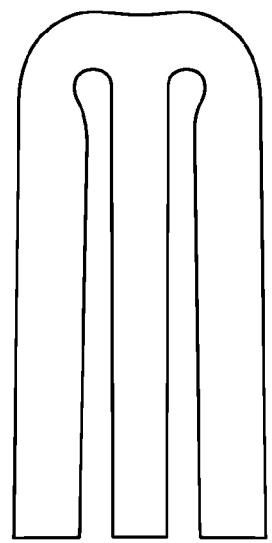
FIG. 23 DETAIL D
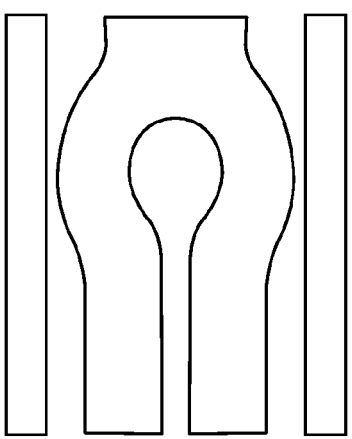
FIG. 24 DETAIL E
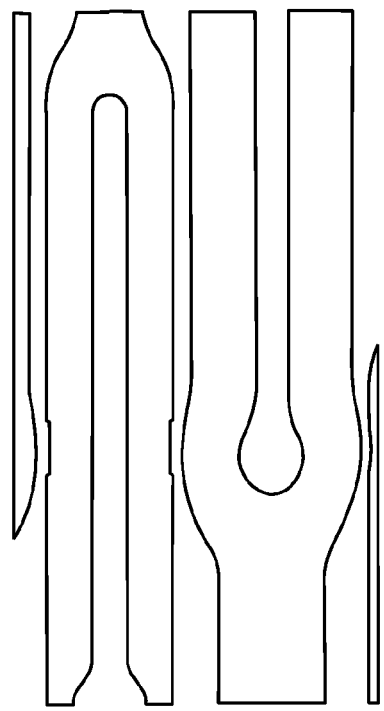
FIG. 25 DETAIL F

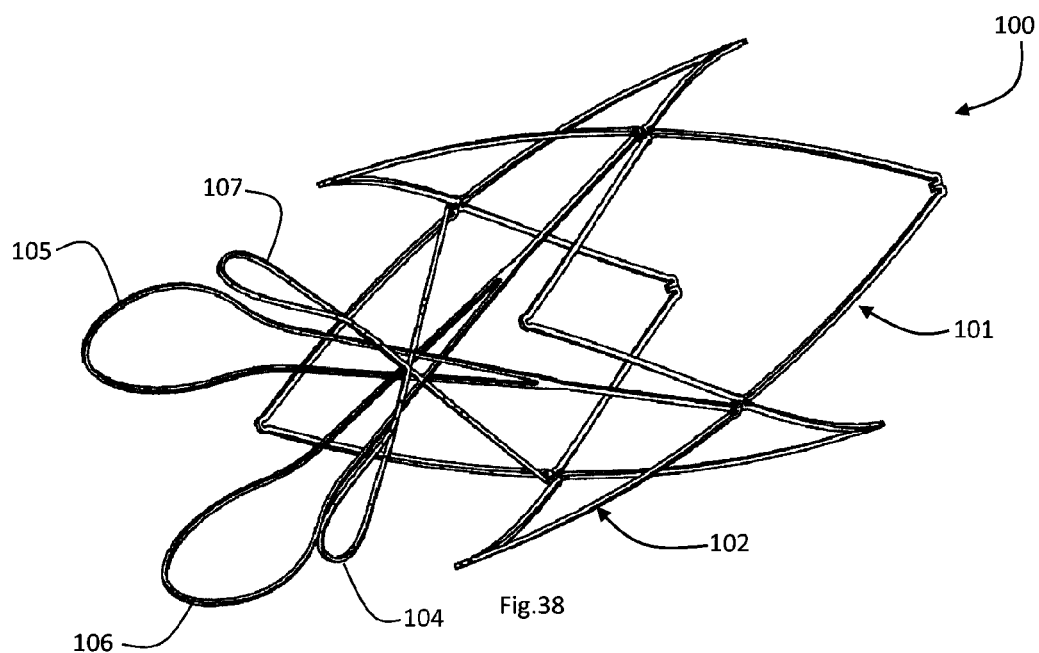
Fig.38
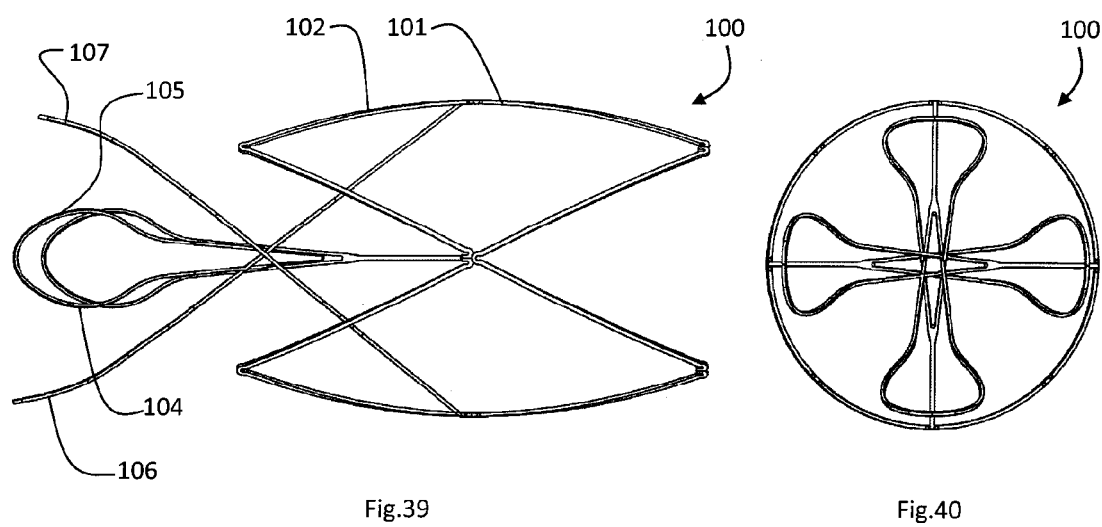
Fig.39
Fig.40

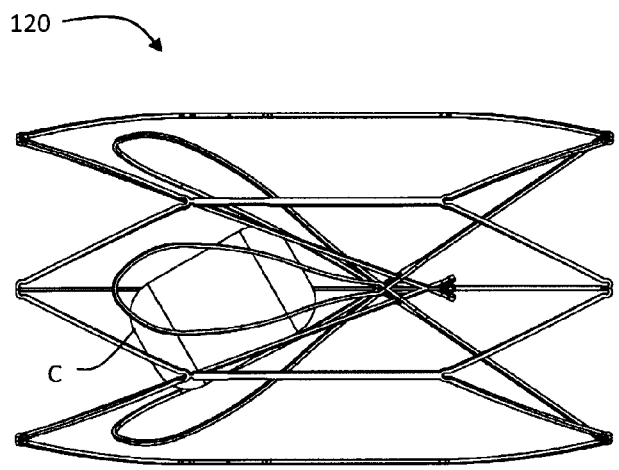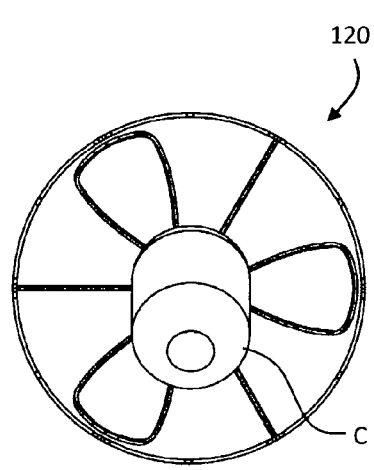
Fig.51　　　　　　　　　　　　Fig.52
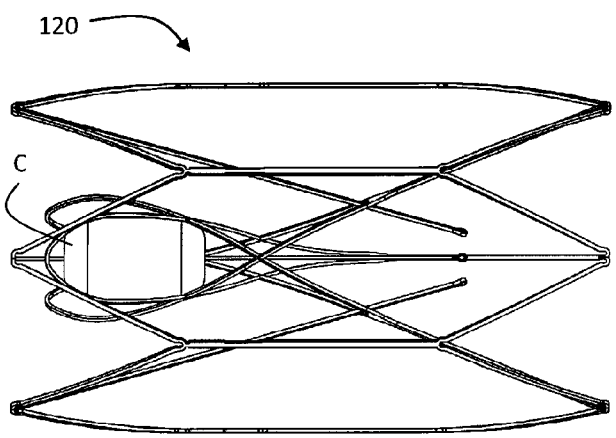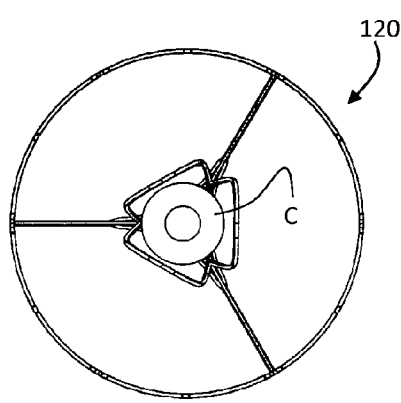
Fig.53　　　　　　　　　　　　Fig.54

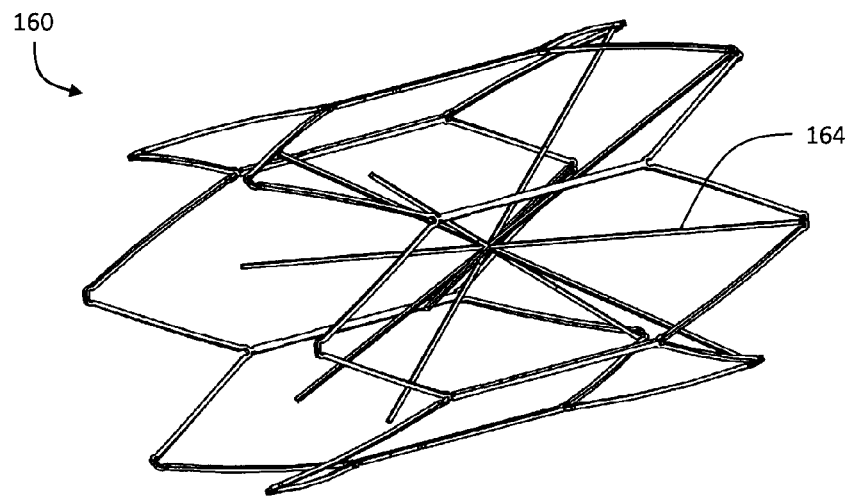
Fig.63
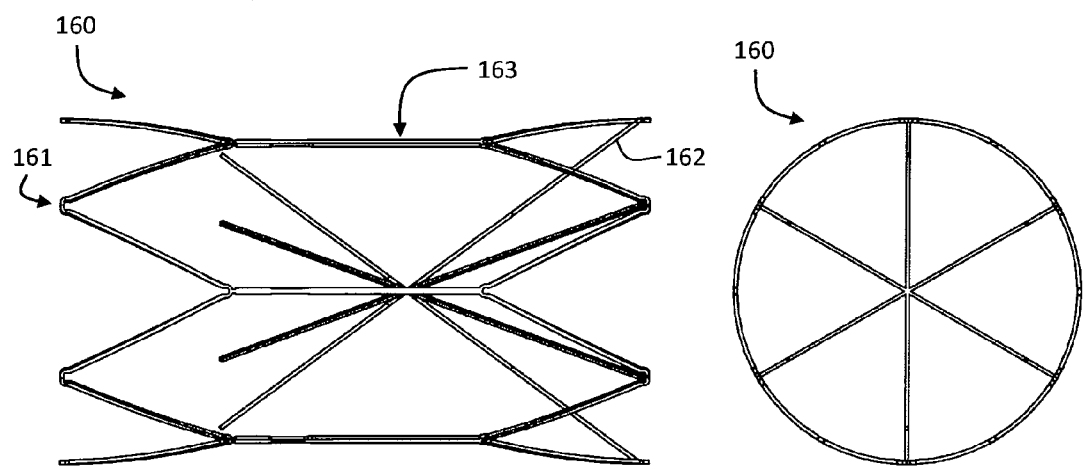
Fig.64
Fig.65
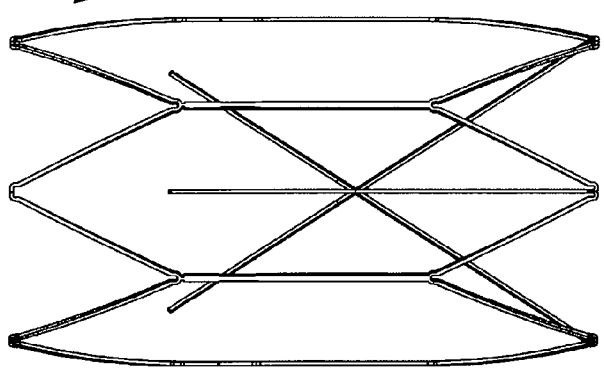
Fig.66

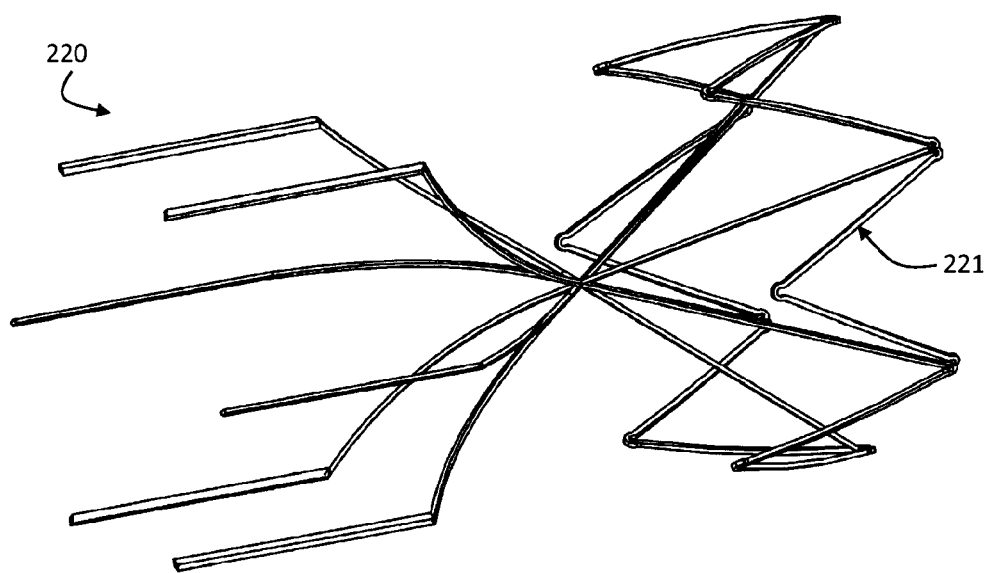
Fig.83
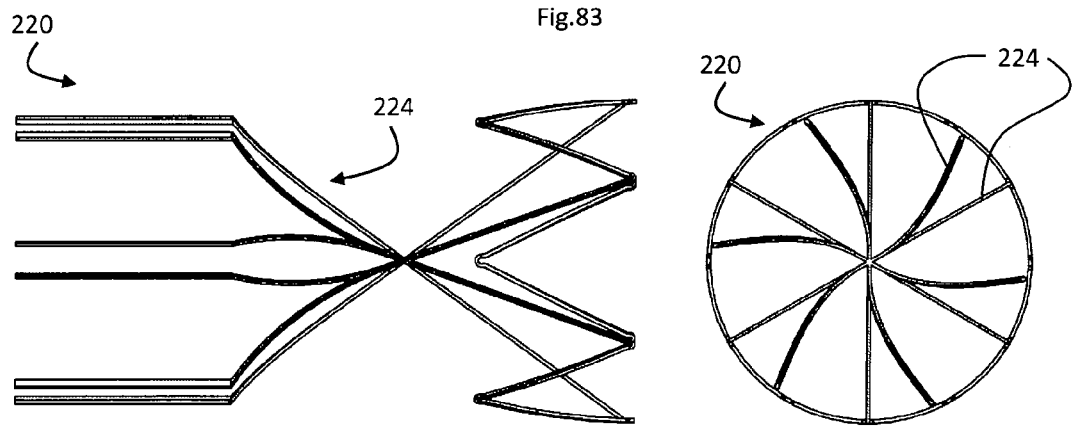
Fig.84
Fig.85
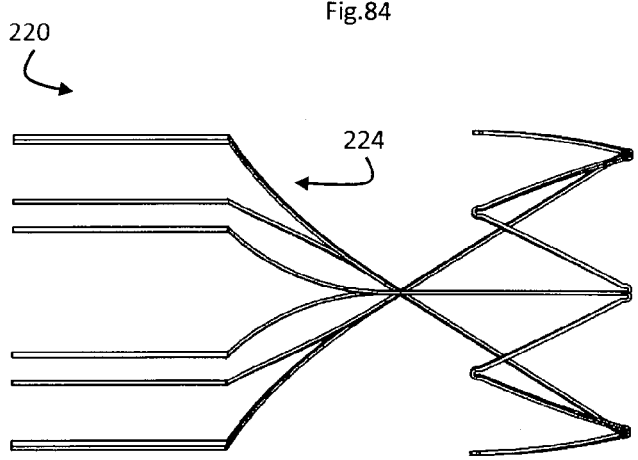
Fig.86

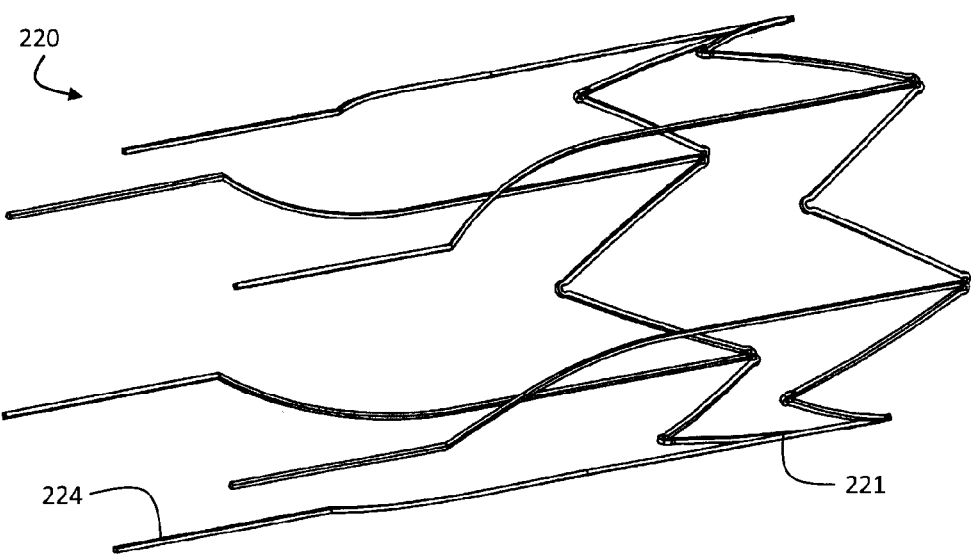
Fig.87
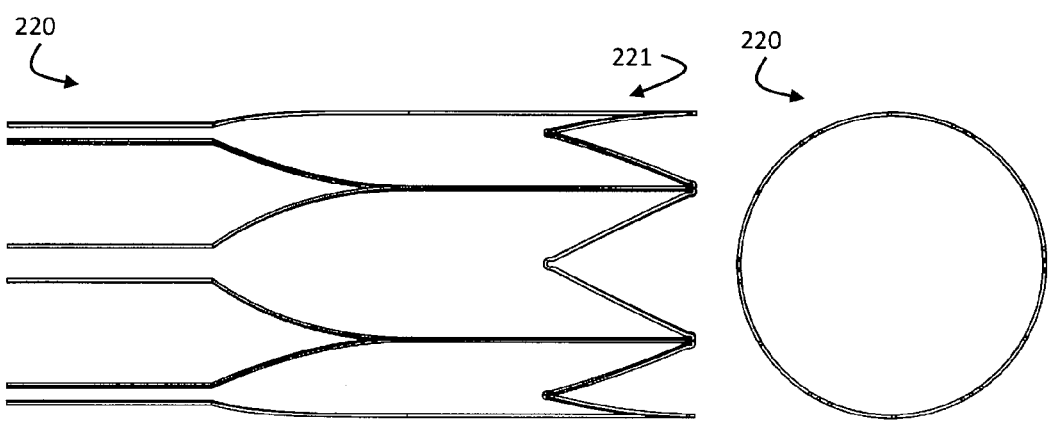
Fig.88
Fig.89
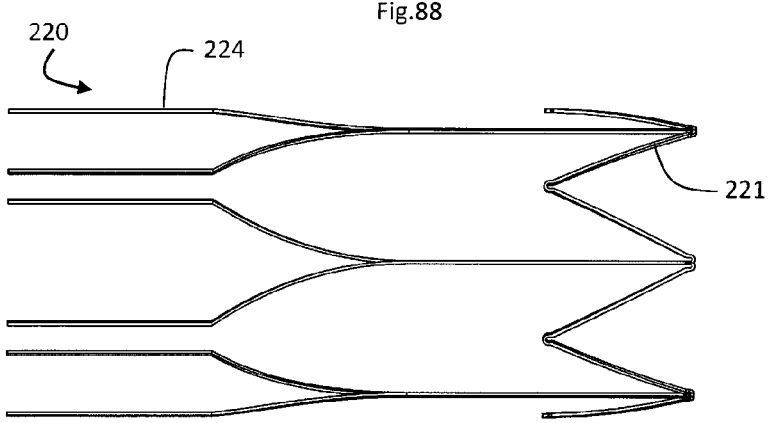
Fig.90

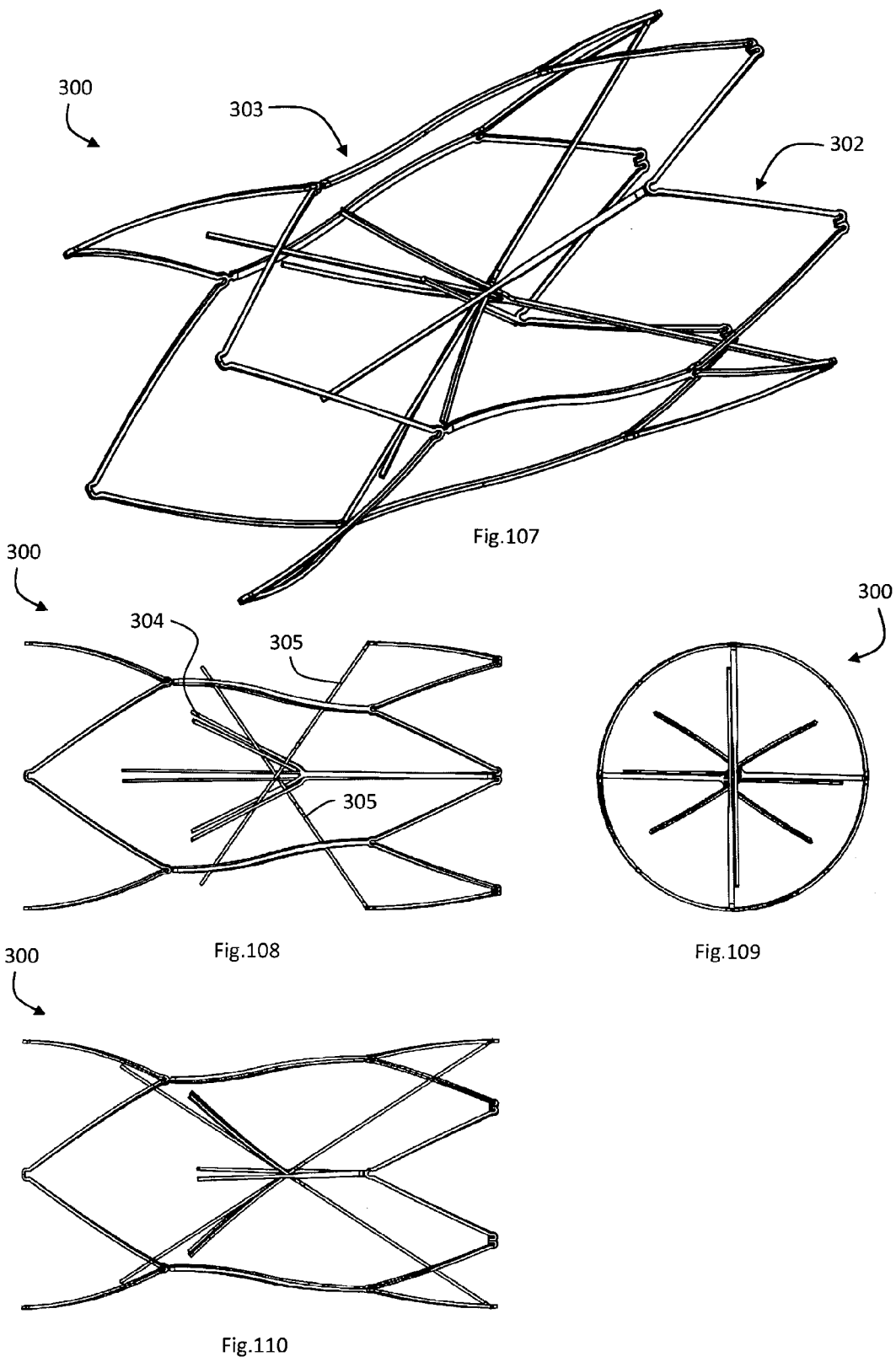

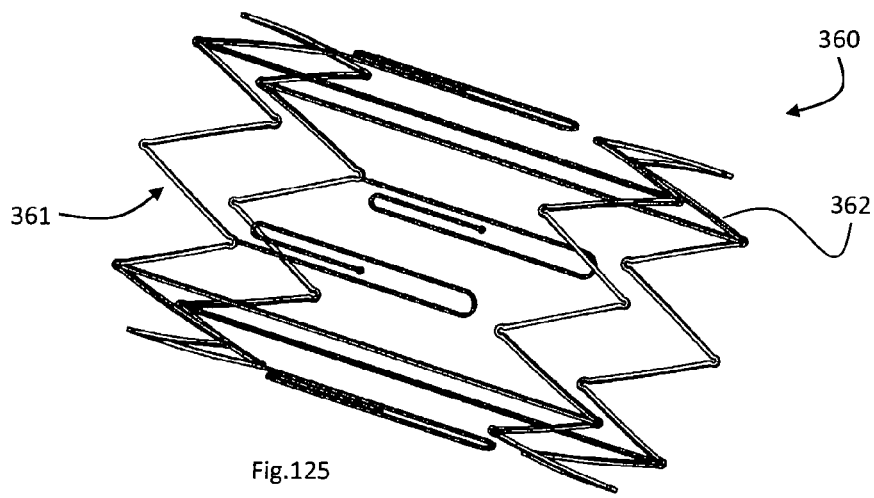
Fig.125
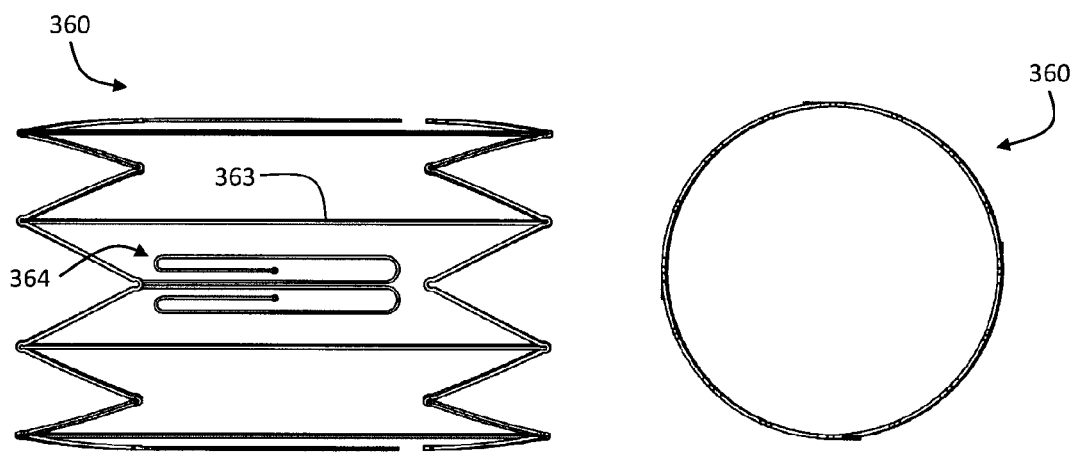
Fig.126
Fig.127
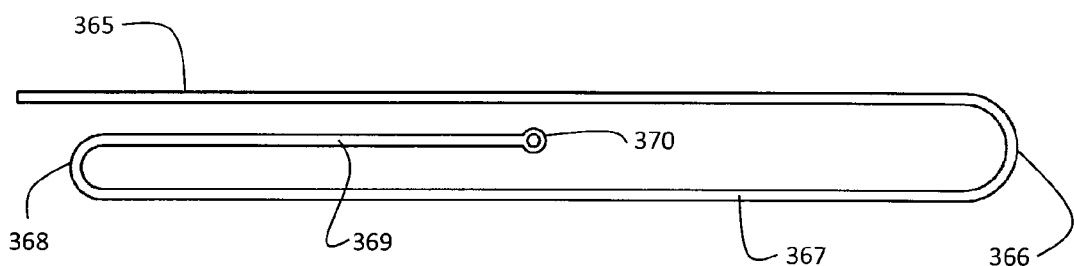
Fig.128

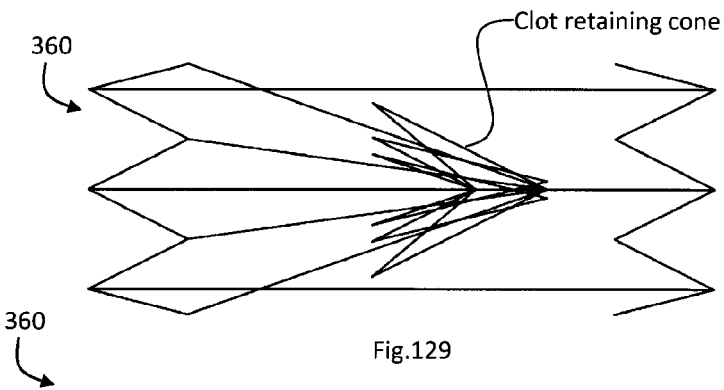
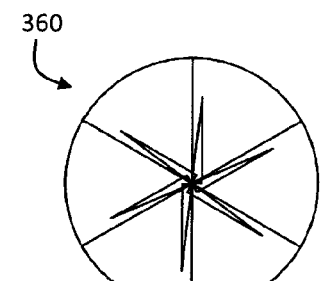
Fig.129
Fig.130
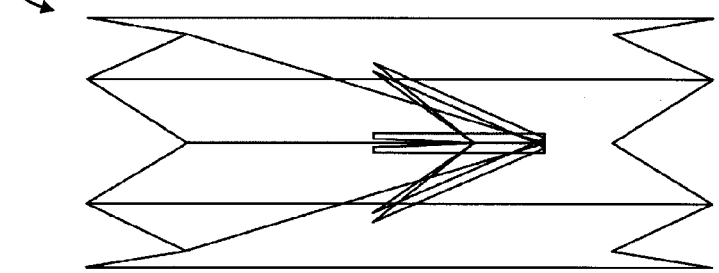
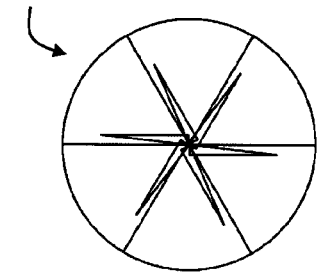
Fig.131
Fig.132
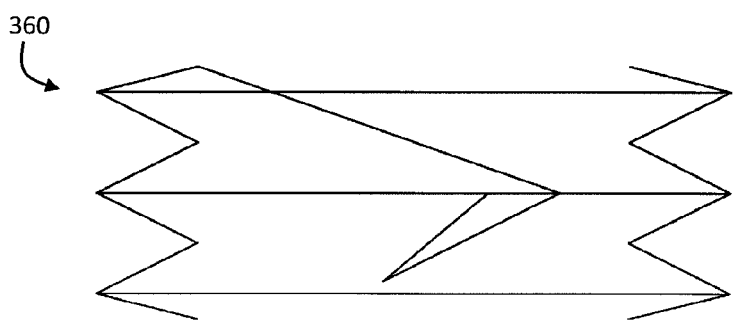
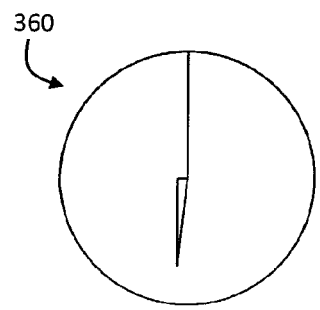
Fig.133
Fig.134
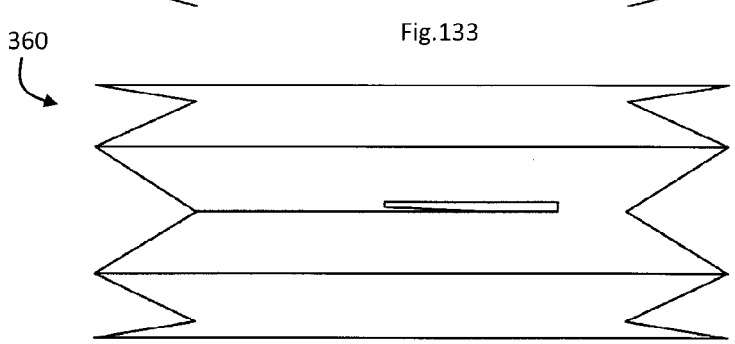
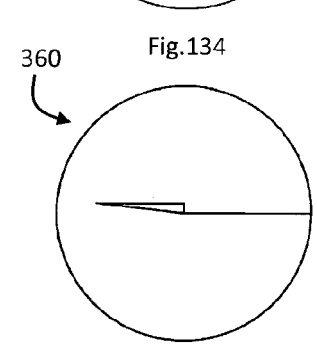
Fig.135
Fig.136

Support hoop

Inner biodegradable tie

Filter element connector

Clasps do not return to vessel wall once biodegradable tie Has released until clot is lysed

DETAIL A
SCALE 8 : 1

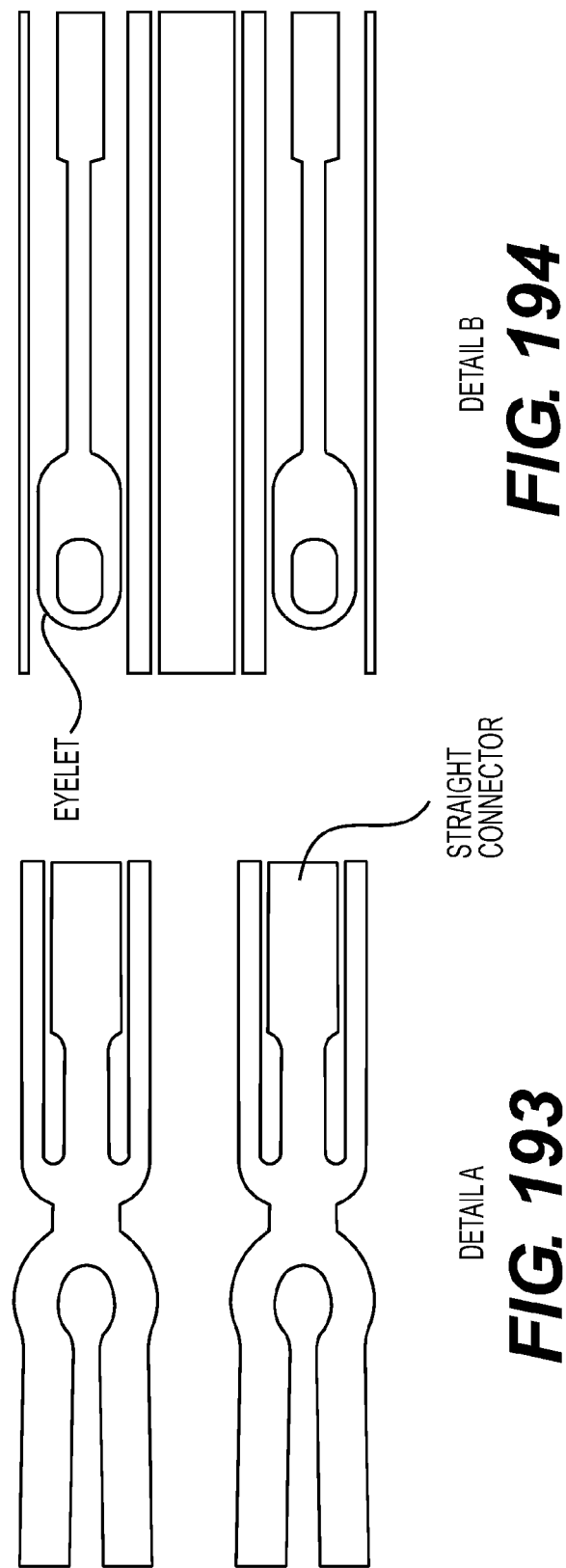

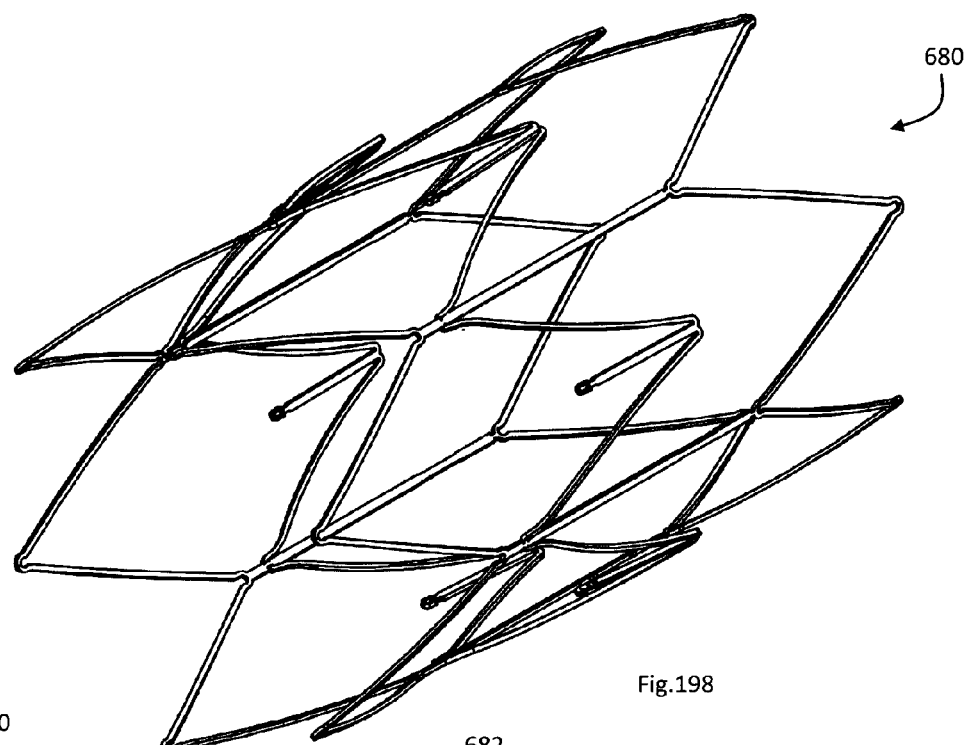
Fig.198
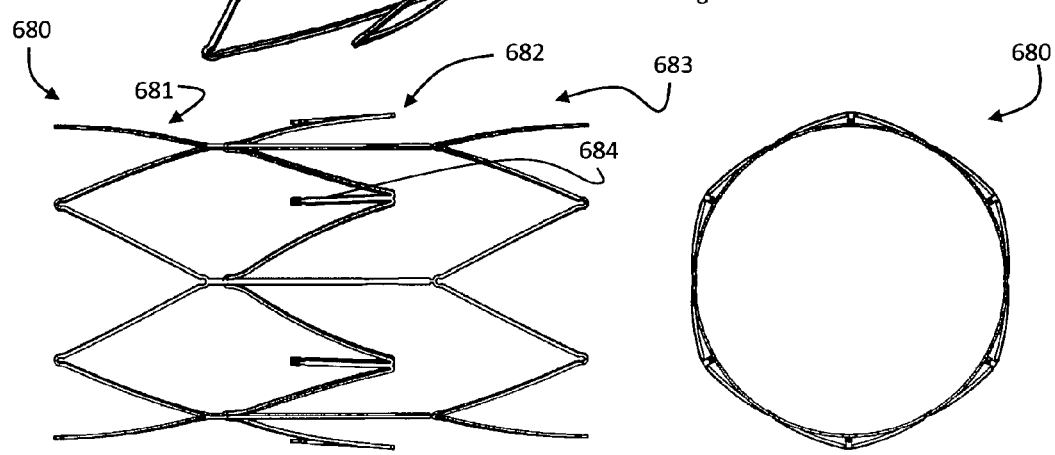
Fig.199
Fig.200
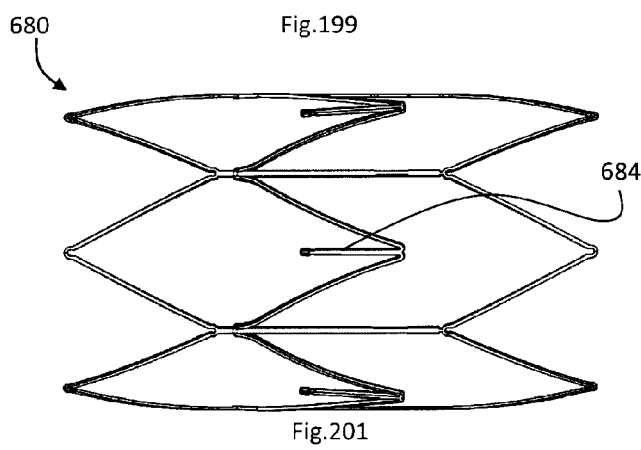
Fig.201

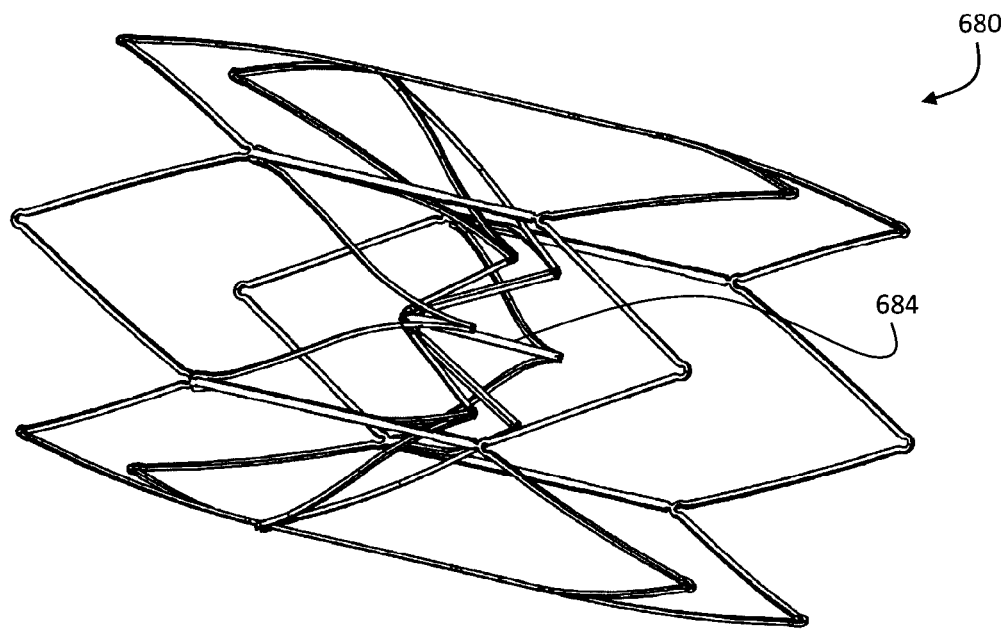
Fig.202
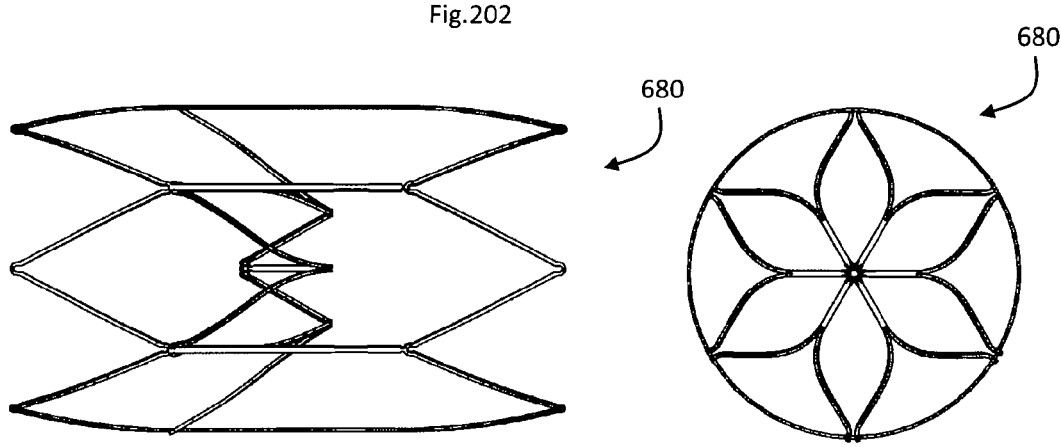
Fig.203
Fig.204
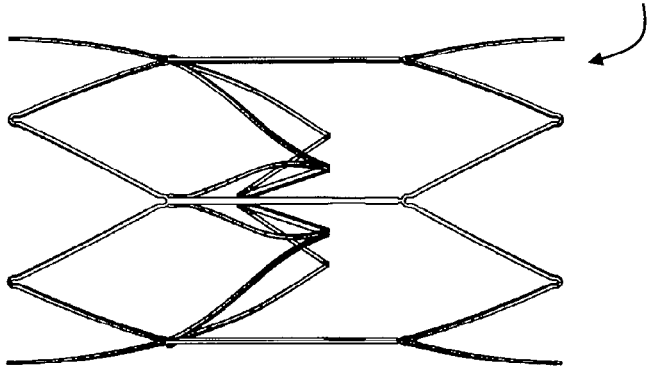
Fig.205

DETAIL A

DETAIL B

DETAIL C

DETAIL D

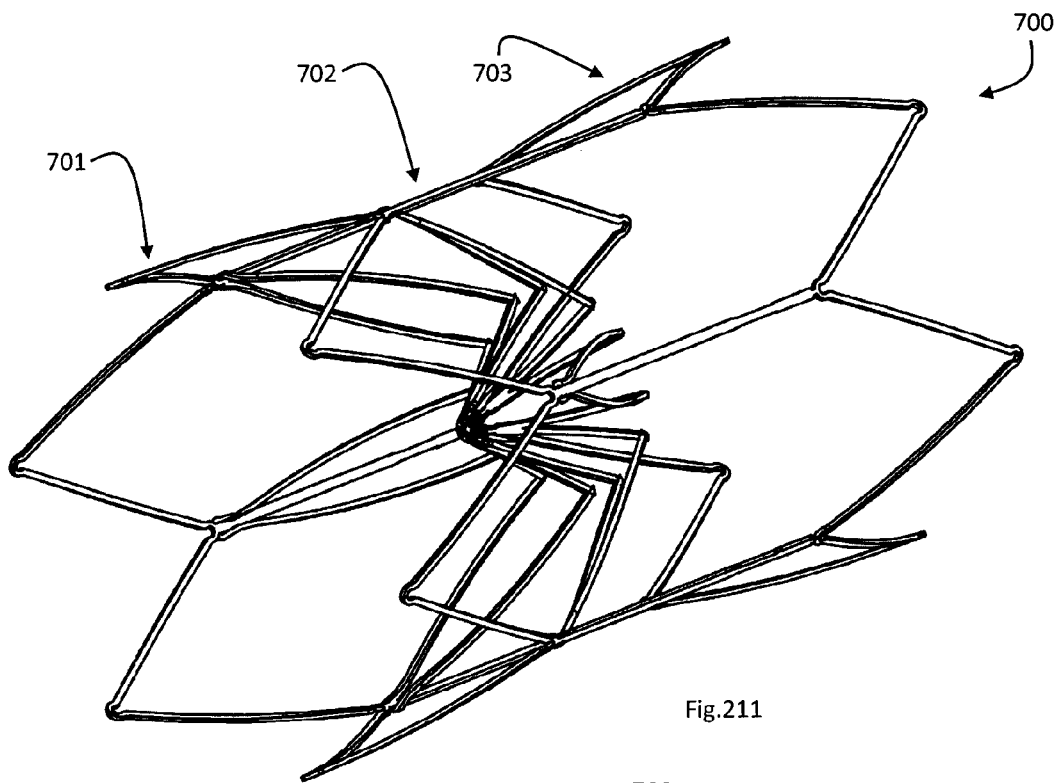
Fig.211
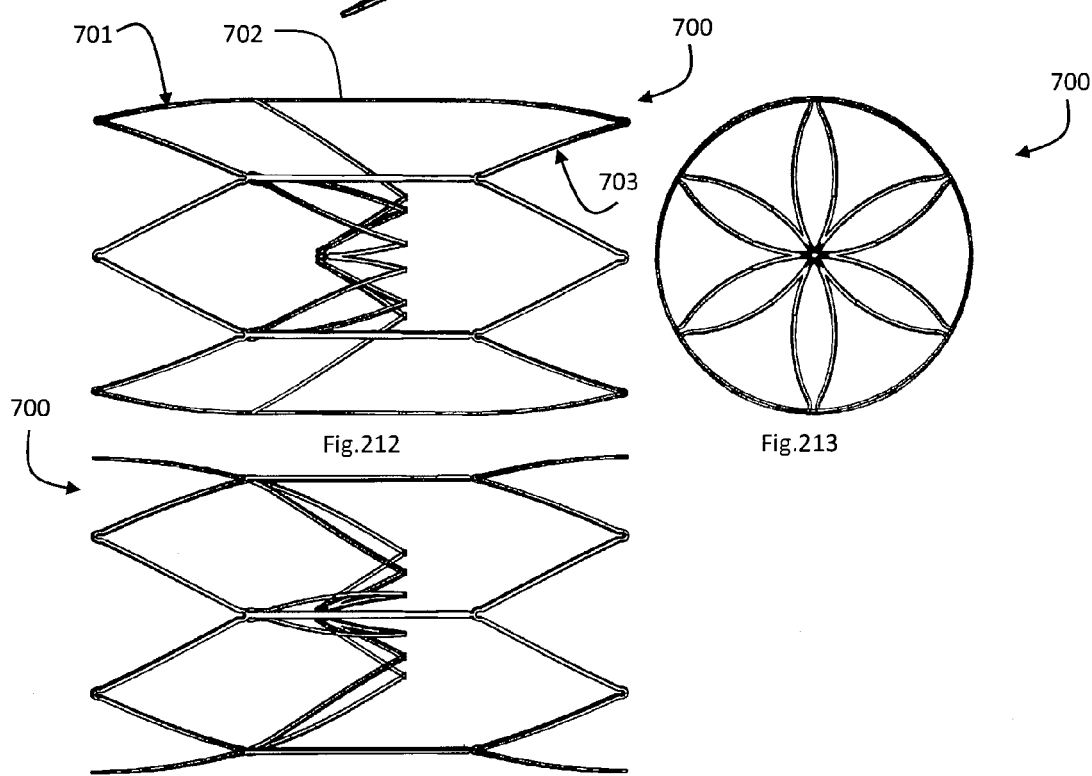
Fig.212
Fig.213
Fig.214

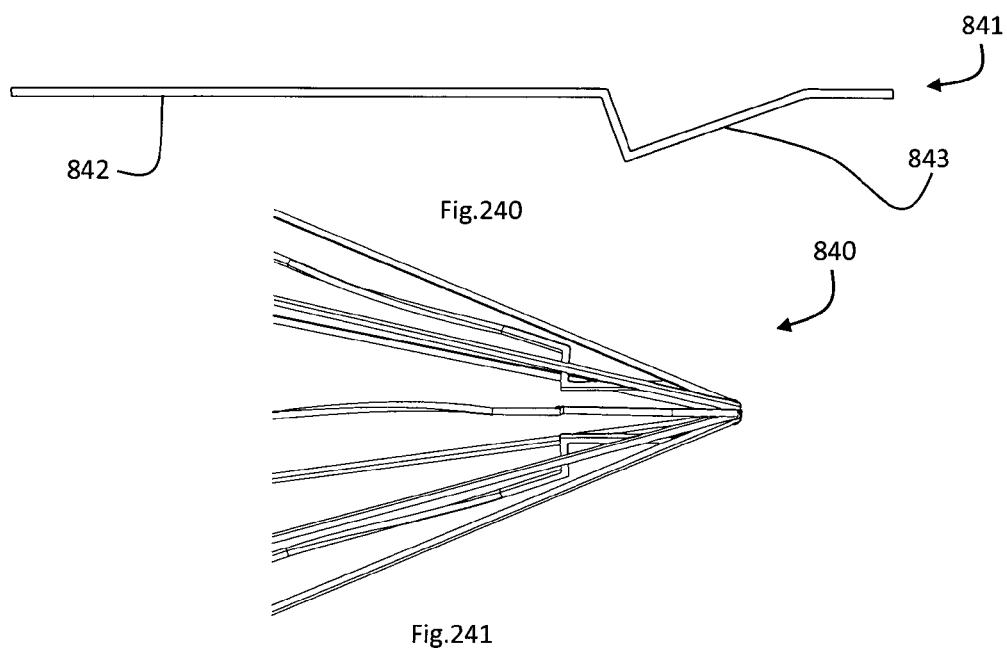
Fig.240
Fig.241
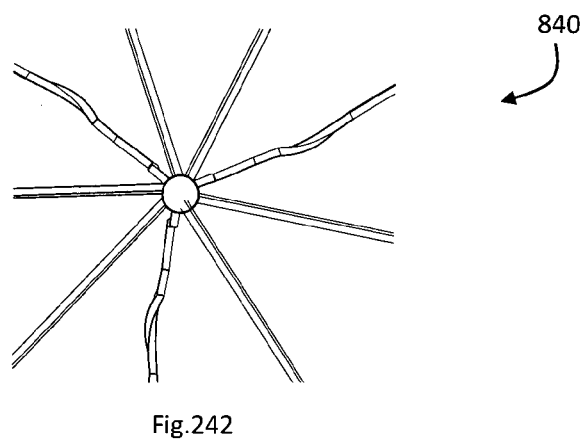
Fig.242
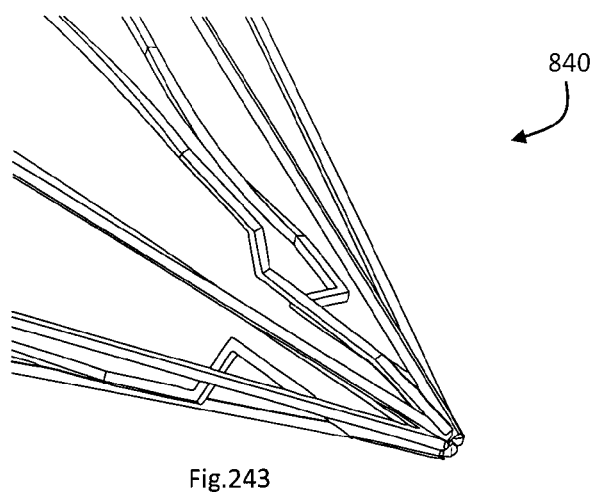
Fig.243

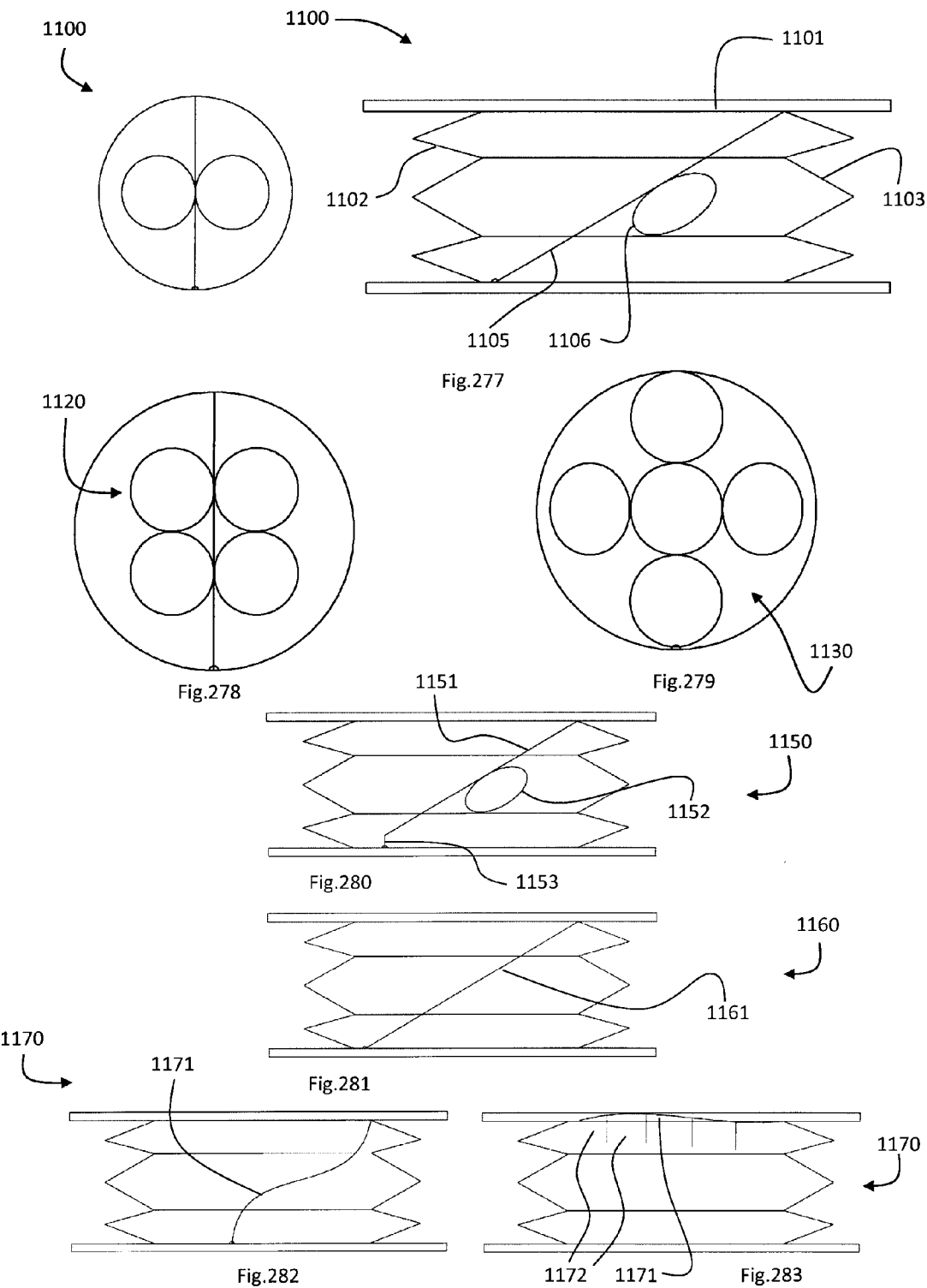

VASCULAR FILTER DEVICE

RELATED APPLICATIONS

This application claims the benefit of priority from U.S. Provisional Application No. 61/145,382 filed on Jan. 16, 2009, the entire contents of which are incorporated herein by reference. This application also claims the benefit of priority from U.S. Provisional Application No. 61/145,303 filed on Jan. 16, 2009, the entire contents of which are incorporated herein by reference.

INTRODUCTION

This invention relates to a vascular filter device.

It is known to provide a vascular filter which is supported in a blood vessel. It includes a support, which may be stent-like. Such a device is described in our prior PCT specification no. WO2008/010197. Such a device has a filter comprising a number of filter elements which are held in a closed state by a holder. The holder may be biodegradable so that the filtering takes place for a limited time period which is pre-determined, say 60-90 days. Upon expiry of this time the filter converts to an open state in which filtering ceases with unrestricted blood flow. Thereafter the device remains in situ and there is endothelial coverage of the filter elements over time.

WO02/22048 describes various filter devices, one of which (FIG. 10) has a fine mesh interconnecting the filter spokes, which are inclined so that clots are directed to the outer perimeter against the vessel wall.

A problem with many devices of the convertible type is that there is a risk that a captured clot may be released to flow beyond the device upon filter conversion. The present invention addresses this problem.

In this specification the terms "proximal" and "distal" are with reference to the direction of blood flow, the proximal parts being upstream of the distal parts.

SUMMARY OF THE INVENTION

In one aspect, the invention provides a vascular filter device comprising a support; and a filter comprising one or more filter elements, and being configured to capture thrombus passing through a blood vessel. A holder holds the filter in a closed filtering state and releases to convert the filter to an open state after a period of time. The filter is adapted to retain captured thrombus after said conversion In one embodiment, at least some of the filter elements are arranged to remain in a closed state after release by the holder, because they are blocked by a retained clot from opening fully. In one embodiment, said filter elements are biased to the open state with a bias level which is counter balanced by force exerted by a retained clot under action of blood flow.

In one embodiment, the filter elements are adapted to converge at an apex between the ends of the filter elements and in the closed state the holder retains the filter elements interconnected at the apex with proximal ends of the filter elements forming a proximal cone to capture thrombus, and the filter elements are adapted to retain a clot-retaining proximal cone shape after conversion if a clot is present at conversion.

In one embodiment, said filter elements are biased towards the open state and so are pressed against a retained clot as they attempt to move to the open state, thereby aiding clot break down. In one embodiment, at least one filter element is configured to be directed radially inwardly at a proximal end when in the closed state for improved clot retention.

In one embodiment, at least some of the filter elements are looped and inter-engage through each other. In one embodiment, at least one filter element includes a filter arm within the loop. In one embodiment, at least one filter element is splayed out at a proximal end to promote endothelial coverage when in the open state. In one embodiment, at least one filter element is connected in a cantilevered manner to the support to be biased to the open state. In one embodiment, said element is connected to a proximal end of the support by a support hoop extending distally, and is within the support hoop.

In one embodiment, at least one filter element is in the configuration of an arm. In one embodiment, the arm is curved.

In one embodiment, at least two arms are in a twisted configuration with the holder in place, and are configured to unwind upon conversion to aid clot break down. In one embodiment, at least one filter element is configured with a Y-shaped part at its proximal end. In one embodiment, at least one filter element is fork-shaped at its proximal end.

In one embodiment, the filter comprises a proximal region and a distal region, and the holder is adapted to release the proximal region upon conversion leaving the distal region to retain a clot after conversion. In one embodiment, the distal region is cone-shaped and has an apex facing the proximal direction. In one embodiment, the holder is adapted to release the distal region after a time and the filter elements are biased radially outwardly to press a clot against a vessel wall upon release.

In one embodiment, the proximal region is coarser than the distal region. In one embodiment, the regions are formed by two cones facing in the same direction, their apexes facing distally. In one embodiment, at least some filter elements are adapted to form a clot-retaining clasp after conversion.

In one embodiment, the filter element comprises an L-shaped segment, and the L-shaped segment is configured to retain a clot after conversion.

In one embodiment, the L-shaped segment comprises a first length extending distally and a second length extending proximally at an acute angle to the first length.

In one embodiment, at least one filter element includes a filter cell in the shape of a quadrangle or a curved loop. In one embodiment, the element includes a plurality of proximally-extending lengths extending from the first length configured to form a clot-retaining cone after conversion.

In one embodiment, at least some filter elements each comprise a distally-extending first segment and a bend to a proximally-extending second segment, and the second segments of at least two elements are joined by the holder to provide an annular capturing region in the closed state. In one embodiment, the bend is stiff enough to retain a clot after conversion.

In one embodiment, the filter comprises an expanding structure and is adapted to expand in a direction having a radial component after conversion to press a clot against a filter element, the support, or a vessel wall. In one embodiment, the expanding structure is in the form of a trellis which is expandable radially. In one embodiment, the expanding structure is cone-shaped pre-conversion. In one embodiment, the expanding structure is in the form of a zigzag loop.

In one embodiment, the device further comprises a pre-filter for impingement against a clot upstream of the filter. In one embodiment, the pre-filter is in the form of at least one member extending across the support. In one embodiment, the pre-filter is configured to cut a clot.

In one embodiment, at least one filter element is in the form of a lattice which is biased radially outwardly to the open state. In one embodiment, at least some filter elements have a stepped configuration for assistance with clot lysis.

In one embodiment, at least some filter elements have clot-retention protrusions. In one embodiment, at least some of said protrusions are barb-shaped.

In one embodiment, at least some filter elements are wound to store mechanical energy and held by the holder in the wound state, and are arranged so that upon conversion they unwind to release the stored energy in an action which impacts on a captured clot to break it down. In one embodiment, proximal ends of at least some filter elements include features for allowing an inserted device to grip them and to pull them inwardly in an action which cuts a captured clot.

In one embodiment, at least one filter element is configured with an arc profile which conforms with the circumference of a vessel wall when the filter element is in the open position.

In one embodiment, the filter element is flexible for enhanced conformity with a vessel wall.

In one embodiment, at least one filter element is connected to the support by a holder and extends at an acute angle of less than 40° so that there is reliable conversion even with endothelial growth.

In one embodiment, at least one filter element is compressed in the closed state to have a longitudinal curve that reverts to a substantially longitudinally straight shape that is longer in the open state.

In one embodiment, the filter is adapted to provide filtration in addition to clot retention for a period after conversion.

In one embodiment, the device comprises a plurality of filters, at least one of which is adapted to capture thrombus during an intermediate stage after conversion of a more proximal filter.

According to another aspect of the invention there is provided a vascular filter comprising: one or more capture members, the one or more capture members being configured to capture thrombus passing through a blood vessel, and the one or more capture members defining a first capture region within which thrombus may be captured. By capturing the thrombus, the filter prevents the thrombus from passing to the heart or lungs, which may cause pulmonary embolism. By supporting the capture members this ensures that the capture members are maintained in the desired location in the blood vessel.

In one embodiment of the invention the capture member is movable from a capturing state to an open state, in the capturing state the capture member being configured to capture thrombus passing through a blood vessel. In the open state the capture member may be configured to facilitate unrestricted blood flow. In the open state the capture member may be configured to capture thrombus passing through a blood vessel. Preferably the filter comprises means to temporarily hold the capture member in the capturing configuration until elapse of a first predetermined period of time. Ideally the capture member is movable from the capturing state to an intermediate state, and from the intermediate state to the open state, in the intermediate state the capture member being configured to capture thrombus passing through a blood vessel. Most preferably the capture member is biased from the capturing state towards the intermediate state. The capture member may be biased from the intermediate state towards the open state.

In another embodiment the capture member defines a second capture region within which thrombus may be captured. Preferably the second capture region is spaced apart from the first capture region. Ideally the second capture region is located proximally of the first capture region. Most preferably the second capture region has a larger capturing space than the first capture region.

In one case in the capturing state the capture member defines the capture region. Preferably in the intermediate state the capture member defines the capture region.

The capture region may be configured to be located in the region of the centre of a blood vessel. The capture region may be configured to be located in the region of a wall of a blood vessel.

In another case in the intermediate state the capture region has a smaller capturing space than in the capturing state. The capture region may be substantially conically shaped. The capture region may be substantially annular shaped. Preferably in the capturing state the capture member extends towards an apex. Ideally in the intermediate state the capture member extends towards an apex. The apex may be substantially inline with a longitudinal axis extending through the centre of a blood vessel. The apex may be substantially offset from a longitudinal axis extending through the centre of a blood vessel.

In one embodiment the filter comprises means to couple thrombus to the capture member. Preferably the coupling means is mounted to the capture member. Ideally the coupling means is engagable with thrombus.

The capture member may extend in the direction of blood flow through a blood vessel. The capture member may extend in a direction opposite to the direction of blood flow through a blood vessel.

In another embodiment the filter comprises means to reduce the size of thrombus. The thrombus reducing means may be configured to reduce the size of thrombus captured in the capture region. The thrombus reducing means may be configured to reduce the size of thrombus before being captured in the capture region. Preferably the thrombus reducing means is engagable with thrombus to reduce the size of the thrombus. Ideally the thrombus reducing means is movable relative to thrombus to reduce the size of the thrombus. The thrombus reducing means may be movable relative to thrombus prior to elapse of the first predetermined period of time. The thrombus reducing means may be movable relative to thrombus upon elapse of the first predetermined period of time. The thrombus reducing means may be movable relative to thrombus upon elapse of a second predetermined period of time. Most preferably the filter comprises means to couple the thrombus reducing means to a device for moving the thrombus reducing means relative to thrombus.

In one case the capture member comprises the thrombus reducing means. Preferably at least part of the capture member is curved. Ideally the thrombus reducing means comprises one or more protrusions. Most preferably the capture member is configured to reduce the size of thrombus upon movement from the capturing state to the open state.

In another case the thrombus reducing means is spaced apart from the capture member. Preferably the thrombus reducing means is located proximally of the capture member.

In one embodiment the filter comprises means to deliver an active agent to a blood vessel. Preferably the delivery means is configured to deliver the active agent upon elapse of a third predetermined period of time.

In one case the invention captures a clot at the centre of the vessel and moves the clot to the vessel wall. In one case the invention captures a clot at the centre of the vessel and cuts the clot into smaller pieces before or after conversion. In one case the invention cuts a clot before the clot reaches the clot reception space of the filter. In one case the invention includes an intervention to manually cut a clot before conversion. In one case the invention includes out of plane movement of the capture arms. In one case the invention includes biodegradation of separate components at different points in time. In one case the invention includes stages of filtration at different points in time. In one case the invention retains a clot against the vessel wall. In one case the invention releases a drug at a predetermined point in time.

In one case the invention includes inverted capture arms. In one case the invention includes features to hold a clot from the inside of the clot. In one case the invention includes a web/trellis/membrane to a hold clot from the outside. In one case the invention increases the radial force of the capture arms.

In this specification the terms "filter element", "capture member", and "capture arm" are used interchangeably to mean a part of a filter.

BRIEF DESCRIPTION OF THE DRAWINGS

The invention will be more clearly understood from the following description of some embodiments thereof, given by way of example only, with reference to the accompanying drawings, in which:

FIGS. 5 to 25 are diagrams illustrating a filter device having loop-shaped filter elements and which pass through each other in an arrangement to provide the double cones, and in which FIGS. 5 to 7 show the device when open, FIGS. 8 to 14 show how the device is assembled, FIGS. 15 to 18 show the device when closed for capturing emboli, and FIGS. 19 to 25 are flat pattern drawings showing particular details of parts of the device;

FIGS. 26 to 34 show a filter device which also has looped filter elements, and in this case a strut for improved filtering efficiency and interconnection of the loops, in which FIGS. 26 to 30 show the device when closed for emboli capture and FIGS. 31 to 34 show the device when open;

FIGS. 38 to 40 are diagrams showing a filter device having two hoops which are directly interconnected, without longitudinal support members extending between them;

FIGS. 41 to 54 show a filter device having three looped filter elements and three straight filter elements, in which FIGS. 51 to 54 show clot retention;

FIGS. 63 to 70 show a variation in which filter elements are straight;

FIGS. 83 to 90 show a device having straight filter elements with twisted ends;

FIGS. 107 to 114 show a device having filter elements with straight and forked members;

FIGS. 125 to 138 show embodiments in which two filter cones face the same way, a distal one being for clot retention post conversion;

FIGS. 192 to 205 show details of a further filter device with an M-shaped filter, in which FIGS. 192 to 197 are flat-pattern drawings;

FIGS. 206 to 214 show a device with M-shaped filter elements of a different configuration, in which FIGS. 206 to 210 are flat pattern drawings;

FIGS. 240 to 243 show a device with a conical filter having a number of straight filter elements and a number of profiled filter elements;

FIG. 277 shows a device having a filter element with a loop, and FIGS. 278 and 279 show variations in which the filter element has more than one loop;

FIGS. 280 to 283 are side views showing alternative arrangements, particularly a kinked filter element which is perpendicular to the vessel wall at a proximal end (FIG. 280), a flexible filter element (FIG. 281), and curved filter elements (FIGS. 282 and 283);

DETAILED DESCRIPTION OF THE INVENTION

Figure 1:
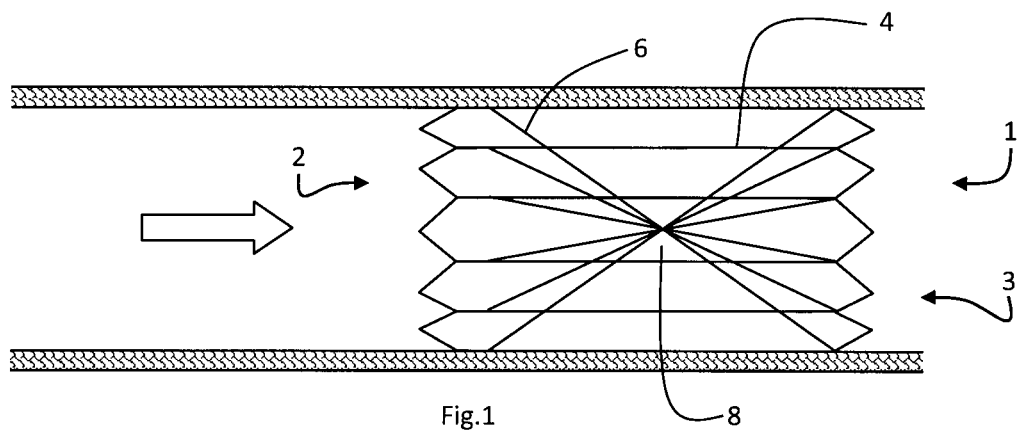
FIGS. 1 to 4 are a series of diagrams illustrating operation of a filter device, in which there are two cones meeting at a mutual apex, a proximal cone capturing a clot and decreasing in size after conversion as the clot is lysed.
Figure 2:
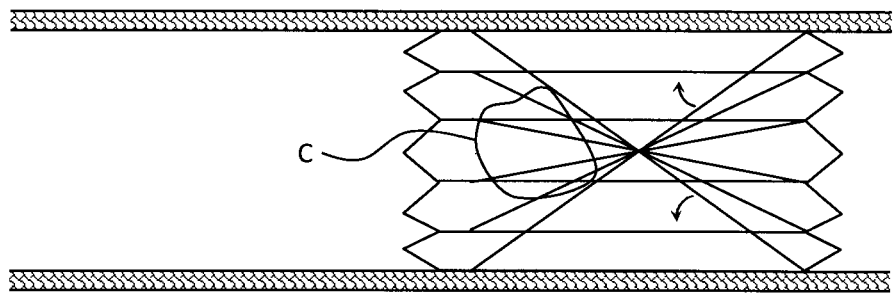
Figure 3:
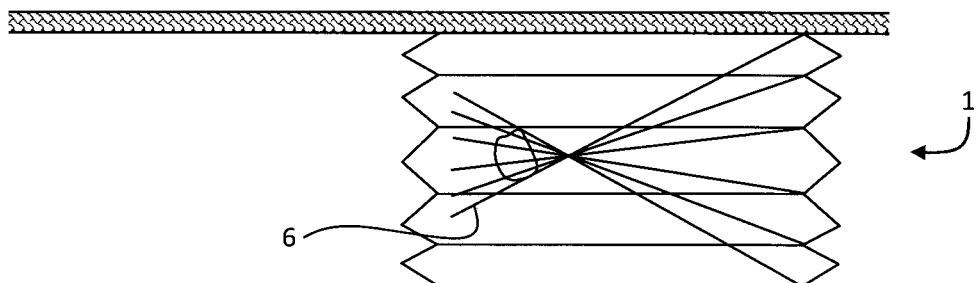
Figure 4:
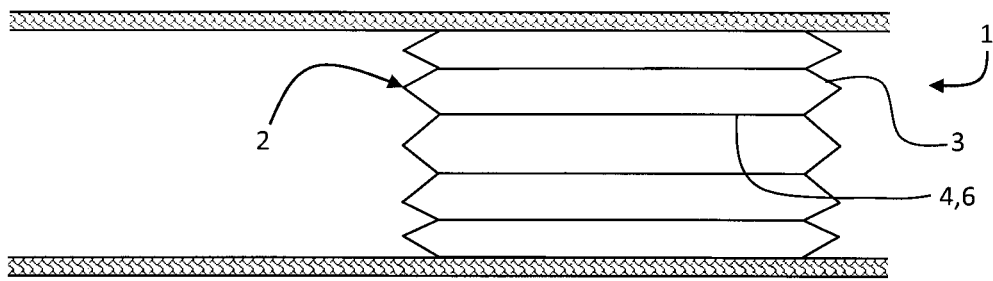
Figure 10:
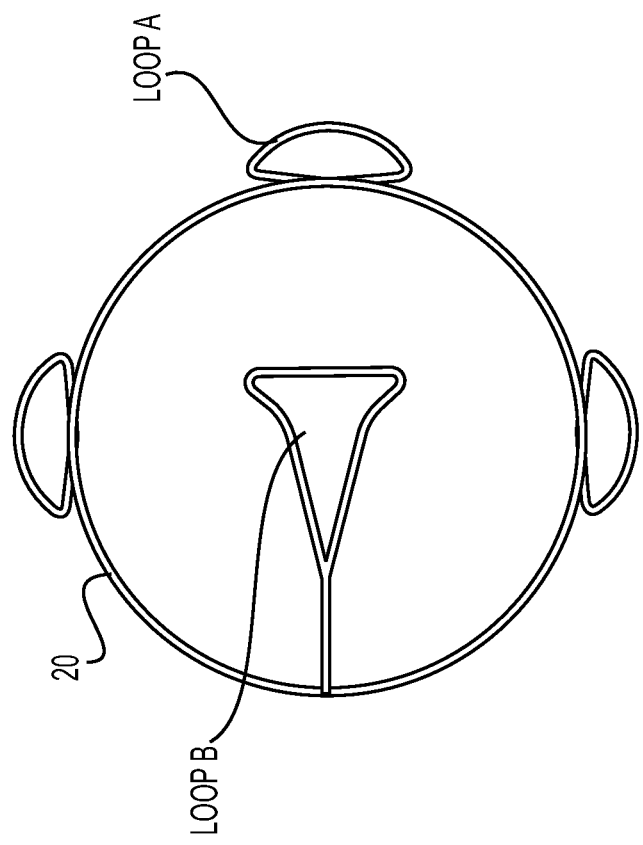
Figure 9:
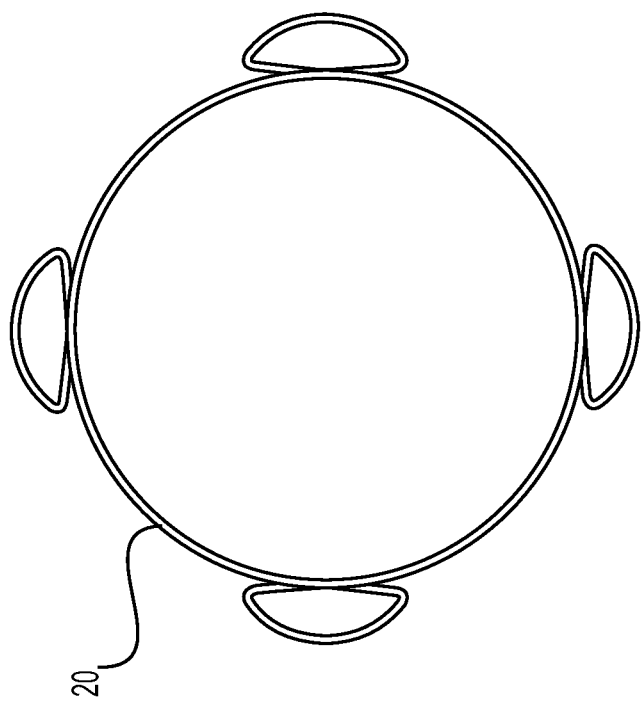
Figure 11:
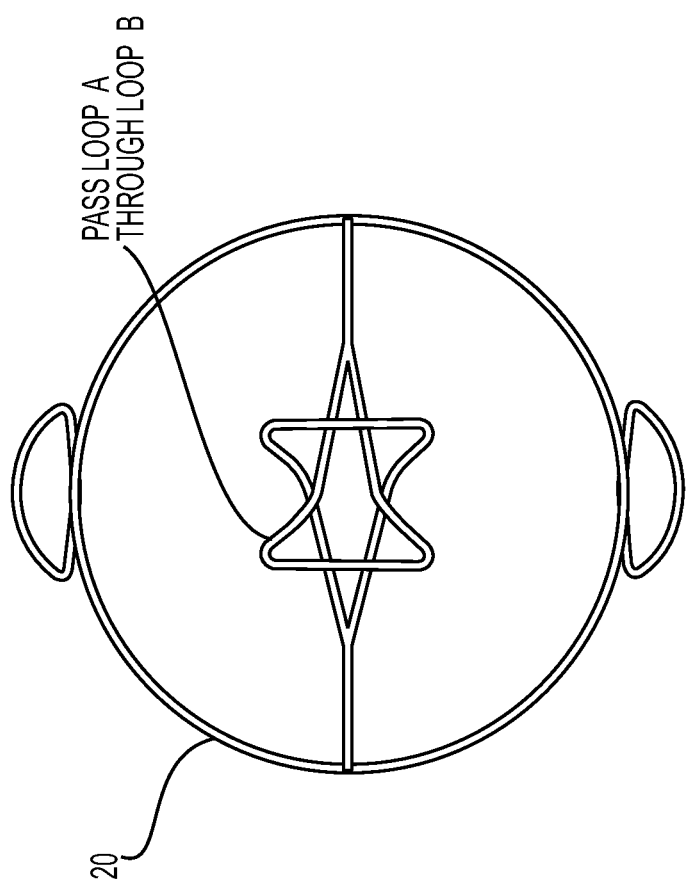
Figure 12:
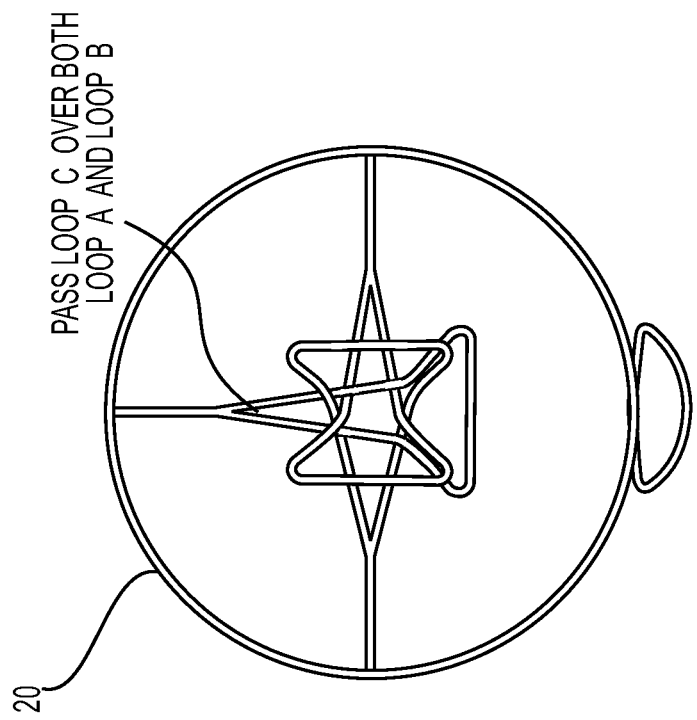
Figure 14:
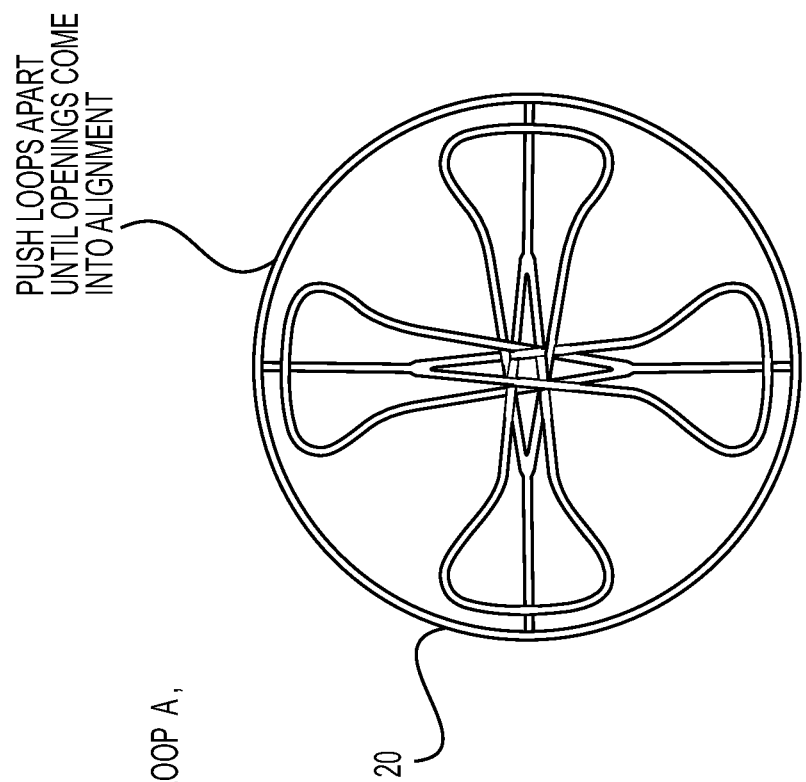
Figure 13:
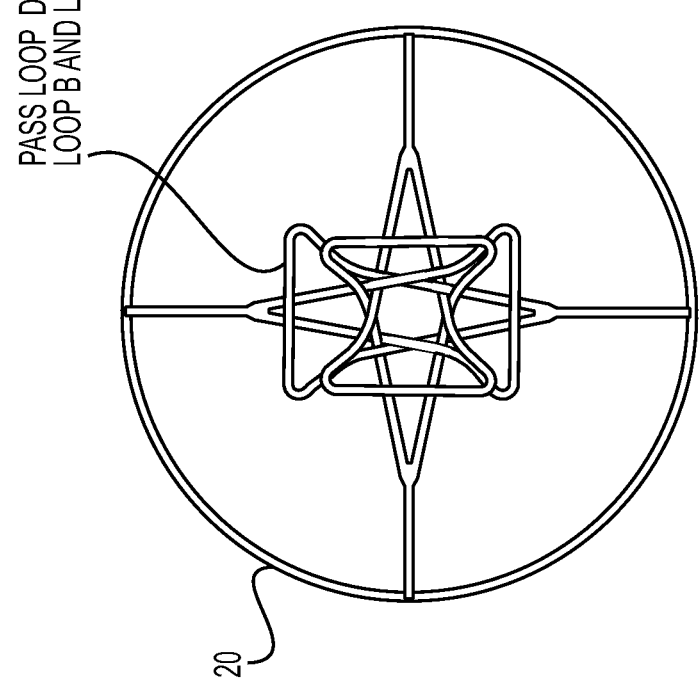

A vascular filter is suitable for use as an inferior vena cava filter in the inferior vena cava. In general terms the filter is movable at conversion from a capturing or closed state to an open state upon elapse of a predetermined period of time. In the capturing state the filter is configured to capture thrombus passing through the inferior vena cava towards the heart and the lungs. The filter may thus be used to prevent pulmonary embolism. In the open state the filter is configured to facilitate unrestricted blood flow.

In most of the following embodiments the filter device is deployed by collapsing for delivery, and at least partially loaded into a delivery catheter. The delivery catheter is advanced through the inferior vena cava until the collapsed filter device reaches the desired location in the inferior vena cava. A restraining sheath of the delivery catheter is then moved proximally relative to the filter to fully uncover the filter. Due to the biasing nature of the filter, the filter 1 moves from being collapsed for delivery to being expanded when deployed. When deployed, the support exerts a radially outward force on the internal wall of the inferior vena cava to support the capture arms in the desired position in the inferior vena cava.

FIGS. 1 to 4

A filter device 1 is provided with a double cone filter. A support comprises a proximal hoop 2, a distal hoop 3, and longitudinal support elements 4 interconnecting the hoops. Filter elements 6 each extend from a hoop to the other hoop, at an opposing peak. Hence the filter elements 6 form a double cone arrangement with a common apex 8 in the centre. The filter elements 6 may be releasably attached to the proximal hoop 2. Preferably, a holder retains the filter elements in the capturing position at the common apex 8. Eyelets or a stop feature may be provided to reduce the likelihood of the holder moving during use. Where an apex tie is employed, the proximal ends of the filter elements can be positioned at a distance from the vessel wall during use by varying the apex tie position or the length of the filter elements. This will prevent endothelial encapsulation of the proximal filter element ends which could hinder conversion. Where the filter element ends are attached to the proximal support hoop, elongated ties may be incorporated to keep the proximal filter element ends at a distance from the vessel wall.

The proximal support hoop 2 comprises a wire element which extends circumferentially around the internal wall of the inferior vena cava in a sinusoid wave pattern. Similarly the distal support hoop or hoop 3 comprises a wire element which extends circumferentially around the internal wall of the inferior vena cava in a sinusoid wave pattern. The support struts 4 extend longitudinally along the internal wall of the inferior vena cava. The support struts connect the proximal support hoop to the distal support hoop. In this case the proximal support hoop, the distal support hoop and the support struts are formed integrally. The proximal support hoop, the distal support hoop and the support struts may be of a shape-memory material, such as Nitinol™

In use, upon release of the filter elements 6 from the proximal hoop 2, through biodegradation or application of an energy stimulus, the proximal cone reduces in size as the apex moves in the proximal direction. However, a clot if present prevents the filter elements from fully opening and they continue to retain a proximal cone shape, although the cone is smaller. The blood flow causes the clot C to impinge against the filter elements 6 to retain the proximal cone. Thus there is a natural balance between the bias forces of the filter elements and the force exerted by the clot in the blood flow direction. This cone decreases in size as the clot C decreases in size. Eventually, when the clot has disappeared all of the filter elements return to the vessel wall. The apex may be arranged or provided with means to keep it intact during conversion until it reaches the most proximal end of the filter elements to keep the proximal conical shape until the clot has completed lysis.

It will be appreciated from the above embodiment and several of the following embodiments that the device not only, after conversion, retains a clot if present but additionally continues to provide filtration for a period after conversion.

FIGS. 5 to 25

A filter device 20 comprises a proximal hoop 21, a distal hoop 22, and longitudinal support elements 23 interconnecting the hoops. Filter elements 25 to 28 are in the form of loops cantilevered onto a peak of the distal hoop 22.

The filter device 20 is prepared for use in a method as shown in FIGS. 8 to 15, in which the loops are labelled A, B, C, and D. Loop A passes through loop B, loop A passes through loop B, loop C passes through both loops A and B, and loop D passes through loops A, B, and C. The loops are then pushed apart until their openings come into contact, thus forming an apex.

The loops 25 to 28 are of different sizes so that they can be passed easily through other loops as described above. A biodegradable pin 29 extends through two loops so that the capturing position is maintained. Alternatively a holder member is a loop or tie.

In use, a clot is retained by the four loops 25 to 28 when they are in the closed position. As the holder member degrades, the natural resilience of the loops urges then to the open position. However, if there is a clot present the clot retains the loops 25 to 28 closed in a manner similar to that illustrated in FIGS. 1 to 5. It is only when the clot is lysed to a predetermined size that the loops 25 to 28 are free to completely open to the position shown in FIG. 5.

In a variation, the loops may be formed to include a radially inward curve as viewed when active, thus preventing endothelial encapsulation. Post conversion, this becomes a radially outward curve due to the different angle to the axis, promoting endothelial encapsulation.

FIGS. 19 to 25 are flat pattern drawings showing various parts of the filter 20 in more detail.

It will be appreciated that because the filter elements are in the form of loops they have greater strength than single arms in addition to providing greater capturing efficiency.

FIGS. 26 to 32 show a filter device 40 having a proximal support hoop with only four peaks, a distal support hoop 42 also with only four peaks, and longitudinal vessel-contacting support members 43 extending between the hoops 41 and 42. There are four looped filter elements 44, 45, 46, and 47. As shown most clearly in FIGS. 27 and 29 the filter loops are connected by a single cantilever link 49 to a proximal peak of the distal hoop 42. A filtering strut 50 extends into the associated loop for added filtering efficiency and for interconnection. FIG. 26(b) shows a holder pin 48 connected between two of the filter elements, enough to retain them all interconnected.

Figures 28, 29:
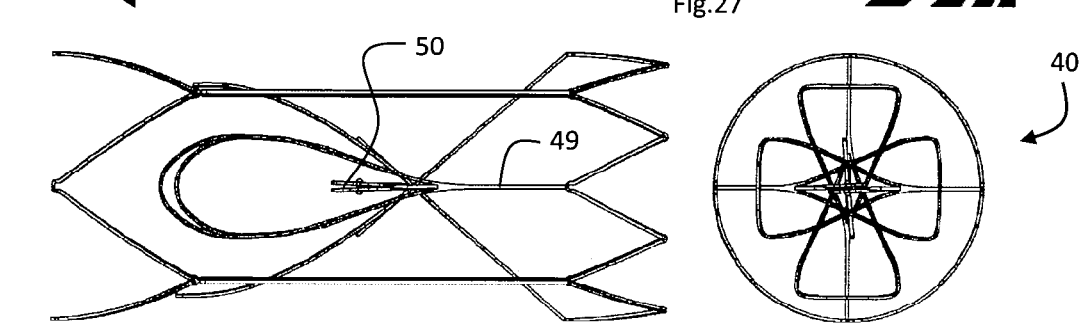
Figure 30:
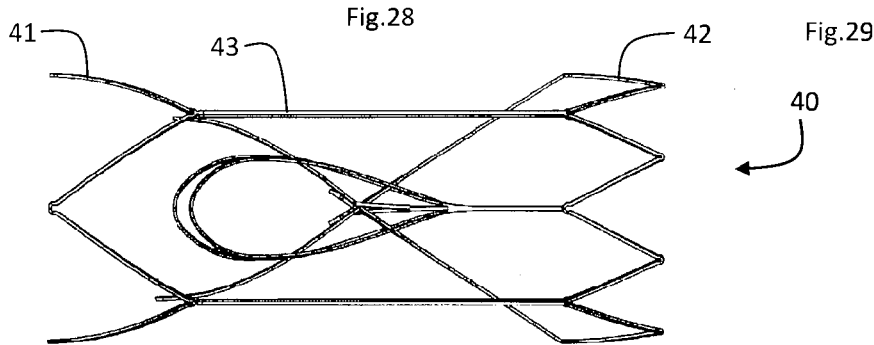
Figures 31, 32, 33, 34:
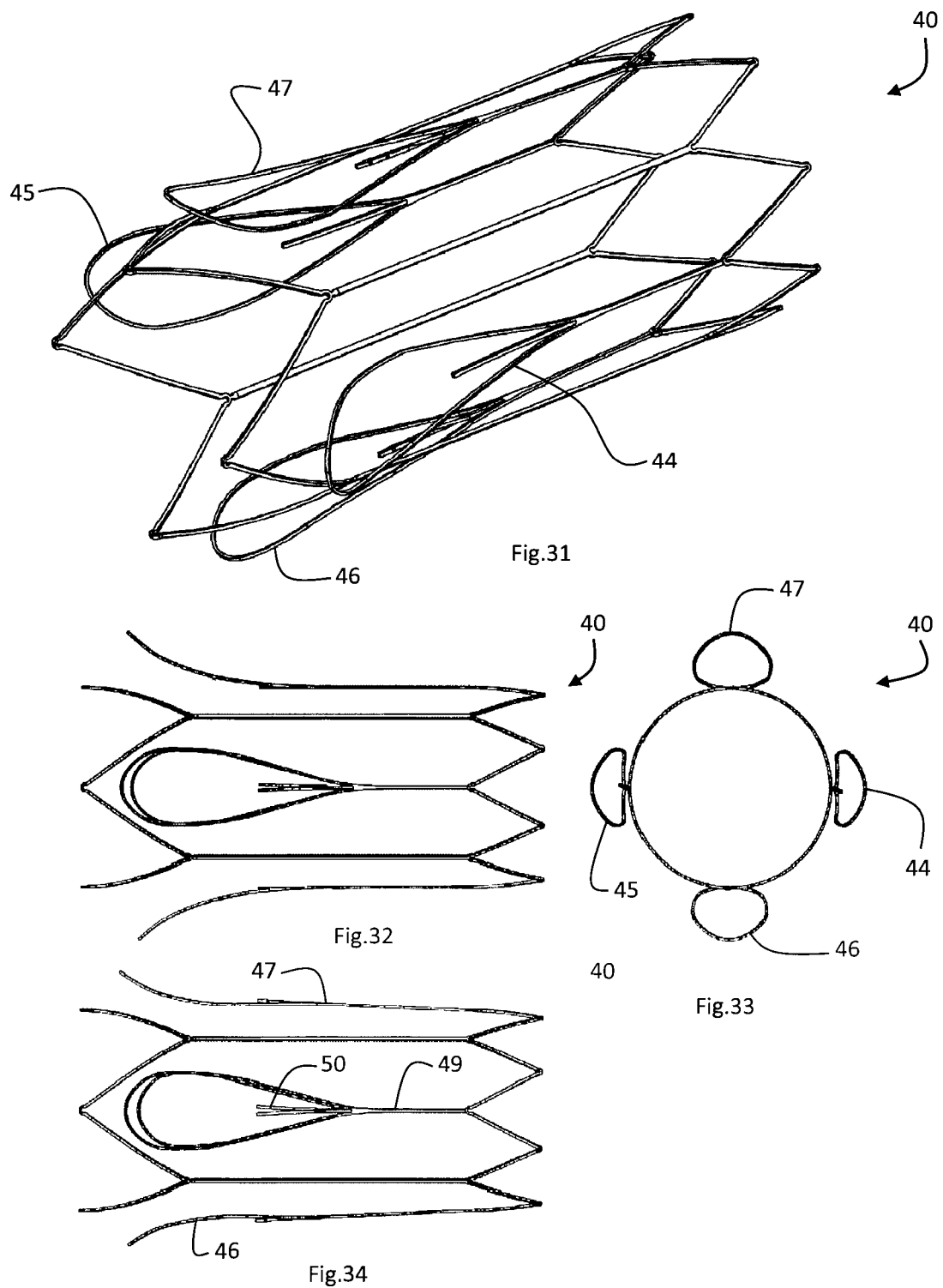

The filtering struts 50 are bifurcated, and the ends may be bent apart as shown in FIG. 29 for interconnection.

As shown most clearly in FIGS. 30 to 34 the filter elements 44 to 47 are biased radially against the vessel wall in a manner to promote endothelial growth.

Figure 35:
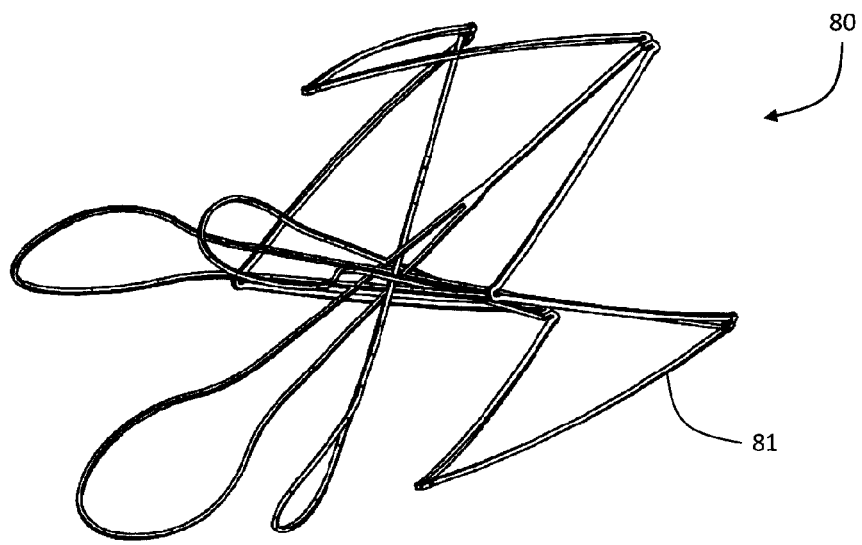
FIGS. 35 to 37 are diagrams showing a filter device also having four looped filter elements, however there is only a distal support hoop in this case.
Figure 36:
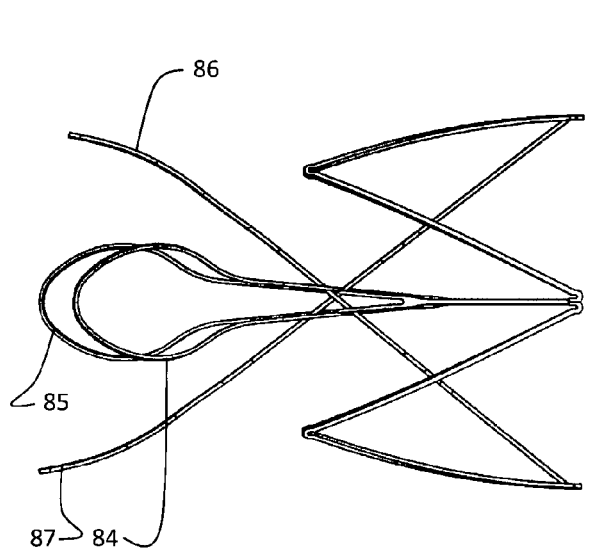
Figure 37:
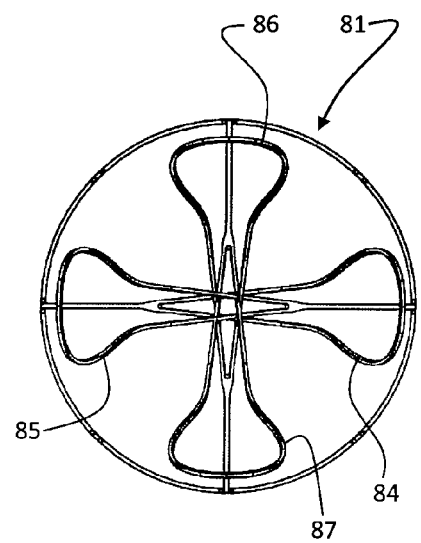
Figure 41:
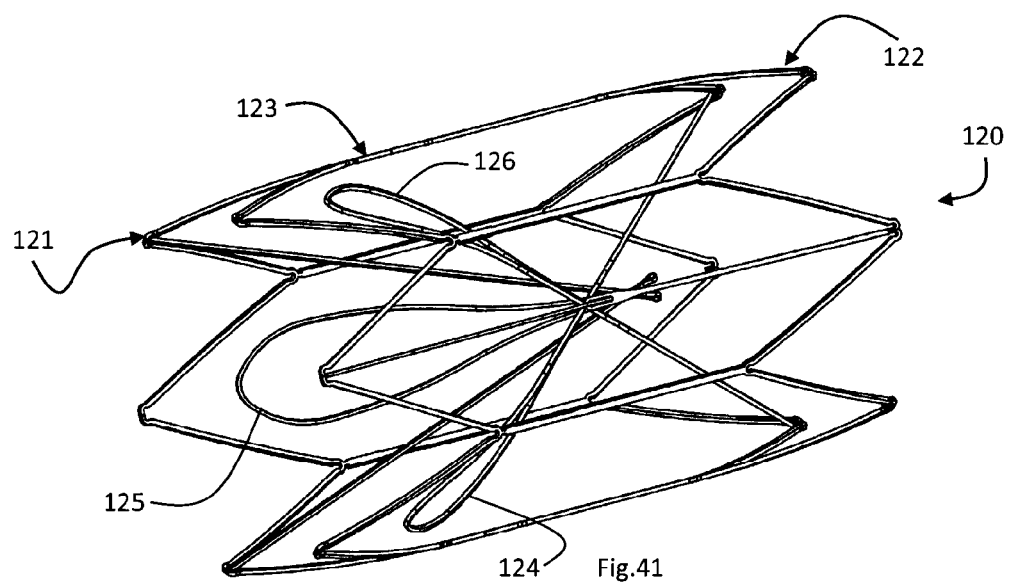
Figure 42:
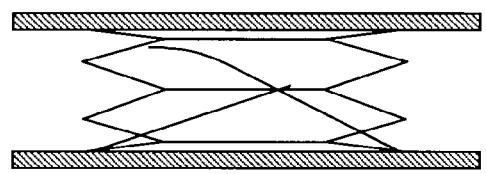
Figure 43:
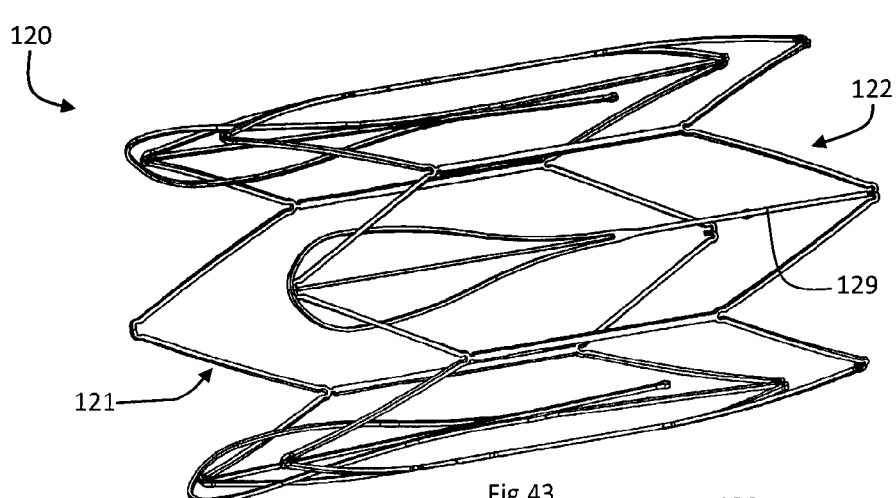

FIGS. 35 to 37

A filter device 80 in this embodiment has only a single, distal, support hoop 81. This supports four looped filter elements 84, 85, 86, and 87. This device is particularly simple and is suited to situations where space is confined.

FIGS. 38 to 40

A filter device 100 has a distal support hoop 101 and a proximal support hoop 102 which are directly interconnected without a longitudinal support. Four looped filter elements 104, 105, 106, and 107 are supported from the distal end of the proximal hoop peaks.

FIGS. 41 to 54

Figure 44:
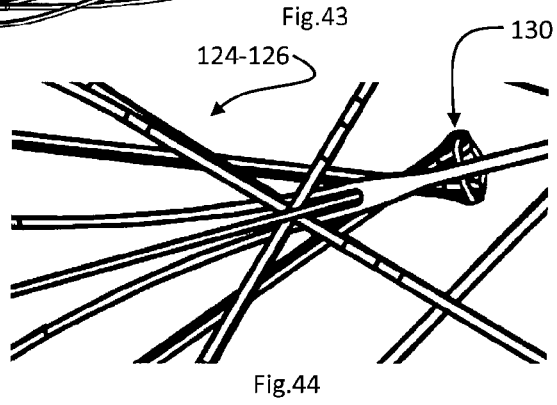
Figure 45:
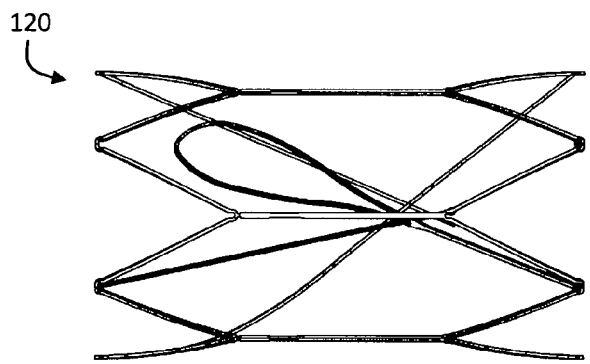
Figure 46:
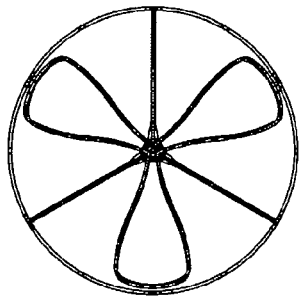
Figure 47:
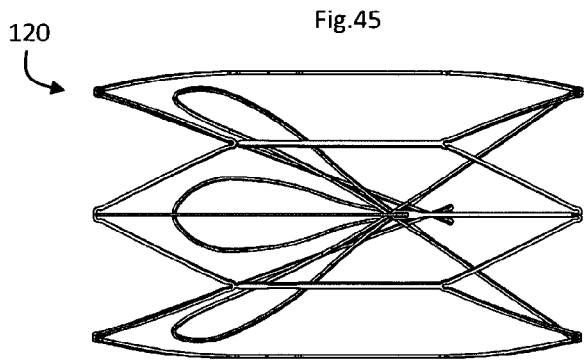
Figure 48:
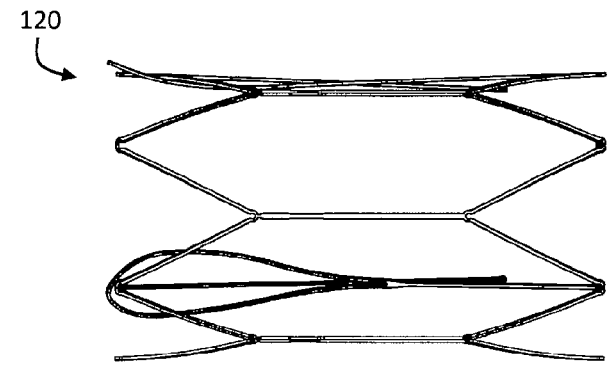
Figure 49:
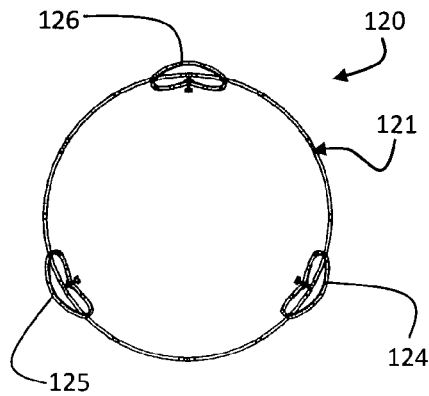
Figure 50:
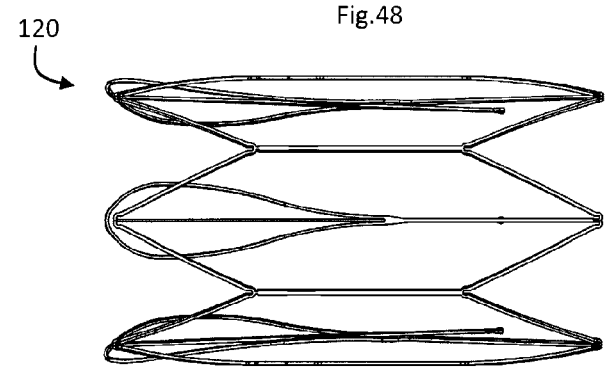
Figure 55:
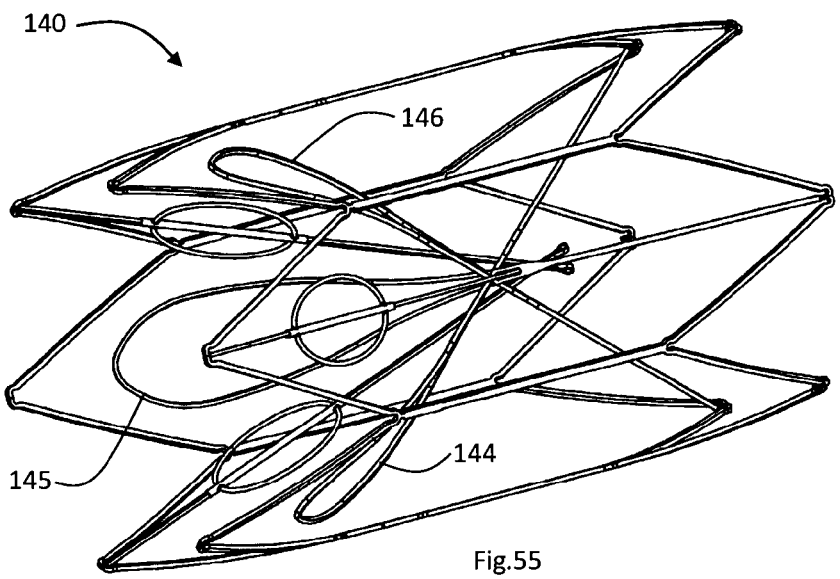
FIGS. 55 to 62 show a filter device also having three looped filter elements, in this case with the other filter elements including loops for enhanced capture efficiency.
Figure 56:
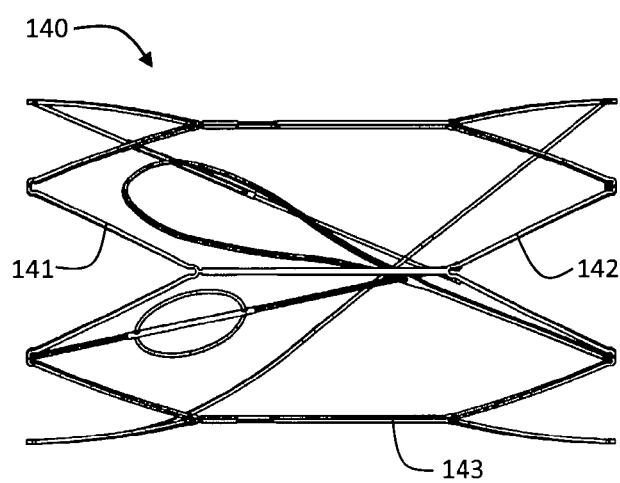
Figure 57:
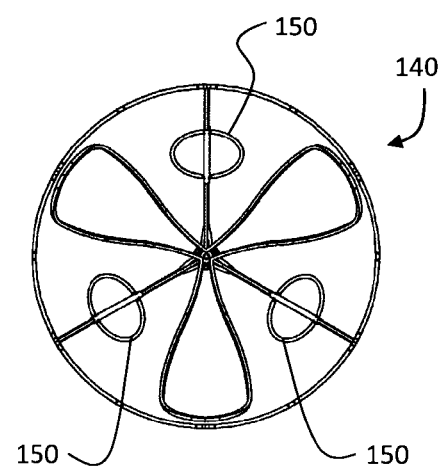
Figure 58:
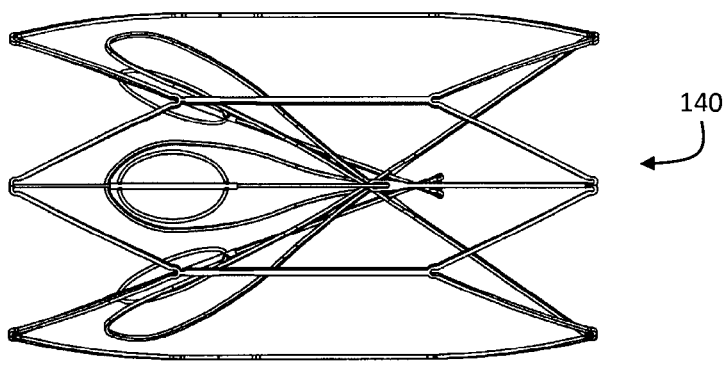
Figure 59:
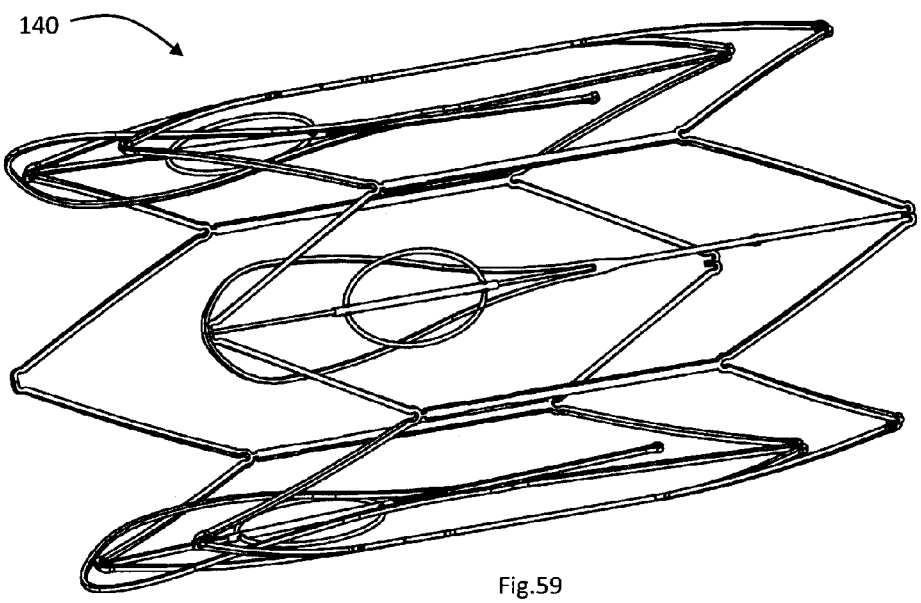
Figure 60:
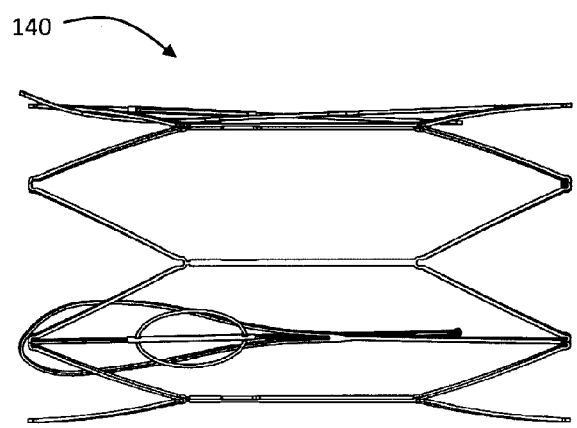
Figure 61:
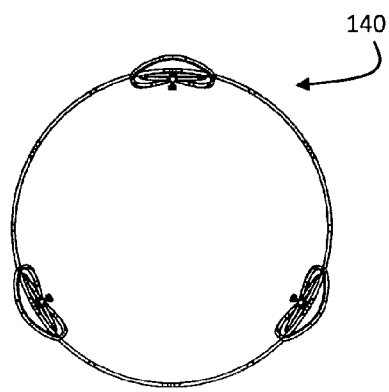
Figure 62:
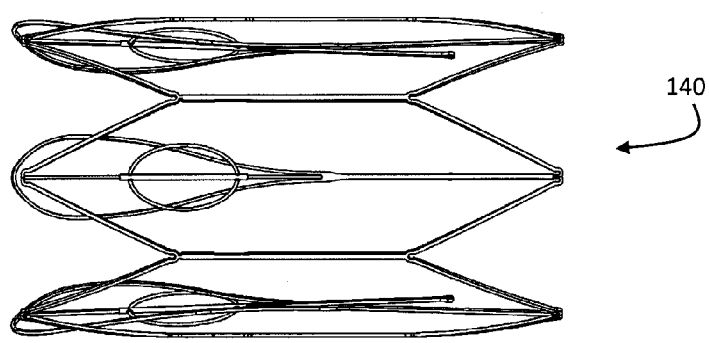
Figure 67:
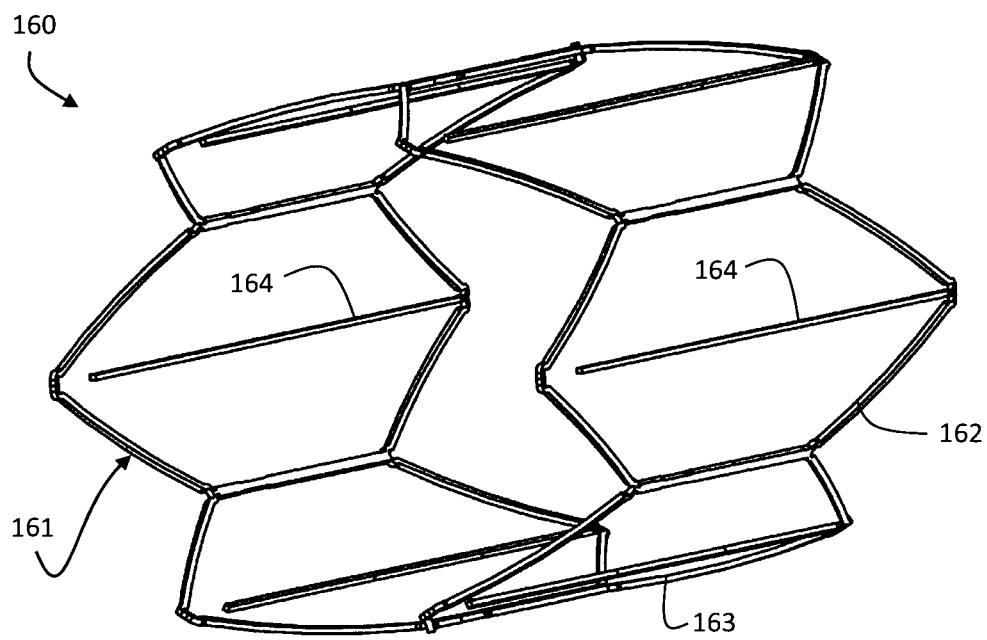
Figure 68:
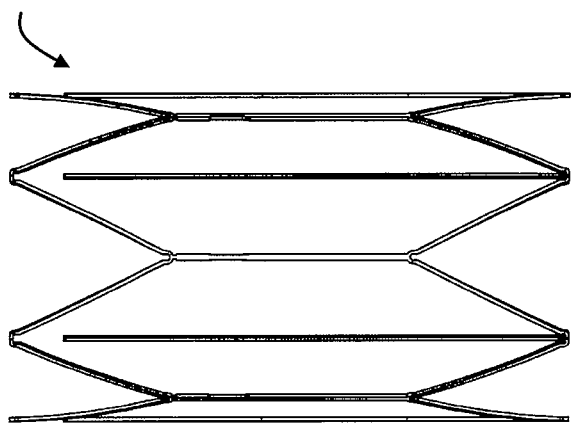
Figure 69:
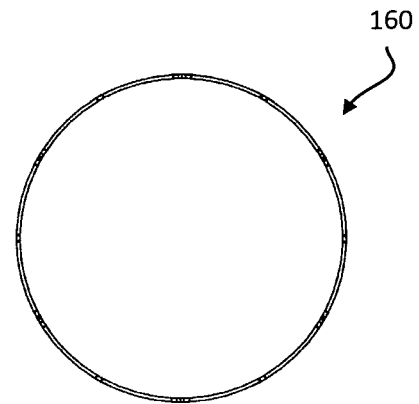
Figure 70:
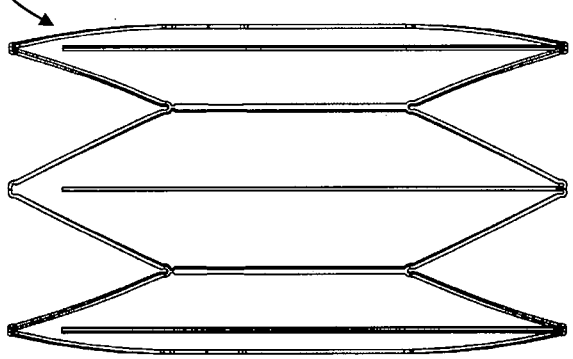
Figure 71:
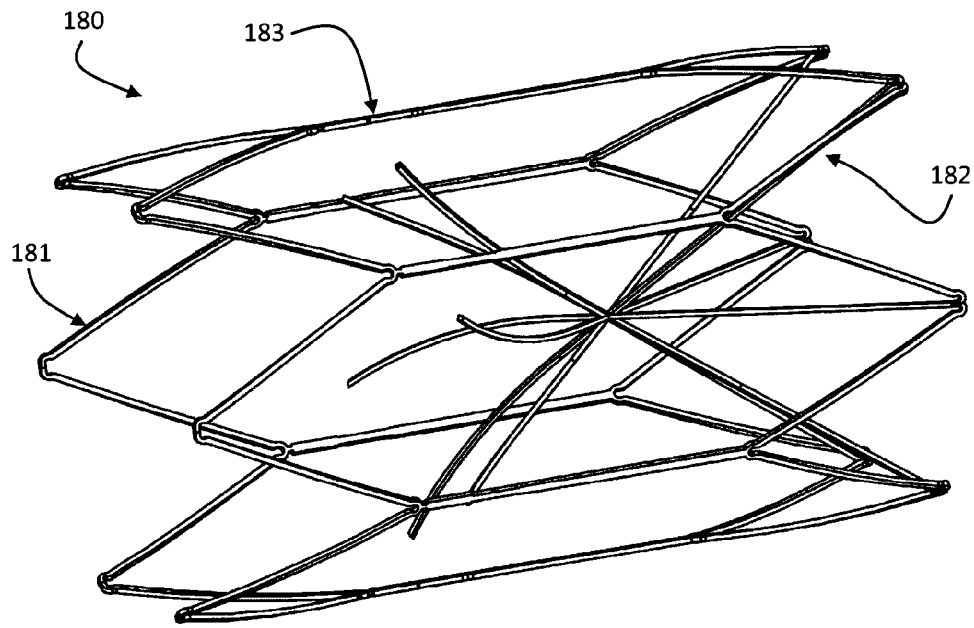
FIGS. 71 to 78 show a variation in which filter element ends are curved radially at their proximal ends.
Figure 72:
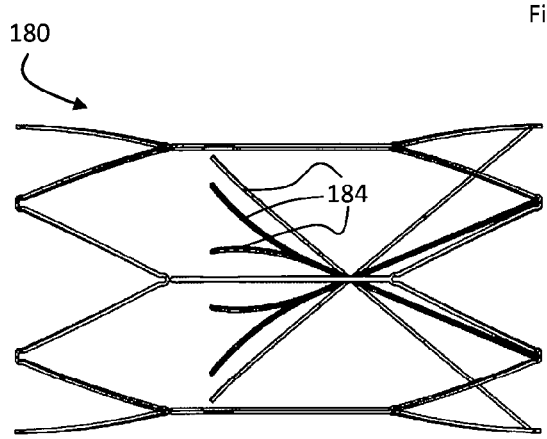
Figure 73:
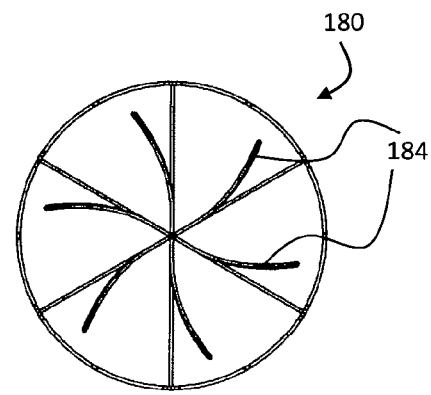
Figure 74:
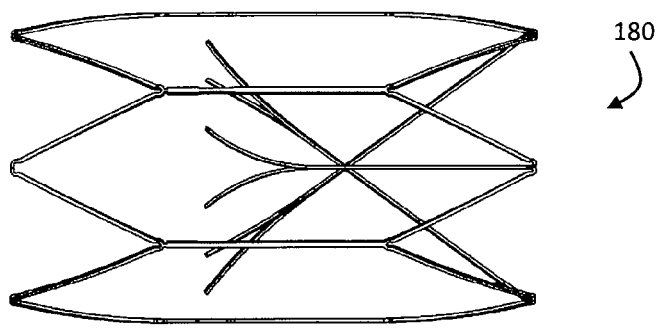
Figure 75:
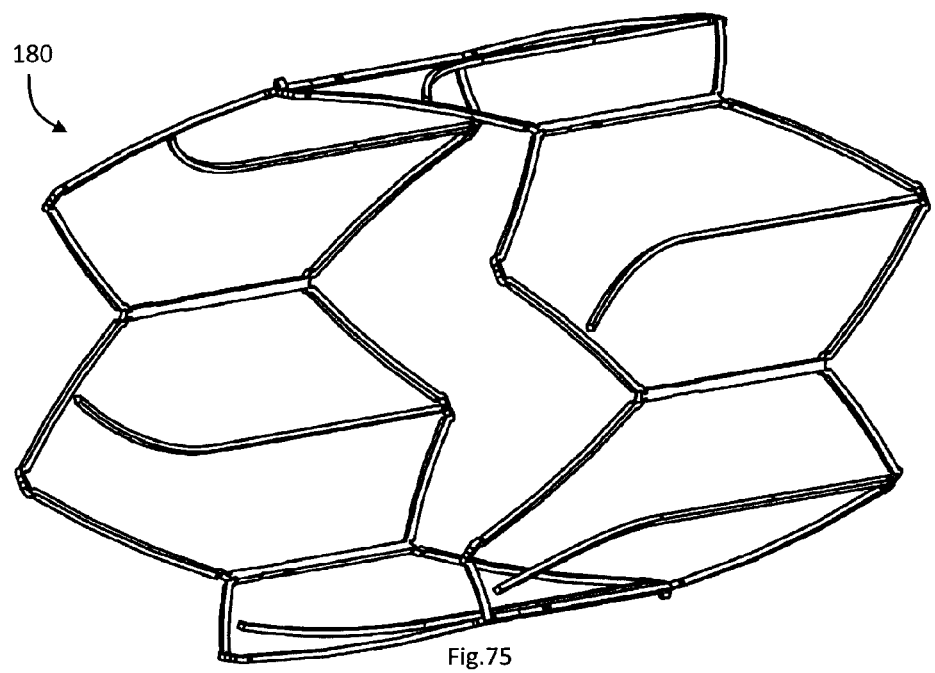
Figure 76:
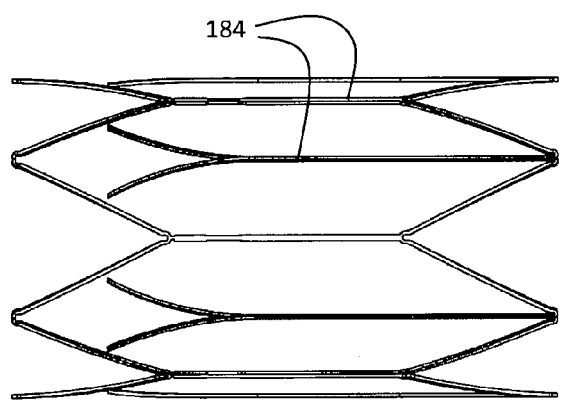
Figure 77:
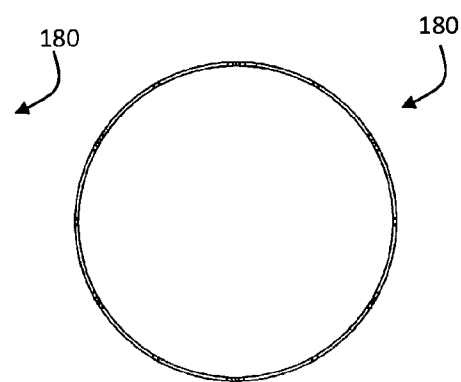
Figure 78:
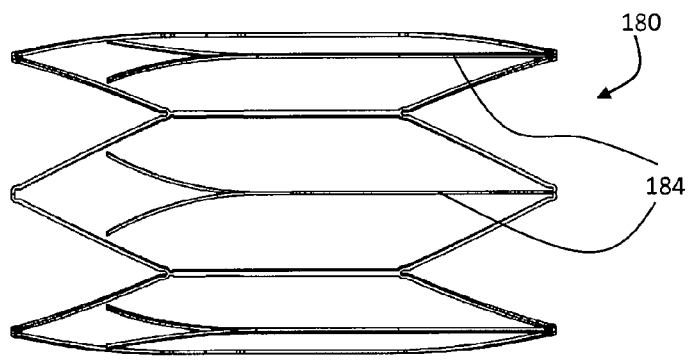
Figure 79:
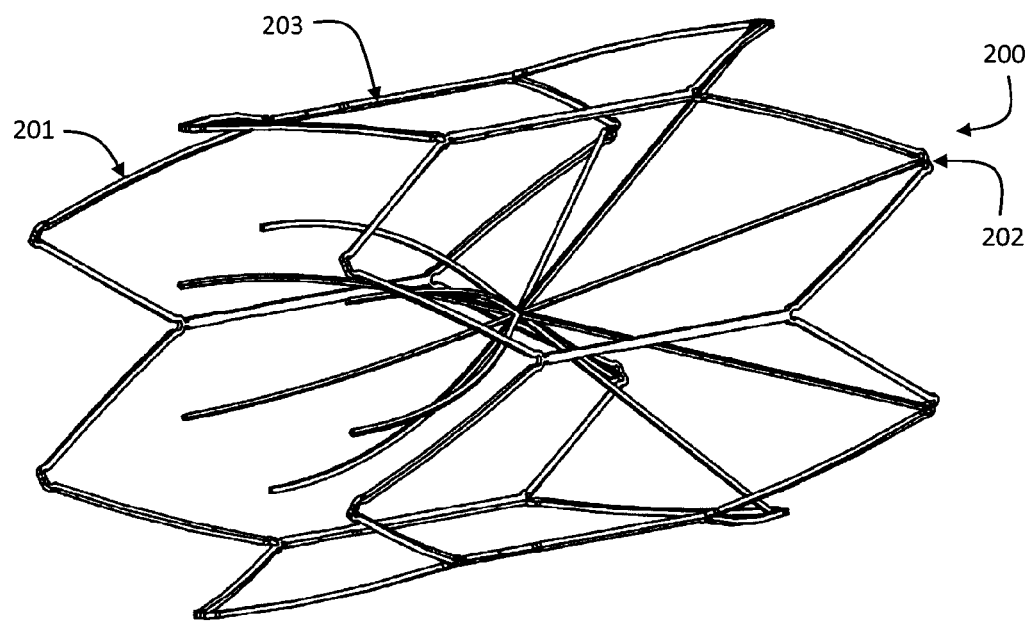
FIGS. 79 to 82 show a variation in which free ends of the filter elements are configured so that they are curved inwardly in the closed state and outwardly in the open state.
Figure 80:
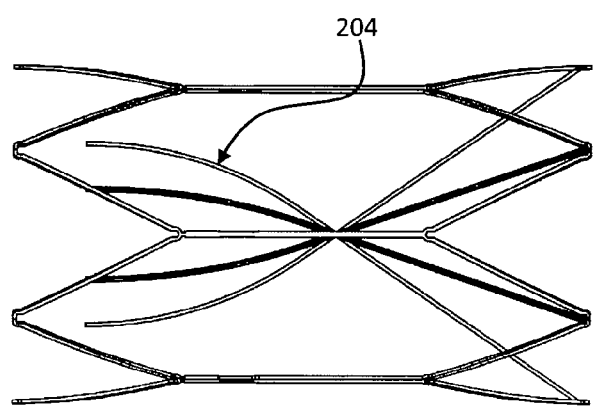
Figure 81:
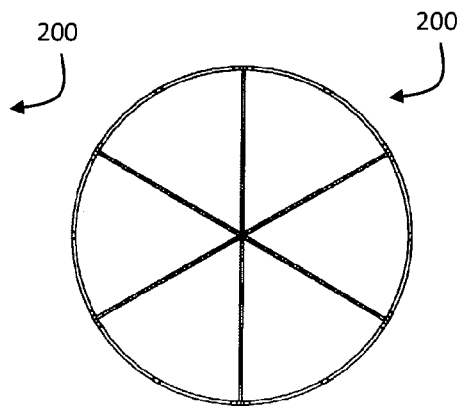
Figure 82:
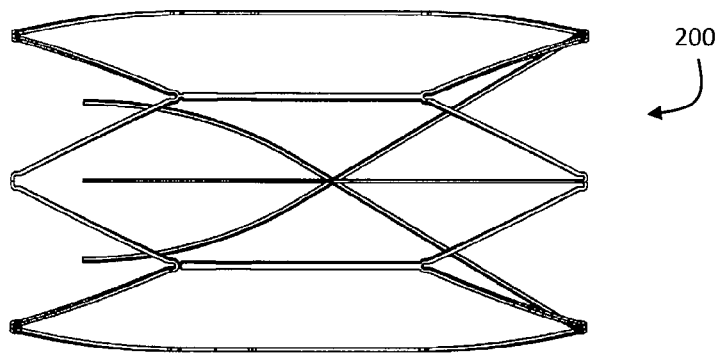
Figure 91:
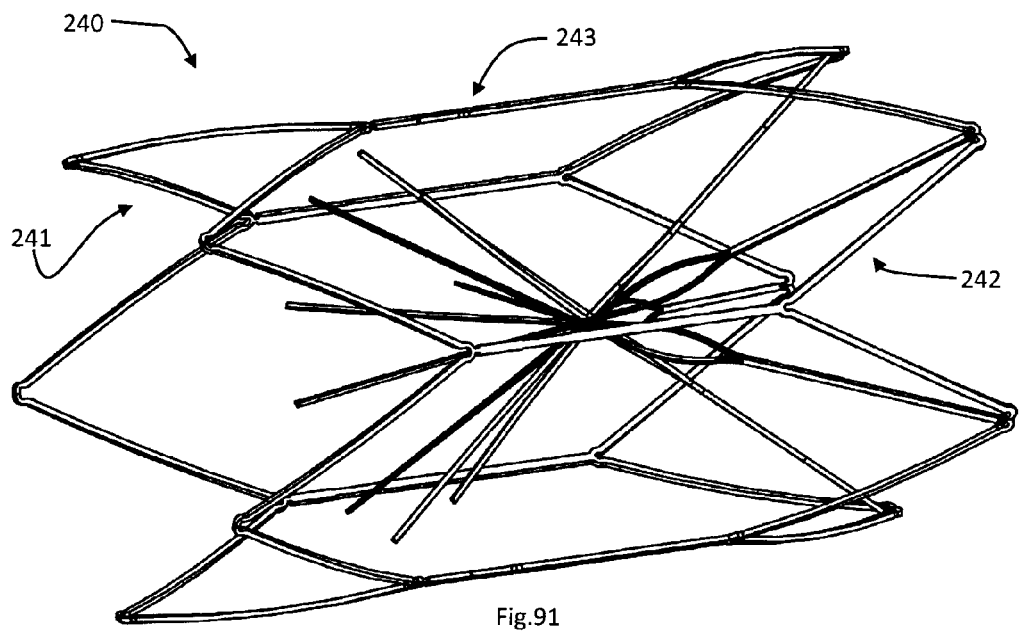
FIGS. 91 to 98 show a device having Y-shaped filter elements.
Figure 92:
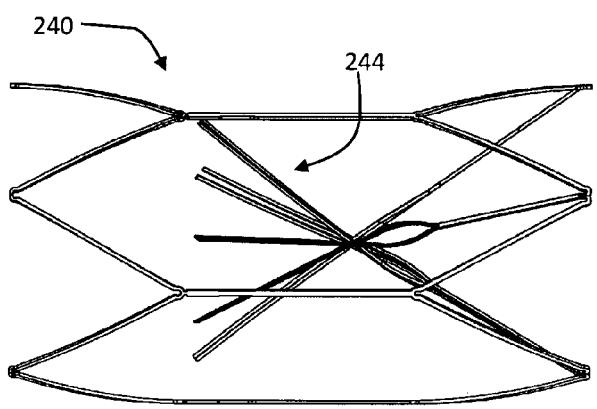
Figure 93:
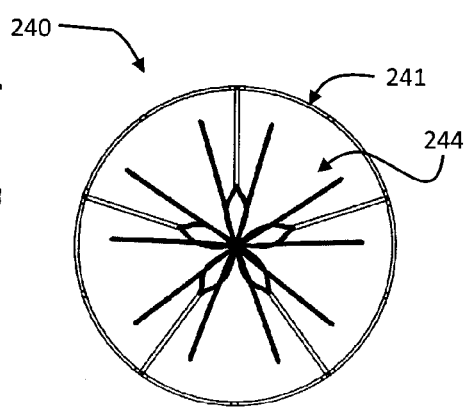
Figure 94:
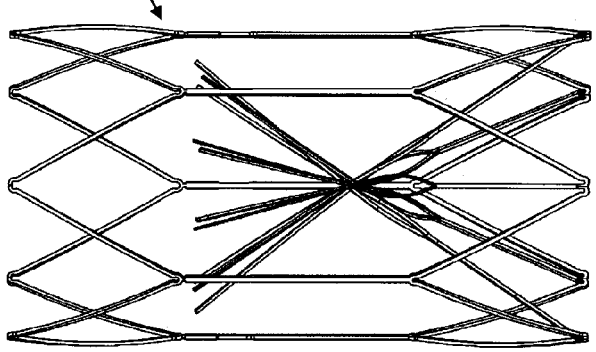
Figure 95:
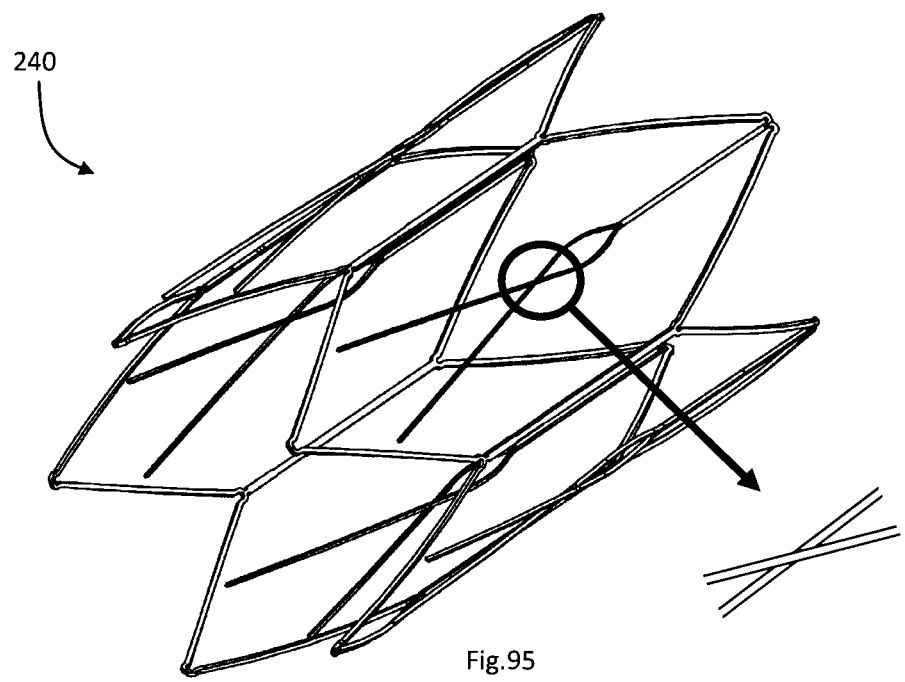
Figure 96:
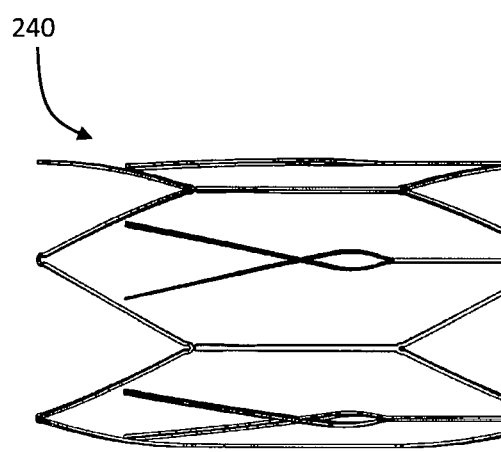
Figure 97:
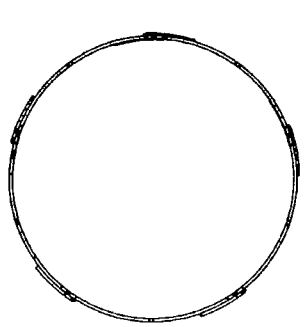
Figure 98:
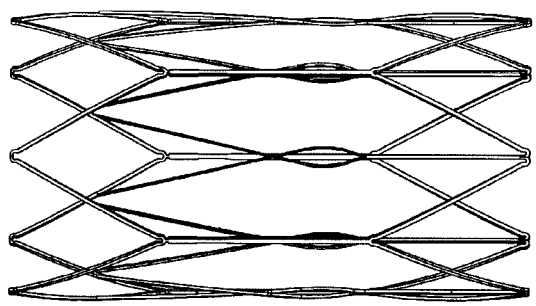
Figure 99:
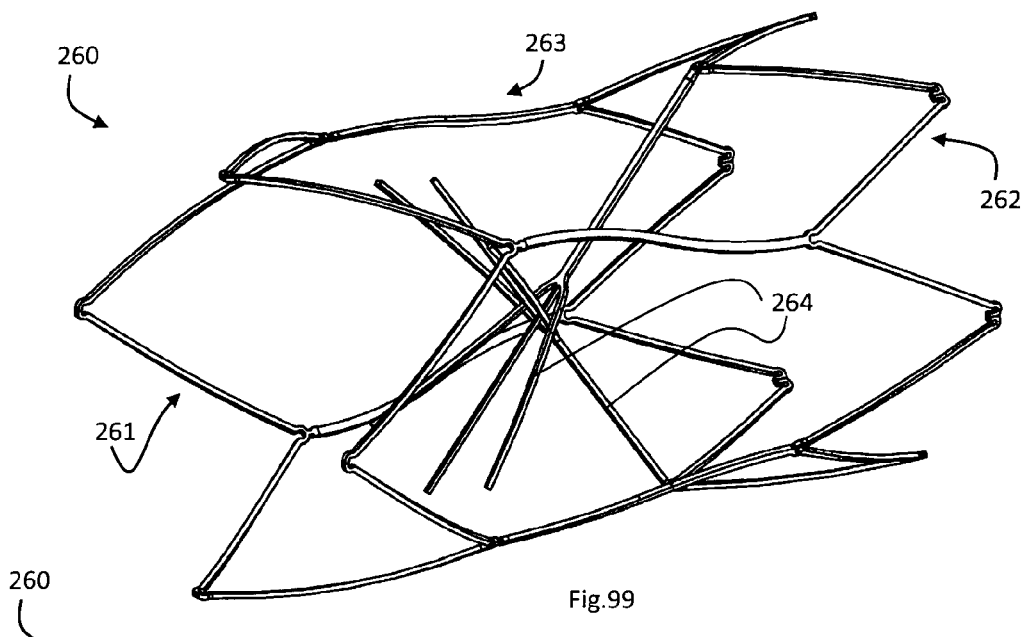
FIGS. 99 to 102 show a device having forked filter elements.
Figure 100:
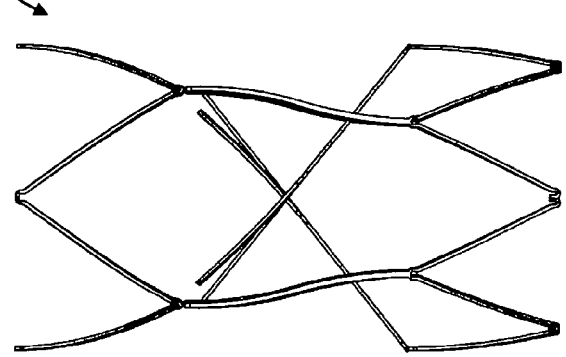
Figure 101:
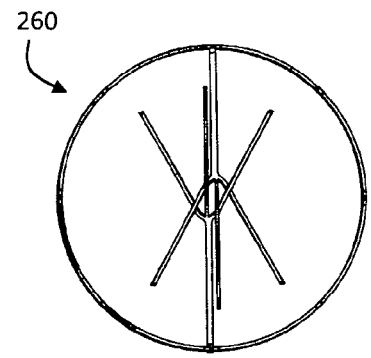
Figure 102:
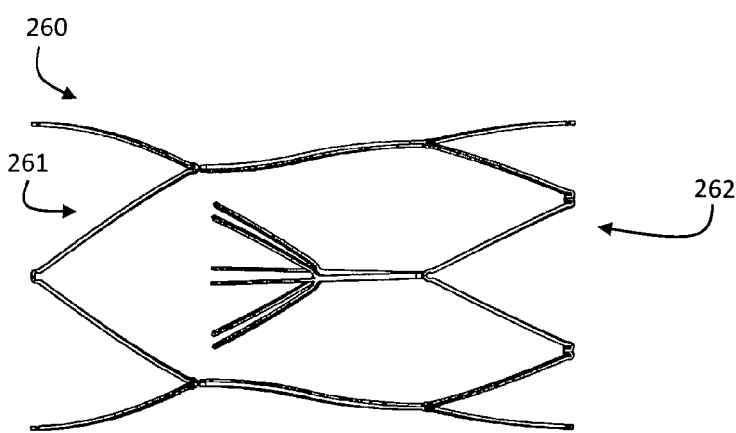
Figure 103:
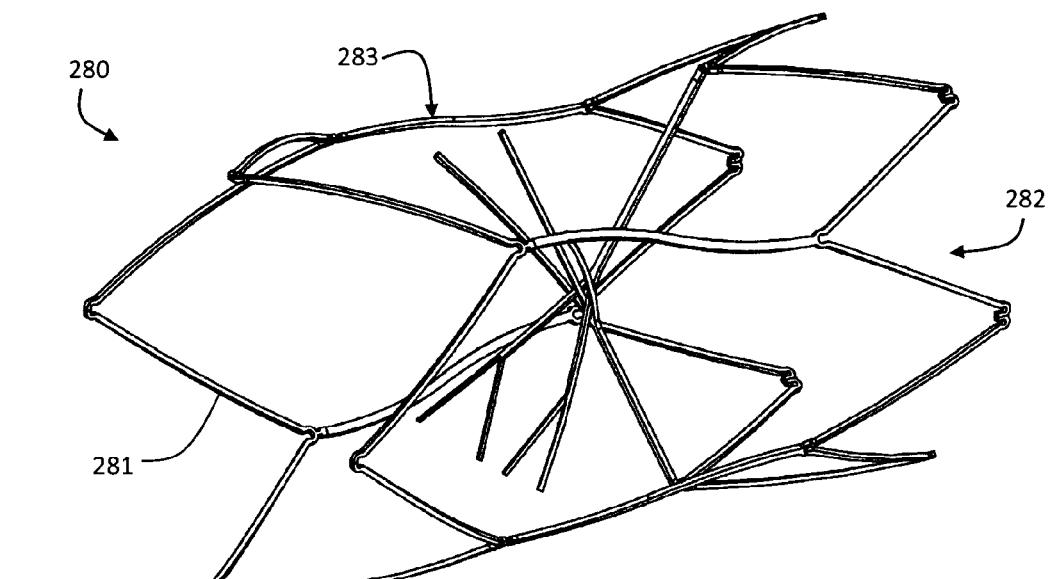
FIGS. 103 to 106 show an alternative such embodiment.
Figure 104:
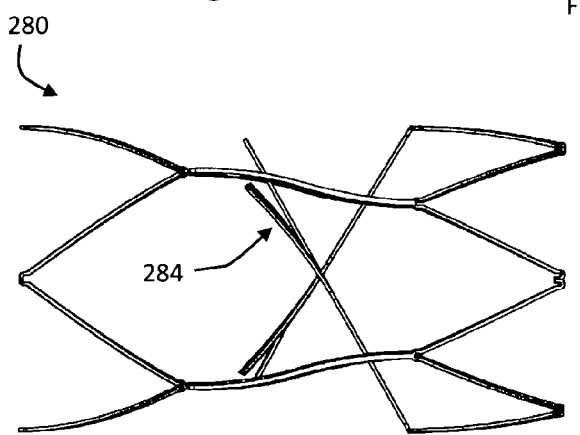
Figure 105:
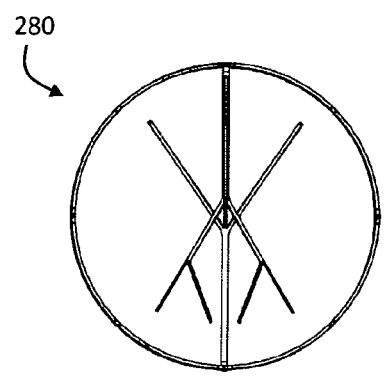
Figure 106:
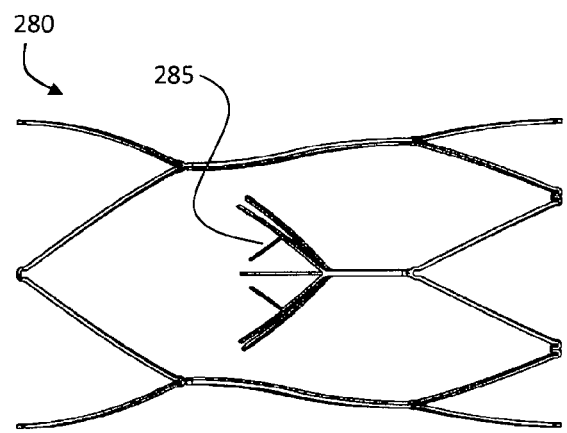
Figure 111:
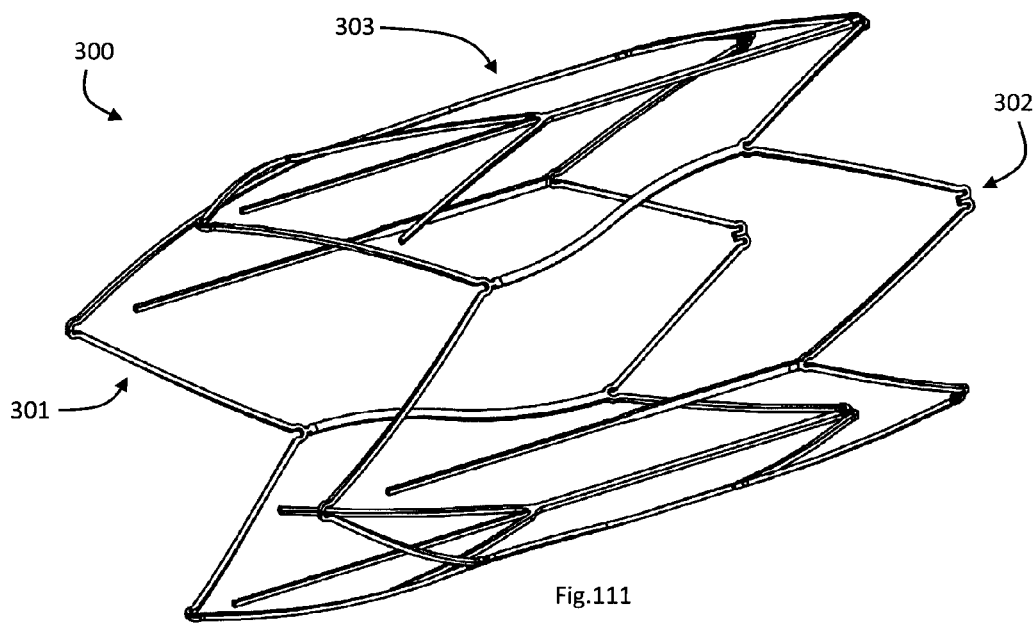
Figure 112:
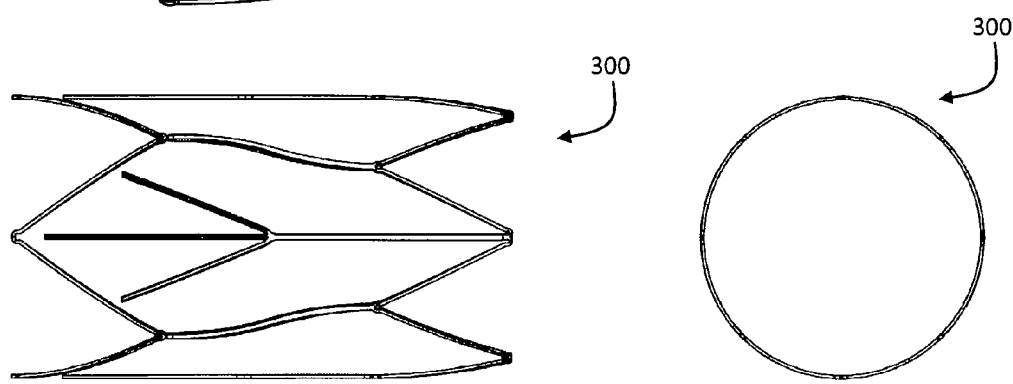
Figure 113:
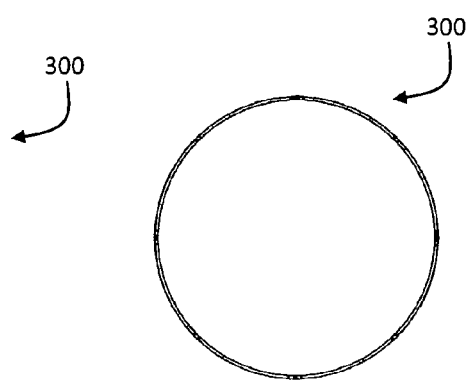
Figure 114:
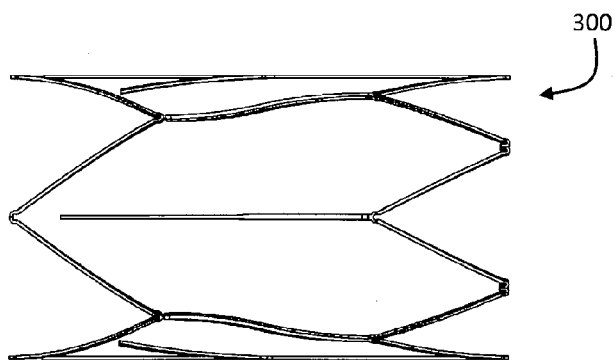
Figure 115:
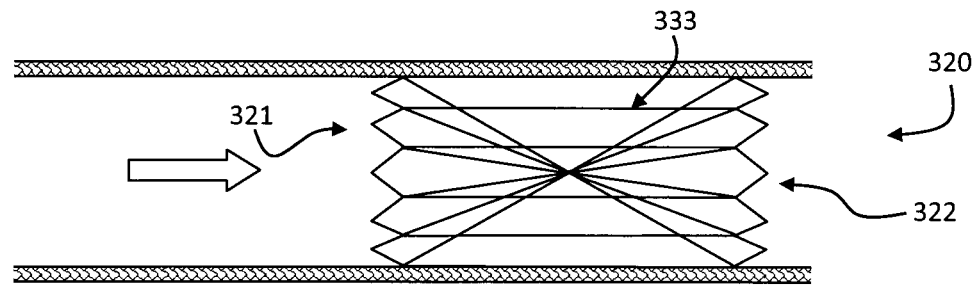
FIGS. 115 to 119 show a device having two filter cones facing in opposite directions, conversion leaving the distal cone to retain a clot.
Figure 116:
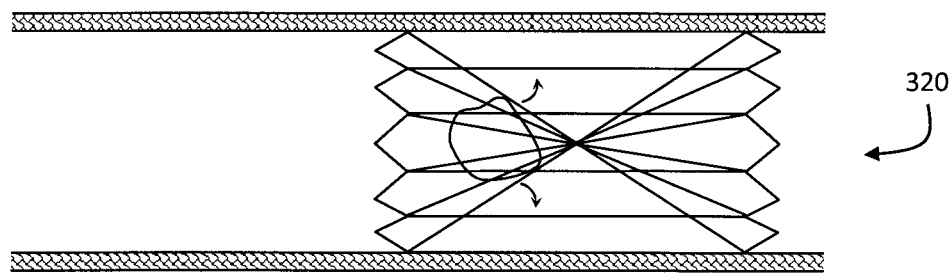
Figure 117:
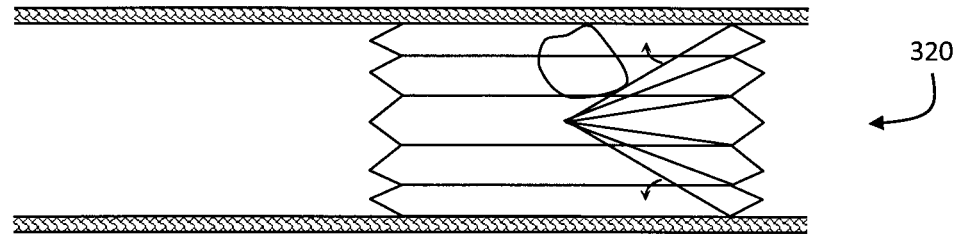
Figure 118:
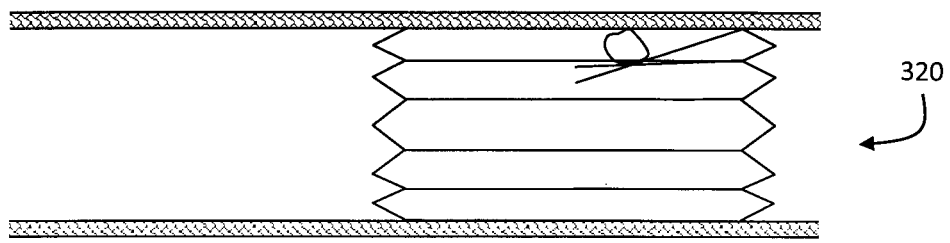
Figure 119:
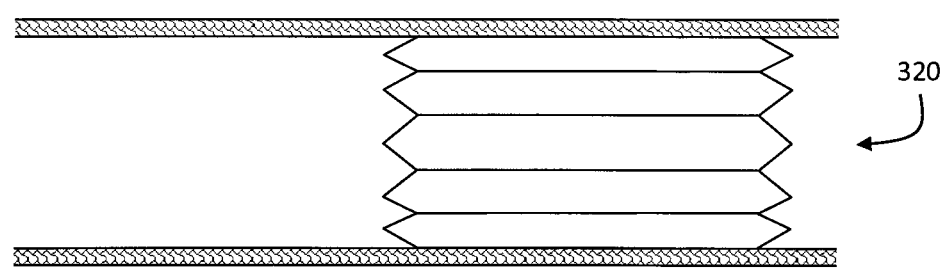
Figure 120:
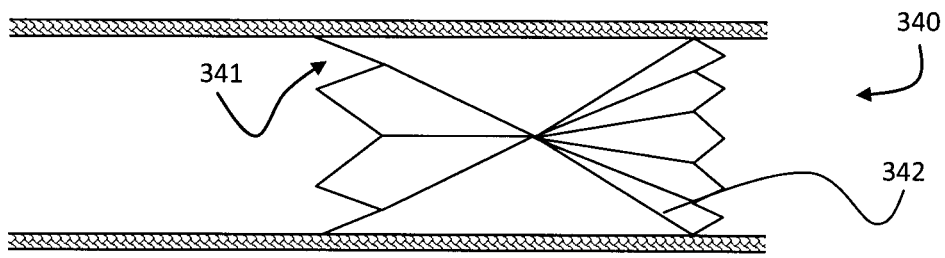
FIGS. 120 to 124 show a device having two cones, the proximal one being more coarse than the distal one.
Figure 121:
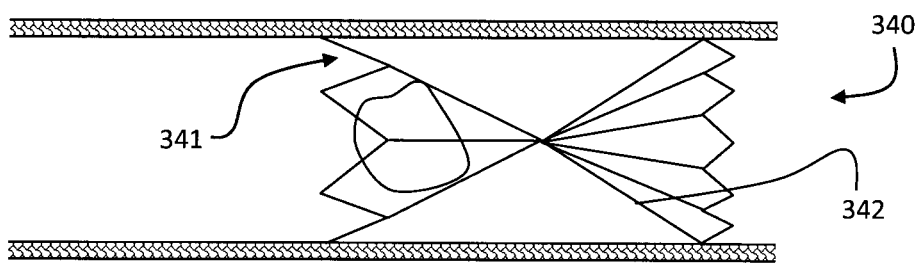
Figure 122:
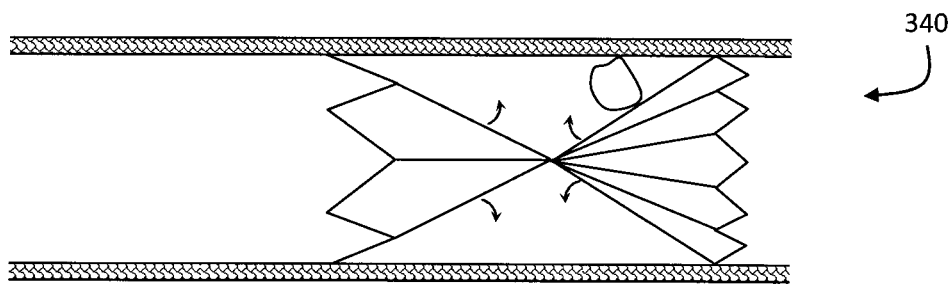
Figure 123:
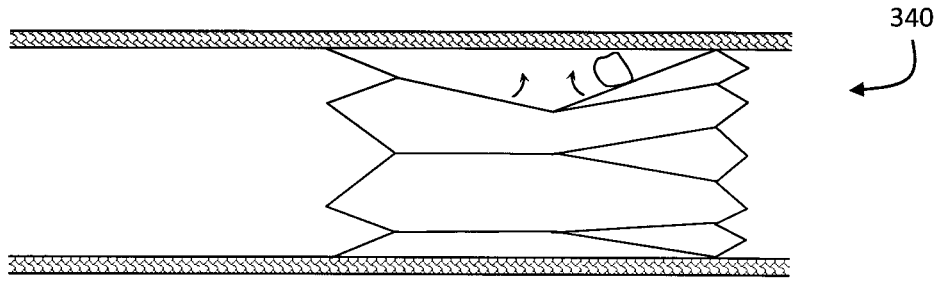
Figure 124:
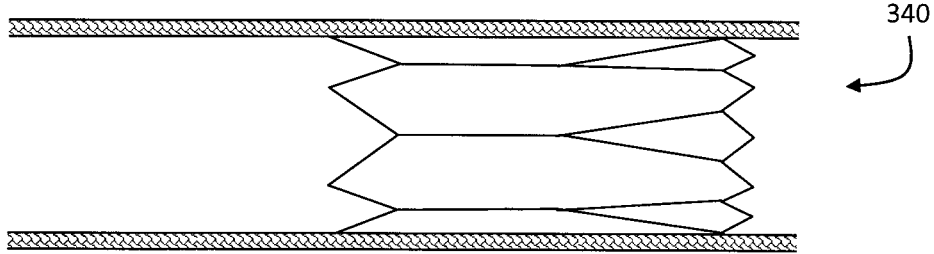

In this embodiment a filter device 120 comprises a proximal support hoop 121, a distal support hoop 122, and a longitudinal support 123 in-between. There are three looped filter elements 124-126, and three straight filter elements in this case, and they are held in the capture position by a bio-absorbable tie 130 as shown in FIG. 44. The looped filter elements are supported from the distal hoop 122 by cantilever links 129. The straight filter elements are supported from peaks of the proximal hoop 121 and extend through the looped filter elements as shown in FIG. 44. FIGS. 45 to 50 show progression from a capture position to an open position. FIGS. 51 to 54 sow how a clot C is gradually reduced in size after being captured, as the filter elements gradually open. Again, as for the previous embodiments, the radially inward forces exerted by the filter elements actively aid the clot to break down in combination with lyses as they are biased by their supports to the open position. FIG. 53 shows clearly how the presence of the clot C prevents opening of the filter members even though the protection period has elapsed. The filter device thereby avails of the force exerted towards the distal direction by the clot due to the blood flow.

An aspect of this embodiment is that the filter elements are curved radially inwardly at their ends for enhanced clot capturing by guiding it into the centre more effectively;

FIGS. 55 to 62

A filter device 140 has a proximal support hoop 141, a distal support hoop 142, and longitudinal support members in-between. Three looped filter elements 144 to 146 are supported by cantilever links from the distal hoop 142 peaks. There are three additional filter elements 150 comprising straight arms and loops on the arms.

It will be appreciated that there may be more than three or four looped filter elements, depending on intended use.

FIGS. 63 to 69

A filter device 160 has a proximal support hoop 161, a distal support hoop 162, and longitudinal support members 163 in-between. In this case the filter elements are straight, much as illustrated in the first embodiment. A biodegradable tie retains the elements 164 in the capture position for the pre-determined time. However, as for the other embodiments above if a clot is present the elements 164 remain closed to retain the clot until it has broken down to a geometry that will pass through the filter elements and it will not harm the patient.

FIGS. 71 to 78

A filter device 180 has a proximal support hoop 181, a distal support hoop 182, and longitudinal support members 183 in-between. In this case six filter elements 184 are elongate and radially curved at their ends. A biodegradable tie retains the elements 184 in the capture position for the pre-determined time. However, as for the other embodiments above if a clot is present the elements 184 remain closed to retain the clot until it has broken down to a geometry that will pass through the filter elements and it will not harm the patient. It will be appreciated that the curved direction is such as to cover a cross-sectional area offset with the cross-sectional areas covered the distal ends of the filter elements 184. Hence if a clot were to pass through the first cone formed by the filter elements 184, it is likely to be captured by the distal cone formed by the distal ends of the filter elements.

FIGS. 79 to 82

A filter device 200 has a proximal support hoop 201, a distal support hoop 202, and longitudinal support members 203 in-between. In this case six filter elements 204 are elongate and radially curved inward at their ends. A biodegradable tie retains the elements 204 in the capture position for the pre-determined time. Again, if a clot is present the elements 204 remain closed to continue to capture the clot until it has been lysed to a geometry that will pass through the filter elements and it will not harm the patient. The inward curve aids in preventing endothelial coverage during the closed position by keeping the free ends away from the vessel wall in a range of vessel diameters. Upon conversion, the elements 204 press against the vessel wall, aiding endothelial coverage.

FIGS. 83 to 90

A filter device 220 has only a distal support hoop 221, and this supports twelve filter elements 224 extending proximally. The filter elements 224 are initially straight and then are curved and angled towards their free ends. In the closed position the angled end is twisted about its axis at the apex (preferably approximately 90°), and an eyelet tying arrangement prevents unwinding. Upon conversion, the filter elements 224 unwind as they move to the open positions, and if a clot is present at conversion the unwinding aids in breaking it to accelerate lysis.

FIGS. 91 to 98

A filter device 240 has a proximal support hoop 241, a distal support hoop 242, and longitudinal support members 243 in-between. In this case six filter elements 244 are elongate and Y-shaped. A biodegradable tie retains the elements 244 in the capture position for the pre-determined time. However, as for the other embodiments above if a clot is present the elements 244 remain closed so continue to capture a clot until it has broken down to a geometry that will pass through the filter elements and it will not harm the patient. It will be appreciated that the Y-shape provides overlapping ends to achieve increased stiffness.

FIGS. 99 to 102

A filter device 260 has a proximal support hoop 261, a distal support hoop 262, and longitudinal support members 263 in-between. In this case two filter elements 264 are elongate and forked. The proximal support hoop has four proximal and four distal peaks whereas the distal support hoop has six proximal and distal peaks. This provides additional space for the forked filter element to rest unobstructed (to prevent fretting corrosion) in the open state while keeping all distal peaks of the proximal support connected to the distal support frame. A biodegradable tie retains the elements 264 in the capture position for the pre-determined time. However, as for the other embodiments above, if a clot is present the elements 264 remain closed to retain a clot until it has broken down sufficiently. One or multiple filter elements may be supplied. Filter element forks may have two, three, or more prongs. Forked prongs are radially curved for unobstructed blood flow in the open state and may be axially curved to vary clot capture efficiency.

FIGS. 103 to 106

A filter device 280 has a proximal support hoop 281, a distal support hoop 282, and longitudinal support members 283 in-between. Again, the proximal support hoop has fewer peaks than the distal support hoop. Four filter elements 284 are elongate and forked, and additionally include a spur 285 extending, in the closed position, radially inwardly and proximally. A biodegradable tie retains the elements 284 in the capture position for the pre-determined time, and again if a clot is present the elements 284 remain closed to retain a clot until it has broken down sufficiently.

FIGS. 107 to 114

A filter device 300 has a proximal support hoop 301, a distal support hoop 302, and longitudinal support members 303 in-between. Again, the proximal support hoop has fewer peaks than the distal support hoop. Two filter elements 304 are elongate and forked, and two filter elements 305 are straight. A biodegradable tie retains the elements 304 and 305 in the closed position for the pre-determined time, and again if a clot is present the elements 304 and 305 remain closed to retain a clot until it has broken down sufficiently. This combination of filter elements achieves an excellent compromise between enhanced filter coverage and reliable opening.

FIGS. 115 to 119

In a device 320 there are two sets of filter elements, proximal 321 and distal 322. The proximal filter elements 321 extend from the proximal end of a support 333 to the centre of the vessel where they are releasably coupled to form a proximal cone. The distal filter elements 322 extend from the distal end of the support 333 to the centre of the vessel where they are releasably coupled to form a second, distal, cone. The proximal cone 321 holds the clot in the centre of the vessel, for the protection period, where lysis is optimal. It converts first, and after an additional period of time, the distal cone 322 converts. If a clot is present as the proximal cone 321 converts, it moves to the annular region formed by the distal cone 322 at the vessel wall. If the clot is still present as the distal cone 322 converts, the filter elements hold it at the vessel wall until lysis has completed.

FIGS. 120 to 124

A filter device 340 has two conical sets 341 and 342 of filter elements facing each other. The elements 342 are V-shaped. The proximal set 341 extends from a proximal hoop of a support 343 to the apex of the cone where they are attached to the elements 342 that extend distally to one or two points on the distal support hoop. The proximal and distal filter elements may be formed integrally or attached with a biodegradable restraint. There may be one element proximally for every distal element. This provides two-stage filtration where the first stage captures a large clot and the second stage captures smaller clots. Alternatively there may be two proximal elements for every V-shaped distal element to provide similar capture efficiency proximally and distally. The distal V-shaped elements aid retention of a clot against the vessel wall upon conversion.

FIGS. 125 to 138

A filter device 360 has a proximal support hoop 361, a distal support hoop 362, and longitudinal support links 363. Two filter elements 364 extend from the proximal support hoop 361, and each element 364 comprises a first filter strut 365, a first hinge 366, a second filter strut 367, a second hinge 368, a stabilising strut 369, and an eyelet 370. To assemble the device 360 to a closed position, the second filter strut 367 is pulled past a central axis forming a bend at the first hinge 366 and the stabilising strut 369 is bent back to a centre line forming an opposing bend at the second hinge 368. Holding in position, the same is done for the remaining filter elements 364 and a bio-degradable tie is threaded through the eyelets 370 to hold them in position. This forms two cones pointing in the same direction. The proximal cone is clot-releasing and the distal cone is clot retaining. If a clot is present upon conversion, the stabilising strut 369 snaps back in line with the second filter strut thereby releasing the clot from the clot-releasing cone. After this, the clot becomes trapped between the first filter strut 365 and the second filter strut 367 (in the clot-retaining cone). The filter elements trap the clot until lysis is complete. FIGS. 129 to 132 show all filter elements in the closed state. FIGS. 133 to 136 show only one filter element in the closed state for illustrative purposes only.

Figure 137:
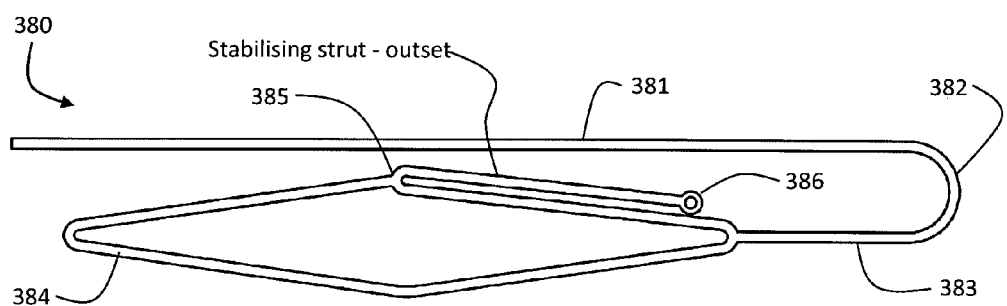
Figure 138:
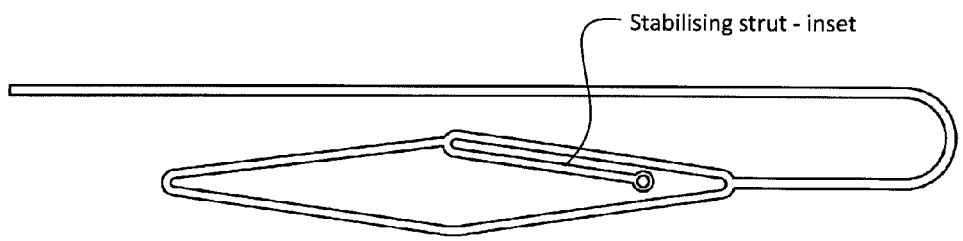
Figure 139:
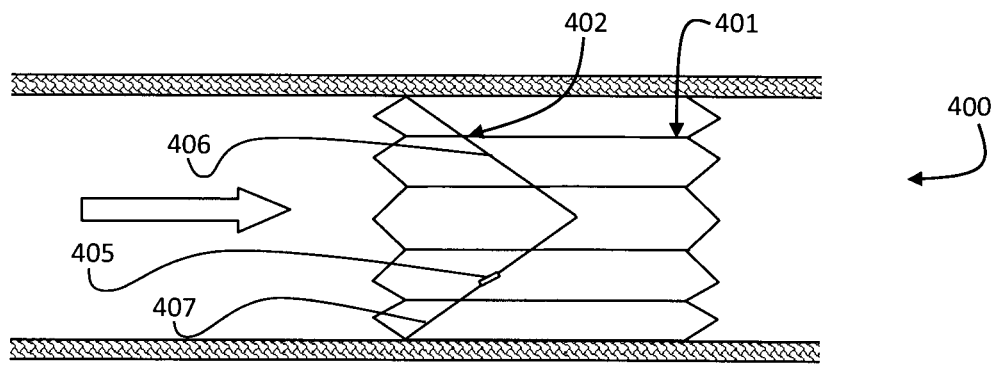
FIGS. 139 to 142 show a device with a clot-retaining clasp arrangement.

In a variation of this embodiment, shown in FIGS. 137 and 138, a filter element 380 has a first filter strut 381, a first hinge 382, a second filter strut 383, a filter cell 384, a second hinge 385, and an eyelet 386. In this embodiment, the array of cells interlock. The first cell fits inside a second larger cell, this assembly fitting inside a third, larger, cell. Each assembly fits inside the next largest cell until all cells are interlocked. The stabilising struts are then manipulated to meet at a central location where they are tied with a bio-degradable suture to prevent the cells from opening until a predetermined period of time has elapsed. Each cell may have a different size or form so that it will fit into the next cell. Preferably, the device has an even number of elements 380, the two smallest opposing each other, and the next two sizes opposing each other and so on. For each opposing pair one filter element may have an inset stabilising strut and the other an outset strut. This will aid reliable opening. Alternatively, for filters with six or more filter elements the three smallest cells can be arranged so that they are circularly equidistant. Pairing in doubles or triples ensures a centered conversion that keeps the clot in a central location for optimum lysis. It is also possible to arrange them in any other suitable configuration.

FIGS. 139 to 142

A filter device 400 comprises a support 401 with a proximal support hoop at the proximal end of the filter, a distal support hoop at the distal end of the filter, and a plurality of support struts extending between the proximal support hoop and the distal support hoop.

The filter device 400 comprises a plurality of filter elements 402 for capturing thrombus passing through the inferior vena cava. Each element 402 is formed integrally with the proximal support hoop.

Figure 140:
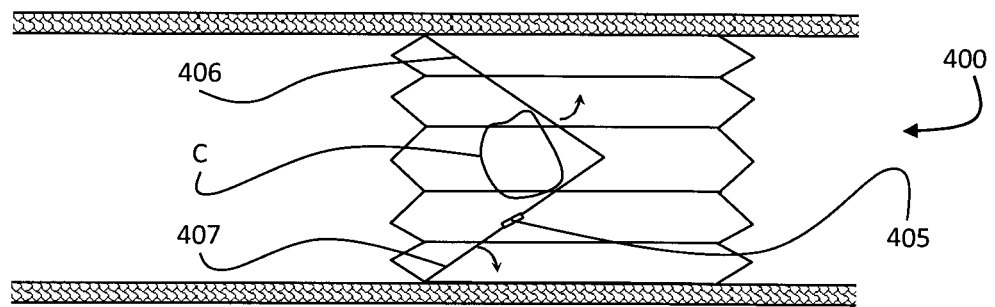
Figure 141:
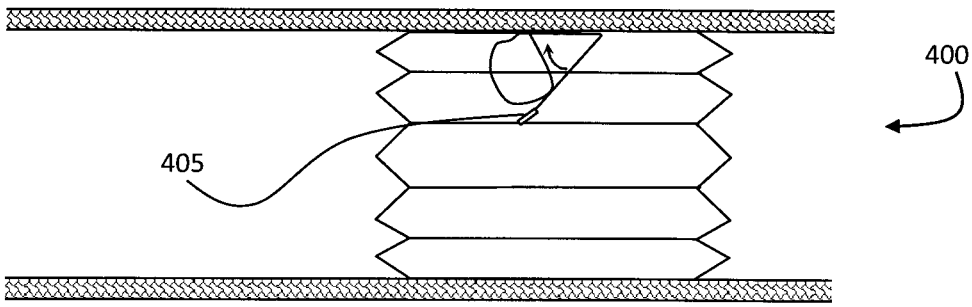

The elements 402 are movable from the capturing state (FIG. 139) to the open state (FIG. 142) upon elapse of the predetermined period of time. In the capturing state the elements are positioned to capture thrombus passing through the inferior vena cava towards the heart and the lungs (FIG. 140). In the open state the elements are configured to facilitate unrestricted blood flow.

In the capturing state the elements extend in a substantially straight line to an apex. In this manner the elements 402 define a generally conically shaped capture region within which thrombus may be captured. When the filter is deployed in the inferior vena cava, the apex is substantially in-line with the longitudinal axis extending through the centre of the inferior vena cava, and the capture region is located in the region of the centre of the inferior vena cava. When the filter is deployed in the inferior vena cava, the capture arms extend in the direction of blood flow through the inferior vena cava.

The distal end of the distal support hoop is located distally of the capture arms and the apex, and the proximal end of the proximal support hoop is located proximally of the capture arms.

The capture arms are movable from the capturing state to the open state upon elapse of the predetermined period of time. The capture arms are biased towards the open state.

The filter comprises a holder (not shown) at the distal ends of the elements 402 to temporarily hold them in the capturing state until elapse of the predetermined period of time. The holder engages with each elements to hold it in the capturing state. The holder is biodegradable and/or bioabsorbable upon elapse of the predetermined period of time. Upon biodegrading/bioabsorbing of the holder, the elements are free to move from the capturing state to the open state. The elements are not biodegradable or bioabsorbable.

The filter is movable between a collapsed delivery state and an expanded deployed configuration. The filter is biased radially outwardly towards the deployed configuration. When the filter is deployed in the inferior vena cava, the support hoops exert a force radially outwardly on the internal wall of the inferior vena cava. In this manner the support hoops support the capture arms in position relative to the wall of the inferior vena cava.

In the event of thrombus passing through the inferior vena cava towards the heart and the lungs, the thrombus will be captured in the capture region of the filter (FIG. 140). The thrombus will thus be prevented from passing into the heart and the lungs which could otherwise lead to pulmonary embolism. The captured thrombus will gradually be broken down through lyses into smaller clinically insignificant particles.

Figure 142:
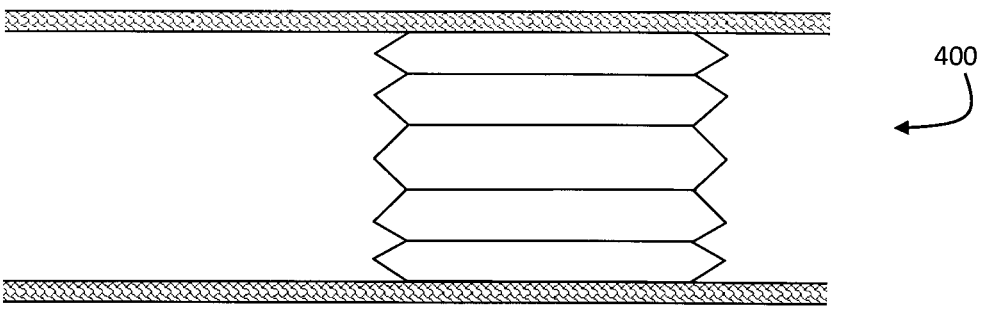
Figure 143:
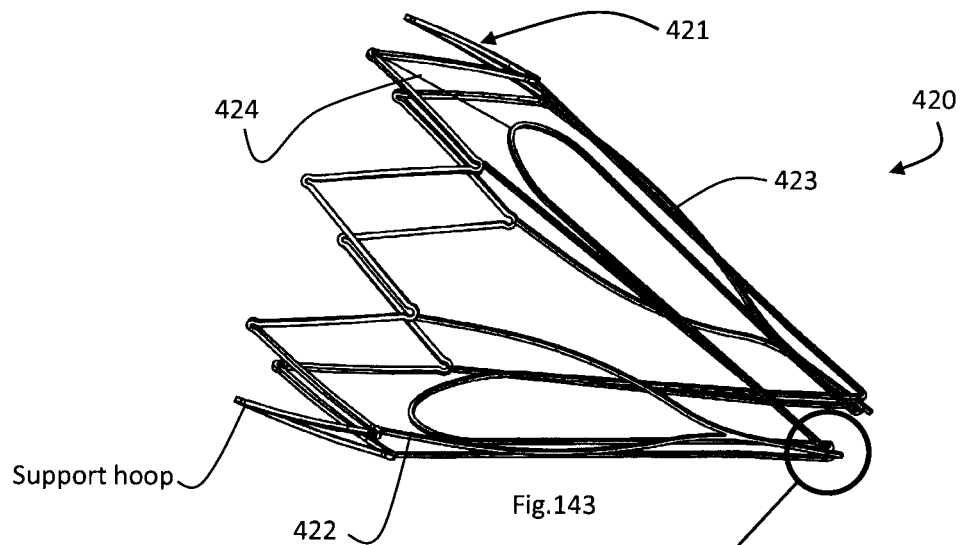
FIGS. 143 to 150 show a clasp arrangement with looped filter elements.
Figure 144:
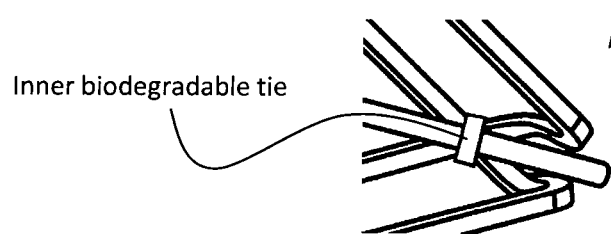
Figure 145:
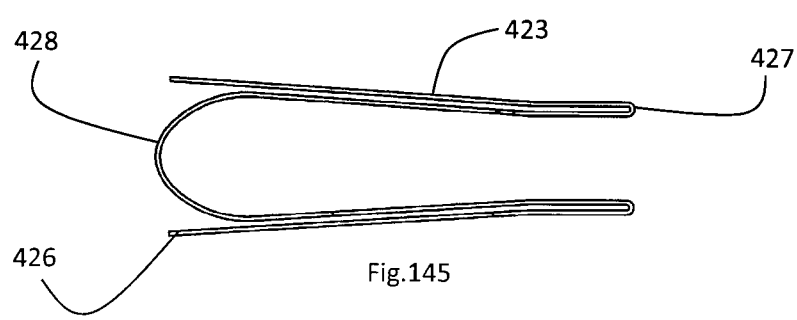
Figure 146:
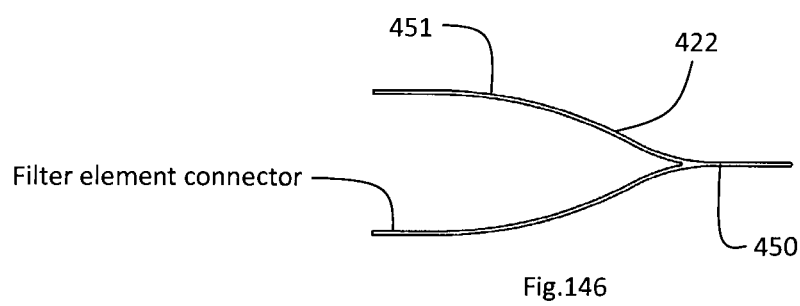

The holder member temporarily holds the filter elements in the capturing state until elapse of the predetermined period of time. Upon elapse of the predetermined period of time the holder biodegrades/bioabsorbs. This enables the elements to move from the capturing state to the open state (FIG. 142). In the open state the filter facilitates unrestricted blood flow. The support hoops and the filter elements remain in the inferior vena cava (FIG. 142).

In addition, the conical filter formed by the arms 402 is provided with clot rention features. A biodegradable coupler 405 couples an L-shaped capture arm 406 to an opposing capture arm 407. Upon biodegradation, both filter elements return to the vessel wall. The L-shaped capture arm 406 retains the clot if present and applies a compressive force to aid clot lysis. Note that, for clarity, only top and bottom opposing filter elements are shown. This action of retaining a clot after degradation of the coupler 506 may be referred to as clasping.

In common with the above embodiments this filter device opens after a time period determined by the bio-degradation of the holder (in this case the coupler 405) and also continues to retain a clot if present. In the embodiments of FIGS. 1 to 138 a proximal cone remains because of the clot, and gradually reduces in size as the clot lyses. In this embodiment a "clasp" remains because of the L-shaped configuration of the filter element 406.

FIGS. 143 to 150

Figure 147:
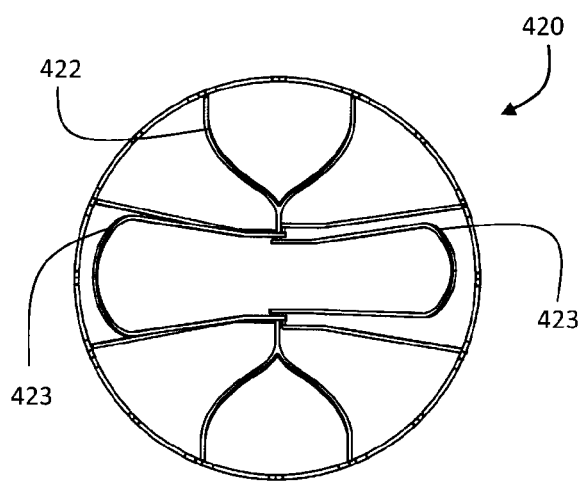
Figure 148:
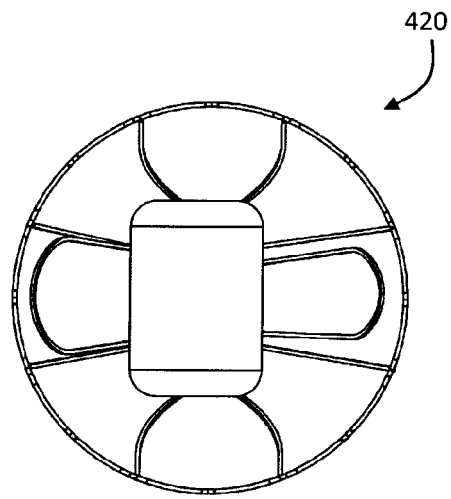
Figure 149:
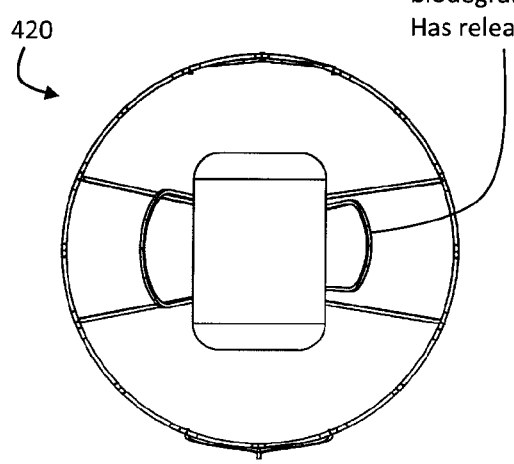
Figure 150:
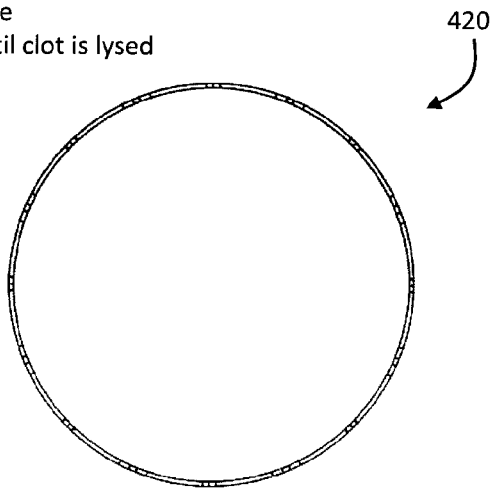
Figure 151:
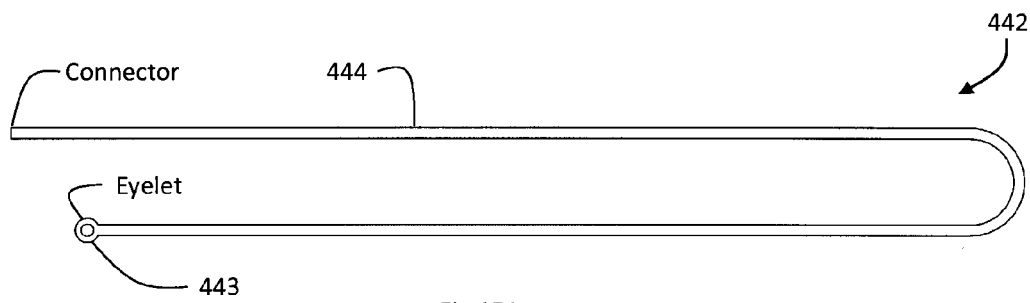
FIGS. 151 to 157(a) show various filter elements for clasp filter devices, and FIGS. 157 (b) to (j) show a device incorporating the filter element of FIG. 157(a)
Figure 152:
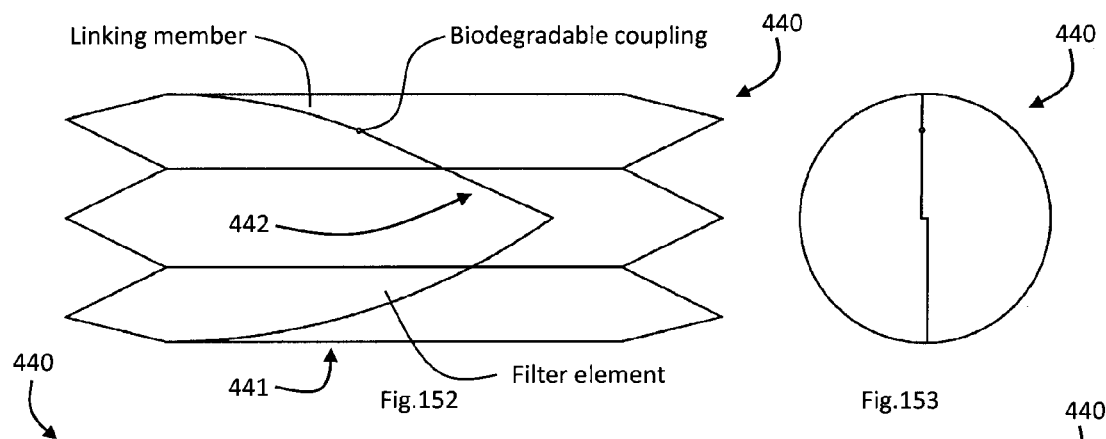
Figure 153:
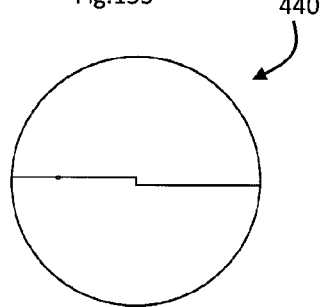
Figure 154:
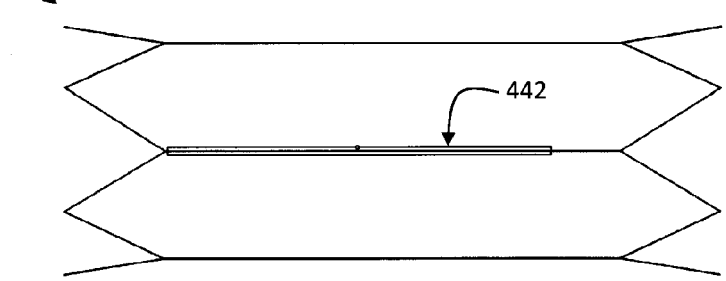
Figure 155:
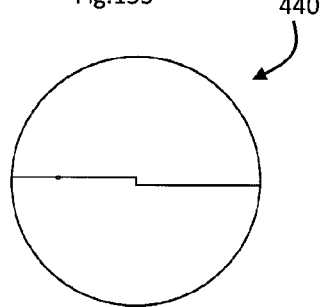

A filter device 420 comprises a proximal support hoop 421 from which extend filter elements 422 and clasps 423. Each clasp 423 comprises a clasp connector 426 a clasp hinge 427 and a clasp tip 428. Each filter element 422 comprises a tip 450 and forked elements 451, the proximal ends of which are connected to the hoop 421. As shown in FIG. 147, although the clasps are given the same numerals, one is actually slightly smaller than the other. The clasp connectors are formed integrally with the hoop. To assemble the device the large clasp tip is pulled across the central axis of the support ring and held in place with a bio-degradable tie that connects the clasp tip to the hoop 421. The small clasp 423 is pulled through the large clasp, across the central axis, and tied to the hoop 421 with a bio-degradable filament. The filter element 422 tips 450 are tied to the nearest clasp hinge 427. In an alternative embodiment eyelets and pin holders may alternatively be used. Also, there may additionally be a distal support hoop, preferably connected by longitudinal struts.

As shown in FIGS. 147 to 150 if a clot is present when the pre-determined protection has elapsed, the clasps will lock onto the clot and will not return to the vessel wall until the clot has lysed. The clasps may curve radially inwardly as they near the vessel wall, thus preventing endothelial coverage during the capturing position while providing improved grip when retaining a clot post conversion.

FIGS. 151 to 155

Referring to FIGS. 151 to 155, a filter device 440 comprises a stent-like support 441 with proximal and distal hoops and intermediate struts. Filter elements 442 have a U-shaped configuration with an eyelet 443 and a connector 444. The connector 444 is connected to the support 441 at the proximal hoop, but it could alternatively be at a strut, the distal hoop, or a longitudinal connector. The eyelet 443 is pulled across the diameter of the device and is tied to the support 441 by a length of biodegradable suture. Alternatively a linking member may be provided that extends from the support 441 at an opposing side to each filter element, each linking member being coupled to the filter element with a biodegradable holder such as a tie a pin or a cap. The holder member may be positioned out of flow at the vessel wall. The linking member may extend from either proximal or distal peaks of either hoop or from the struts, or indeed from connection points between any parts of the support. Also, the linking member may extend in zigzag configuration from one straight connector to the next.

Figure 156:
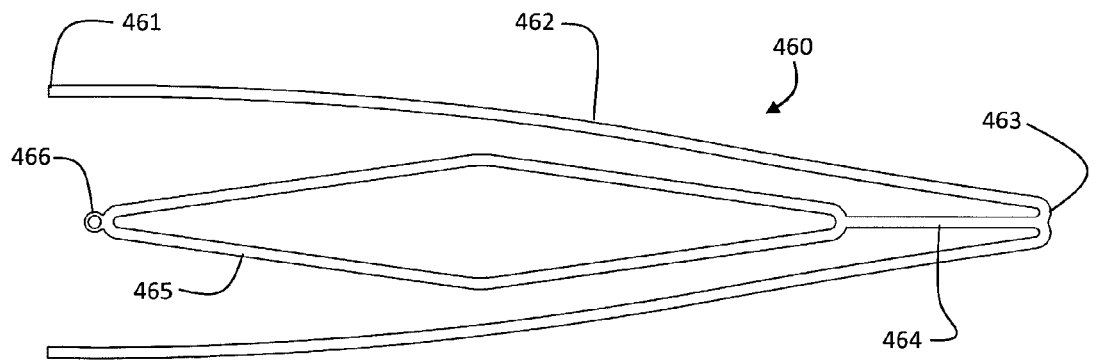
Figure 157A:
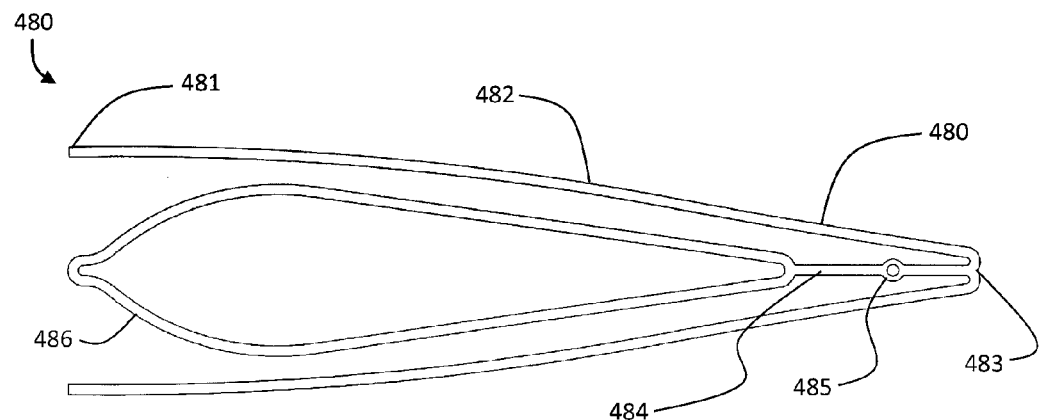
Figure 157B:
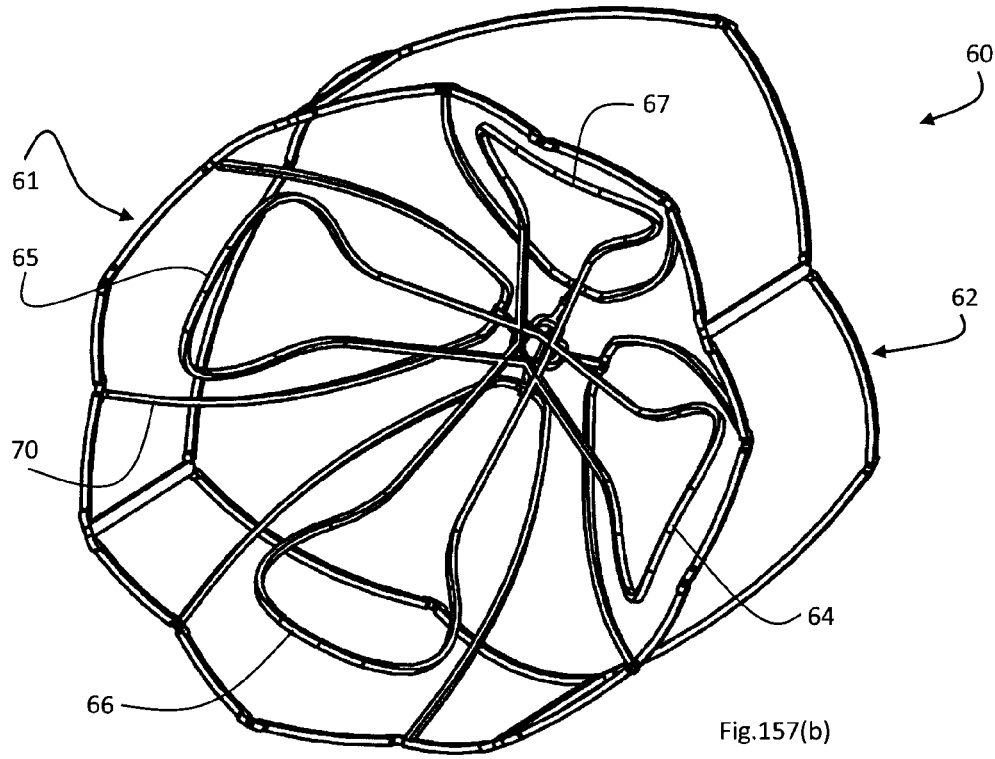
Figure 157C:
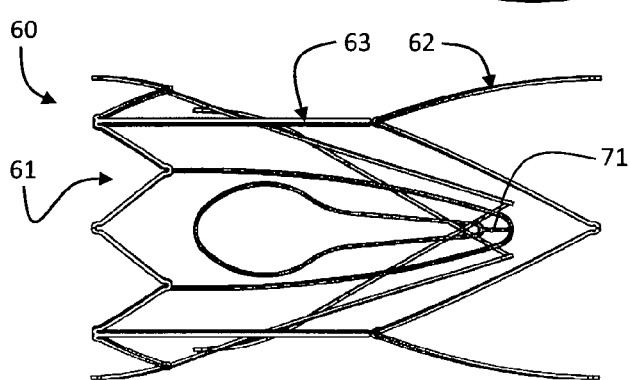
Figure 157D:
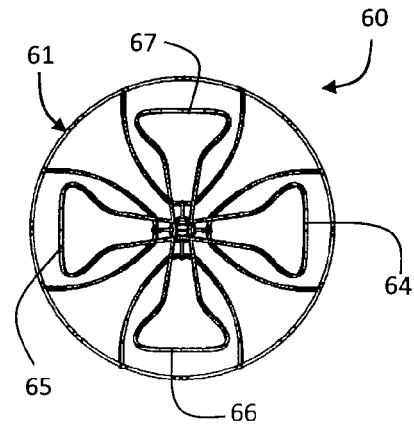
Figure 157E:
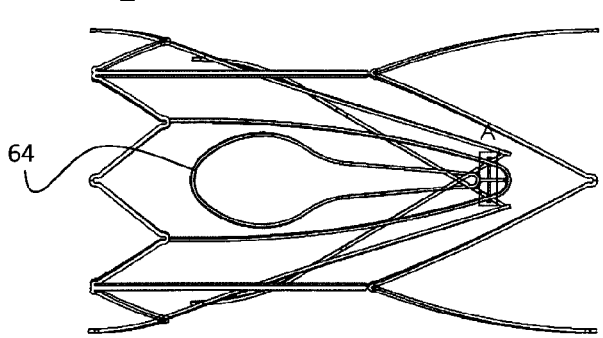
Figure 157F:
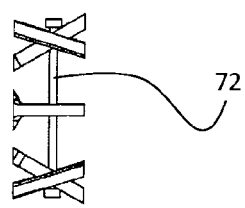
Figure 157G:
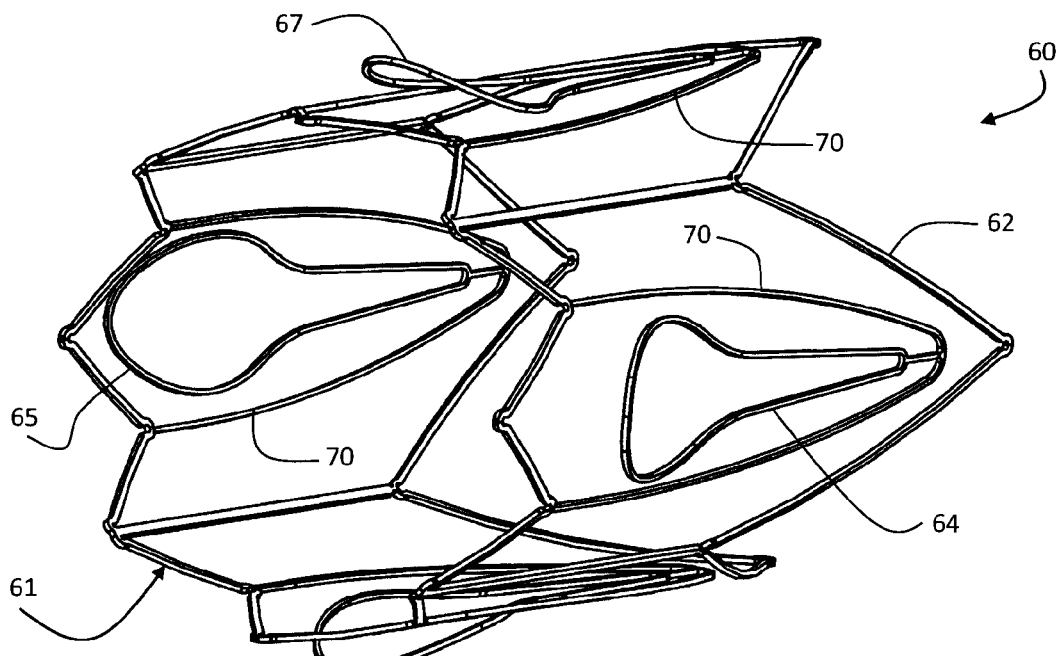
Figures 157H, 157I:
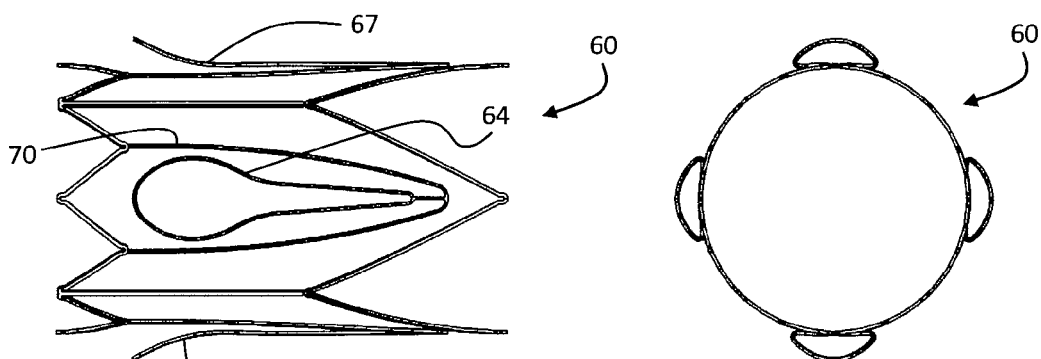
Figure 157J:
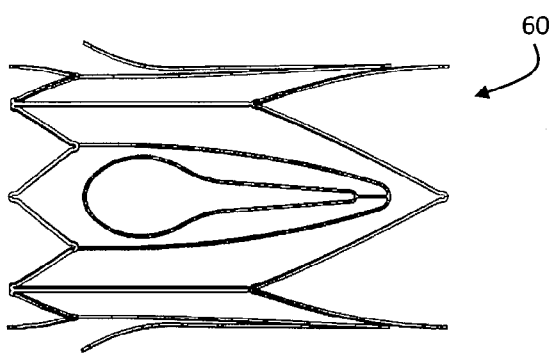
Figure 158:
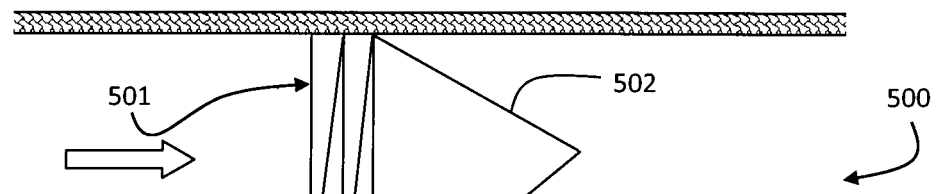
FIGS. 158 to 161 show a filter device with a proximal helical support coil extending into a centrally hinged loop with a filtration screen.
Figure 159:
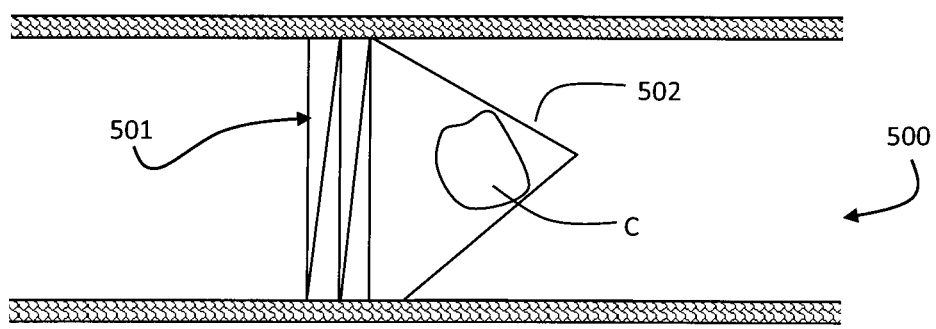
Figure 160:
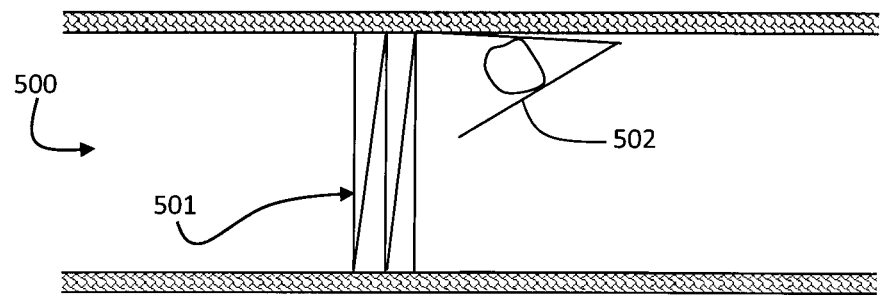
Figure 161:
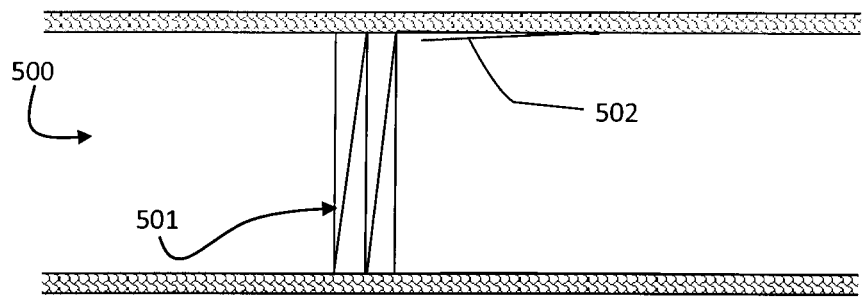
Figure 162:
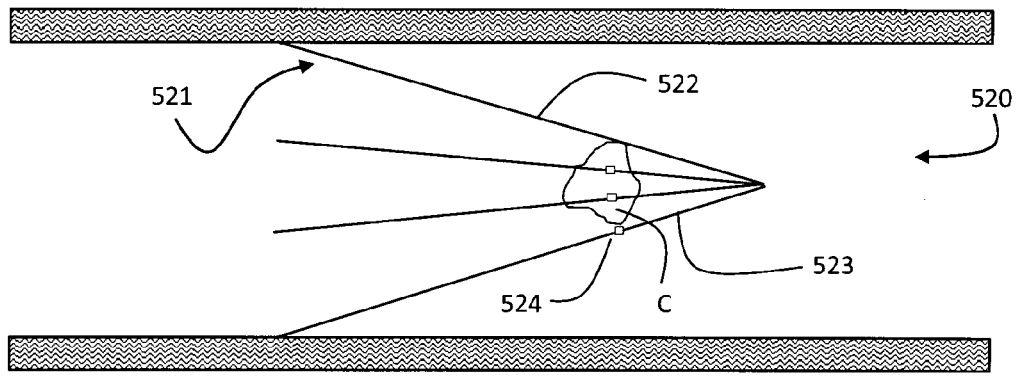
FIGS. 162 to 167 show a filter device with a conical reception space and a mini cone which is at the vessel wall post-conversion.
Figure 163:
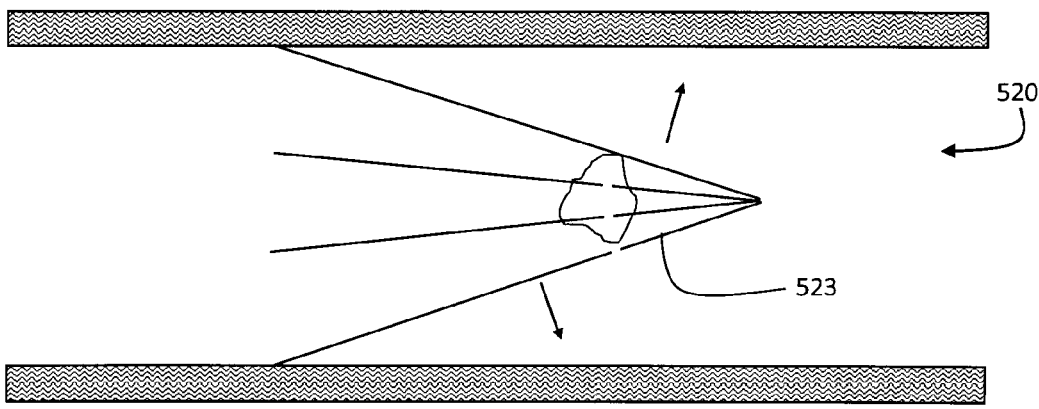
Figure 164:
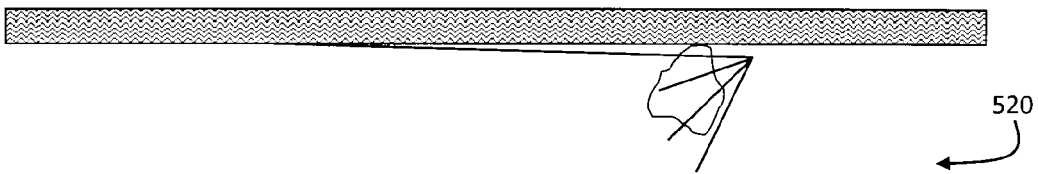

FIGS. 156 and 157(a) to 157 (j)

FIGS. 156 and 157(a) show two alternative filter elements, 460 and 480. The element 460 comprises a connector 461, a stabilising strut 462, a hinge 463, a cell connector 464, a filter cell 465, and may include a hoop tip eyelet 466. The element 480 comprises a connector 481, a stabilising strut 482, a hinge 483, a cell connector 484, an eyelet 485, and a filter cell 486.

In these embodiments the cell provides additional stiffness. For a three-cell filter, a first cell fits inside a second larger cell, and this assembly fits inside a third larger cell. For additional cells, each assembly fits inside the next largest cell until all cells are interlocked. Filters with an even number of filter elements can be arranged so that they are in opposing pairs for balanced inter-locking as in above four-loop embodiments. To assemble a filter incorporating filter element 460 in the closed state, the cells are interlocked as described above and each cell tip is connected to a linking member that extends from the support frame at the opposite side of the vessel by means of a biodegradable tie. The linking member and filter cell tip may be provided with eyelets to facilitate use of a biodegradable pin. The linking members can be straight or V-shaped and may extend proximally or distally, preferably a straight linking member extends distally from a proximal peak of a proximal crown—where the filter element extends from two distal peaks of the proximal crown at the opposite side of the vessel Alternatively, lengths of suture can be used to tie the cell tips to the support frame without the use of a linking member. As each cell tip is tied independently of each other, each tie can be provided with the same degradation period or with individual degradation periods. It is advantageous to keep the cell tips at a distance from the vessel wall during use to prevent endothelial encapsulation which may hinder conversion to the open state, the linking member or length of suture achieve this. For a four-cell filter, only two opposing filter elements need to be secured in order to keep all four cells in the closed state. Similarly, for a six cell filter, only three equidistant cells need to be secured in order to keep all six cells in the closed state. To assemble a filter incorporating the filter element 480 in the closed state, the cells are interlocked as described above and a minimum of two cells are releasably secured together with a biodegradable/biostable loop, pin, or cap. Preferably, eyelets or tie retention means are provided on the cell connectors. A biodegradable tie in the form of a pin or loop then couples the two eyelets which hold the filter elements in place. Three, four, or more filter elements may be provided as described above. Only two opposing filter elements need to be secured where four filter elements are provided, preferably the two most proximal facing cells are connected using eyelets on the cell connectors. Once the two opposing cells of a four cell filter are secured, the remaining elements will also be secure. For devices with six or more filter elements the three smallest cells can be arranged so that they are circularly equidistant. In this case, only three equidistant cells need to be secured together. Pairing in doubles or triples ensures a centered conversion that keeps the clot in a central location for optimum lysis. It is also possible to secure all cells and to arrange the cells in other configurations to achieve reliable opening. One single clasp or moving part can be used to provide filtration.

FIGS. 157(b) to 157(j) show a filter device 60 comprising a proximal support hoop with eight peaks and a distal support hoop 62 with only four peaks, interconnected by longitudinal support members 63 along the vessel wall. In this embodiment there are also four looped filter elements, 64, 65, 66, and 67 which are very similar to the element 480. In this case the filter elements are supported from the proximal hoop 61, via support loops 70 which extend from distal peals of the proximal hoop 61. The support loops 70 are connected to the respective loop by a link 71 which extends from the distal end of the support loop 70. The loops are interconnected to provide the capture position. The loops are retained in the capture position by a pin 72, shown in FIG. 157(d).

In a variation using the filter element 460, the holder member is in the form of flexible ties which extend distally from different positions on the proximal support hoop to at least two filter element loops. The eyelet of the filter element 460 may be used for this. This is sufficient to retain all of the four loops in the capture position.

Alternatively a holder connecting link which is not biodegradable may extend from the support and be connected to a filter element loop at an eyelet by a biodegradable pin or tie. The link may also have an eyelet.

Figure 15:
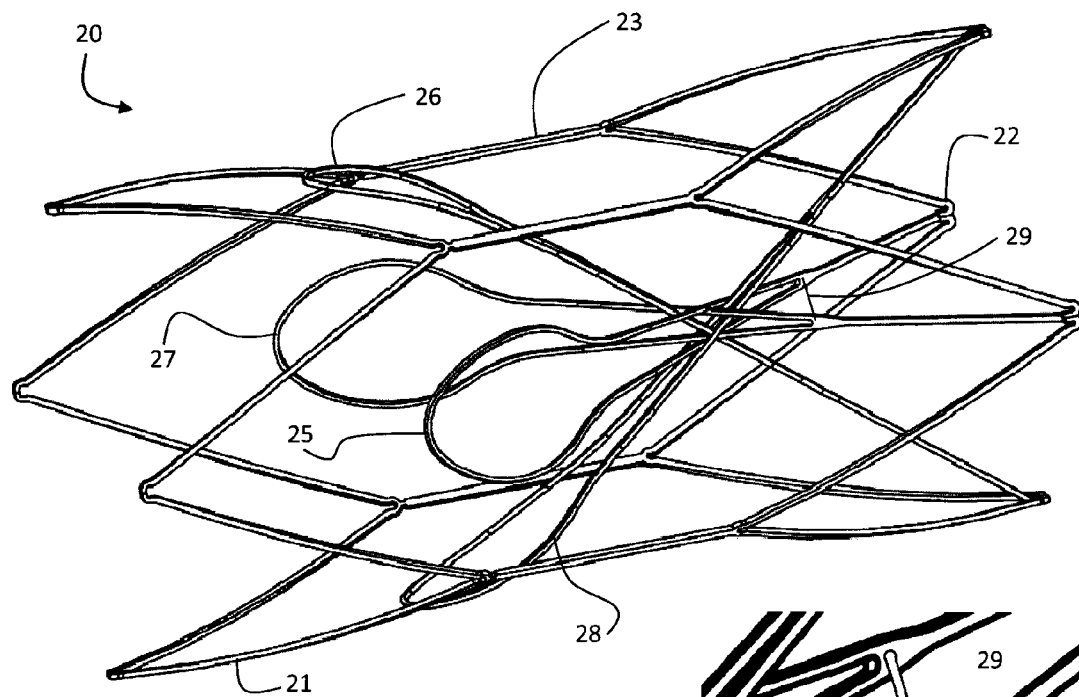
Figure 16:
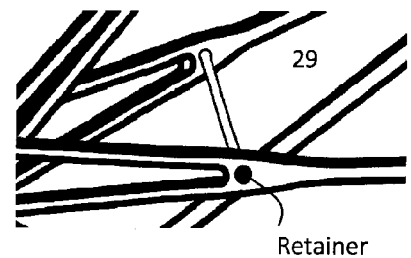
Figure 17:
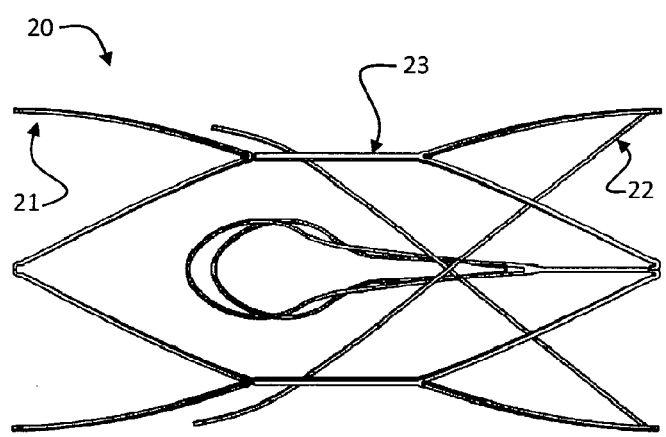
Figure 18:
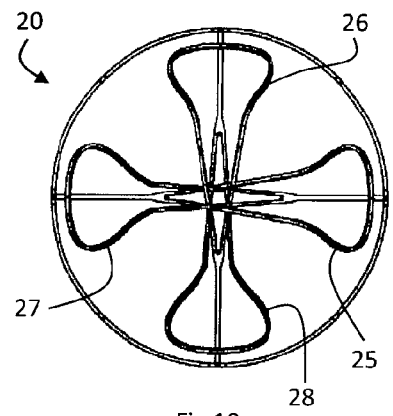
Figure 26:
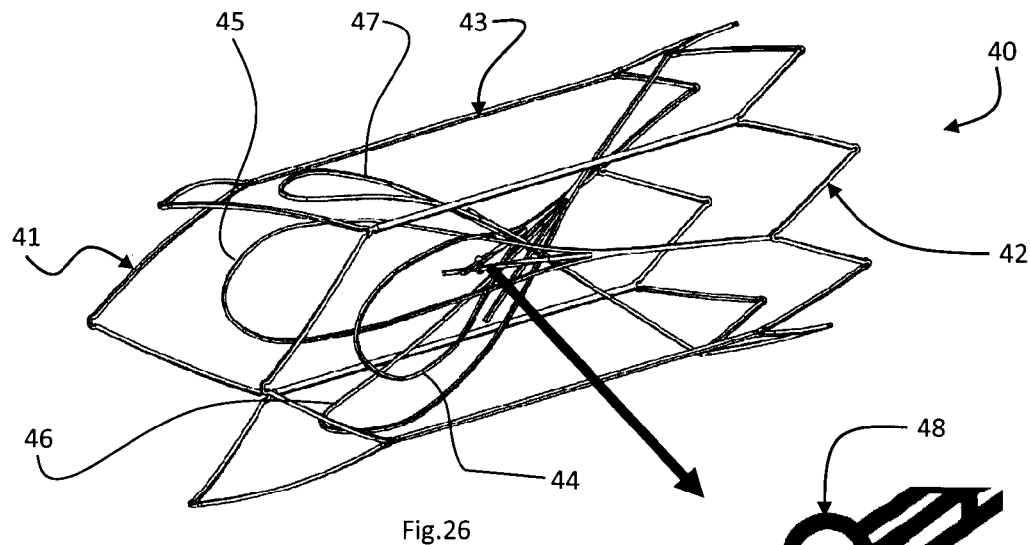
Figure 27:
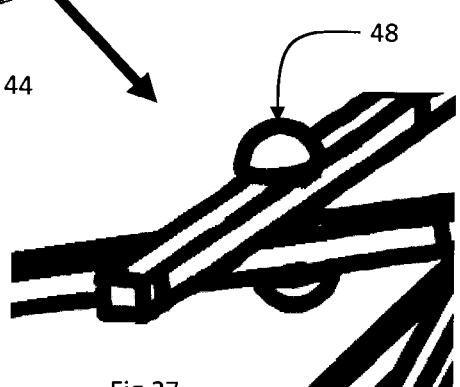

An advantage of a filter device incorporating a proximal and distal support frame with either of the filter elements 460 or 480 over the loop filter elements of FIG. 15 is that it provides a reduced parking space within the implantation site.

FIGS. 158 to 161

A filter device 500 is provided with a proximal helical support coil 501 extending into a centrally hinged loop 502 with a filtration screen. A free end of the loop is releasably attached to the proximal helical support. Upon release of the screen, a clot if present is trapped between the two halves of the filtration loop until lysis is complete. Resilience of the screen 502 causes it to be biased towards the closed position shown in FIG. 161, thus actively breaking down the clot. It is also possible to have the filtration loop extending from a proximal hoop or even between proximal and distal support hoops connected with longitudinal support members. The loop and filtration screen may have a curved surface so that it does not obstruct the flow in the open state. Alternatively, each half of the loop may be formed into a sinusoid pattern so that a filtration screen is not needed.

FIGS. 162 to 167

Figure 165:
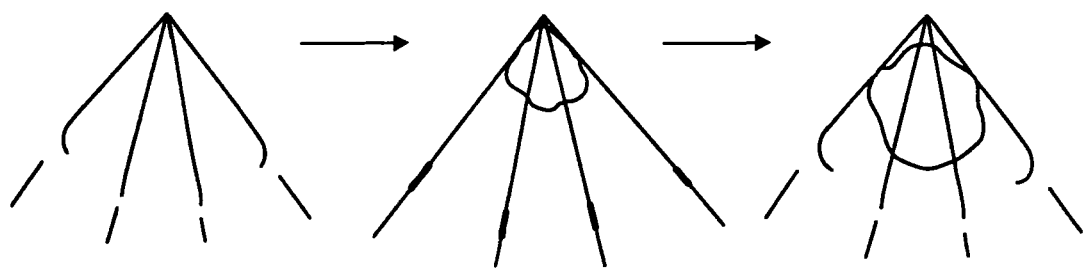

A filter device 520 is provided with a conical reception space. One filter element, 522, extends to an apex where it is attached to a portion of the remaining filter elements 523. The arms 523 have a bio-degradable holder member 524 and so the distal ends of these arms form a mini cone after the holder members 524 degrade. Upon biodegradation, the capture arms 523 move to the vessel wall, where they are held in position by the arm 522. A clot if present is retained in the mini cone at the vessel wall. It is appreciated that shape memory may be provided so that the mini cone moves to lie against the wall when the clot is completely lysed. This action is shown in FIG. 165.

Figure 166:
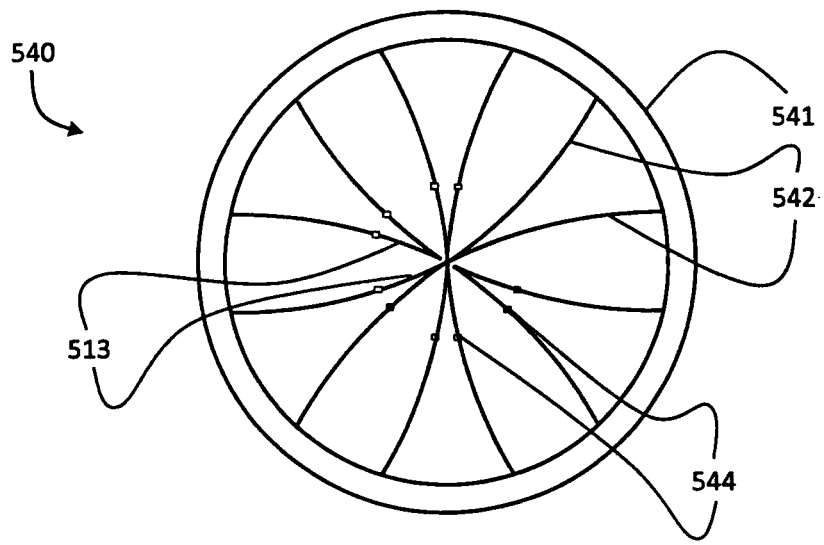
Figure 167:
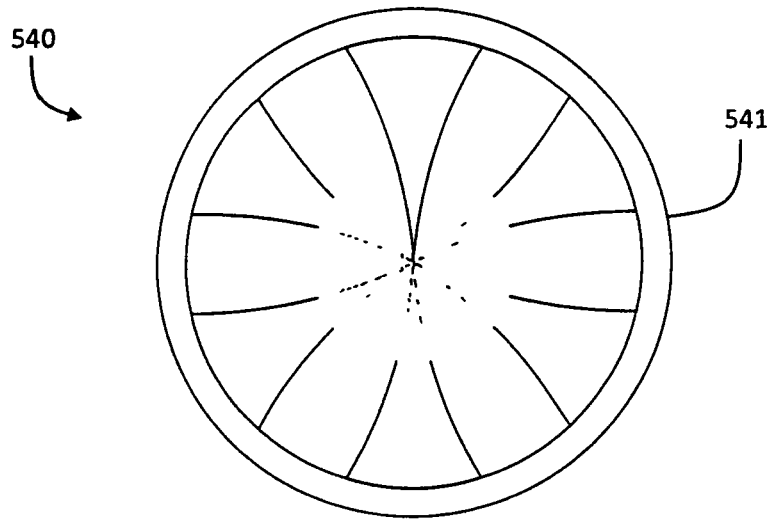
Figure 168:
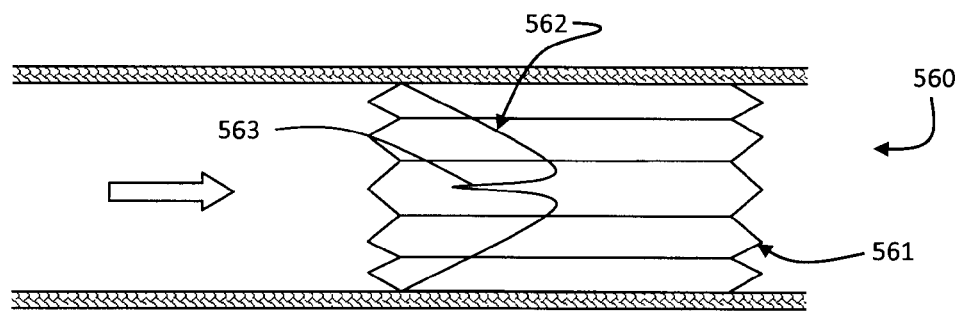
FIGS. 168 to 172 show a device with a stent-like support and an M-shaped filter.
Figure 169:
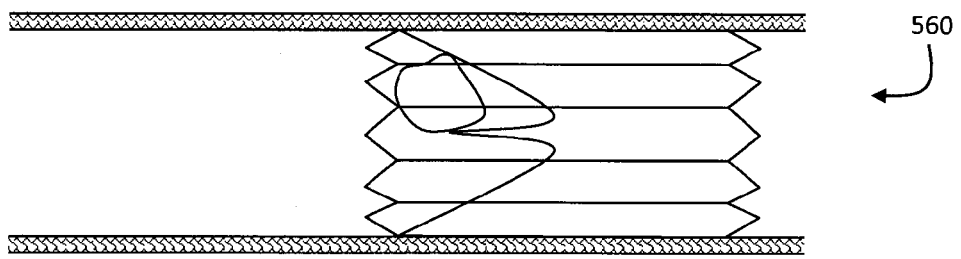
Figure 170:
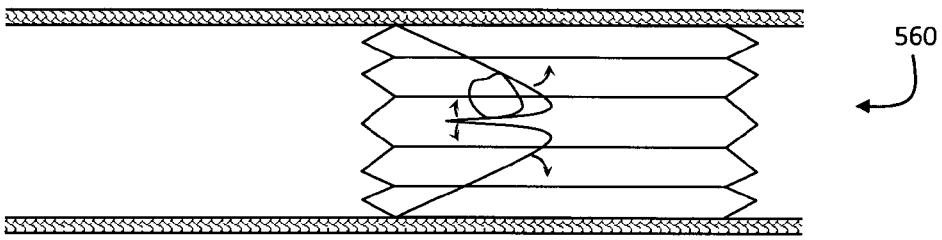
Figure 171:
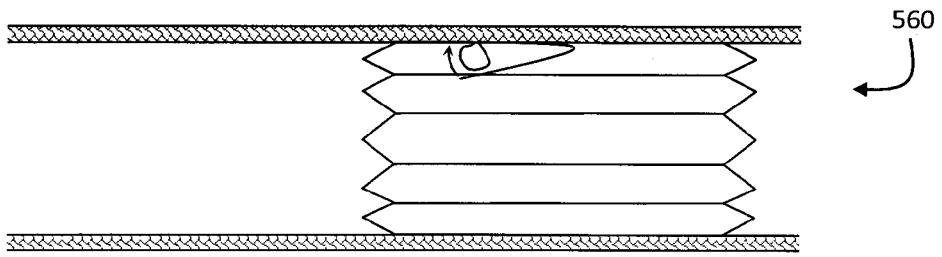
Figure 172:
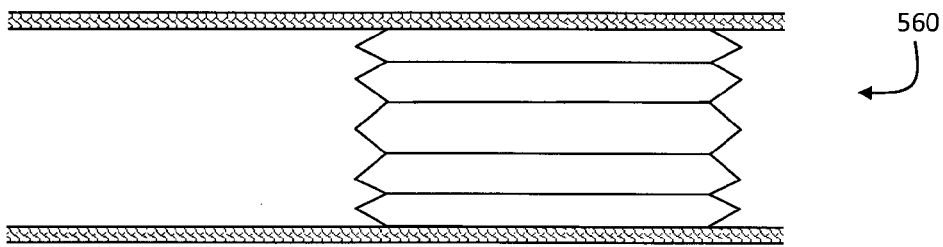

FIGS. 166 and 167 show an axial view of a variation in which there is a proximal support ring 541 in a device 540. There is one complete V-shaped arm 542 and five arms 543 with biodegradable holder members 544.

FIGS. 168 to 172

A filter 560 comprises a stent-like support 561 and an M-shaped filter 562, the elements of which extend distally inwardly from the proximal ends of the support 561 and turn to extend proximally to an apex 563 located in the centre of the vessel where they are releasably coupled. This forms an annular region where a clot is captured. Upon conversion, the filter elements carry a clot if present to the vessel wall until lysis is complete. Note that only the top and bottom filter elements are shown in the vessel view.

In this embodiment, the clasp extends all of the way around the vessel in an annular configuration, thus providing particularly effective clot retention.

Figure 173:
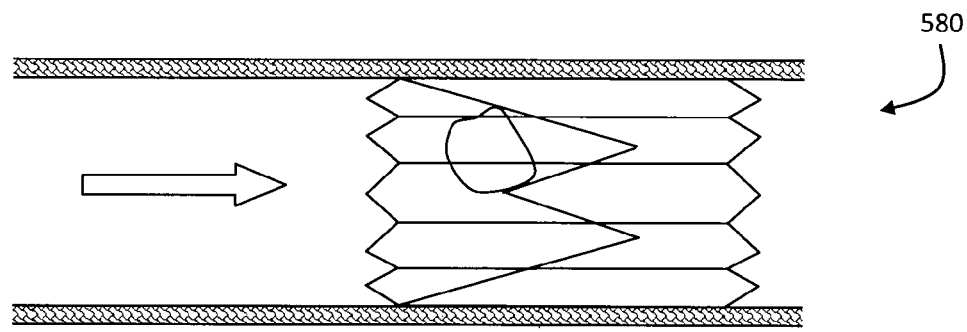
FIGS. 173 to 177 show an alternative device with an M-shaped filter.
Figure 174:
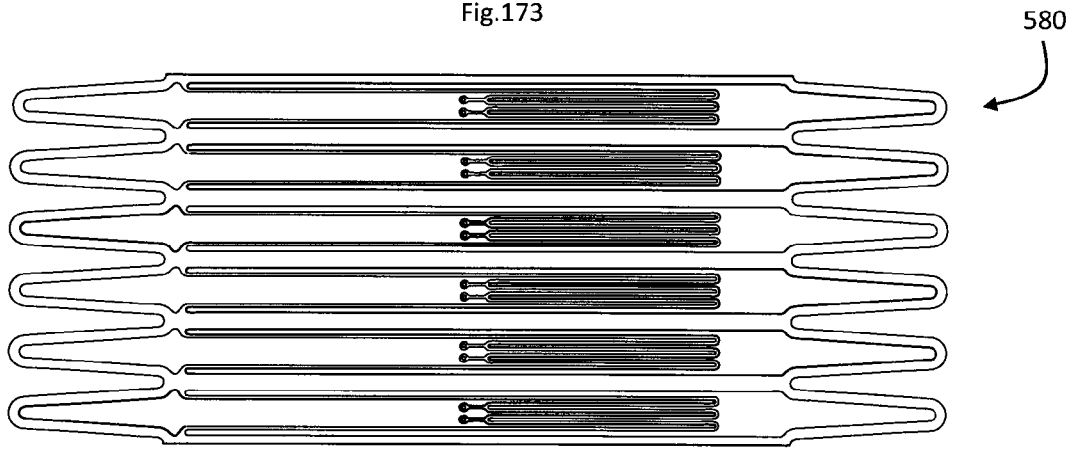
Figure 175:
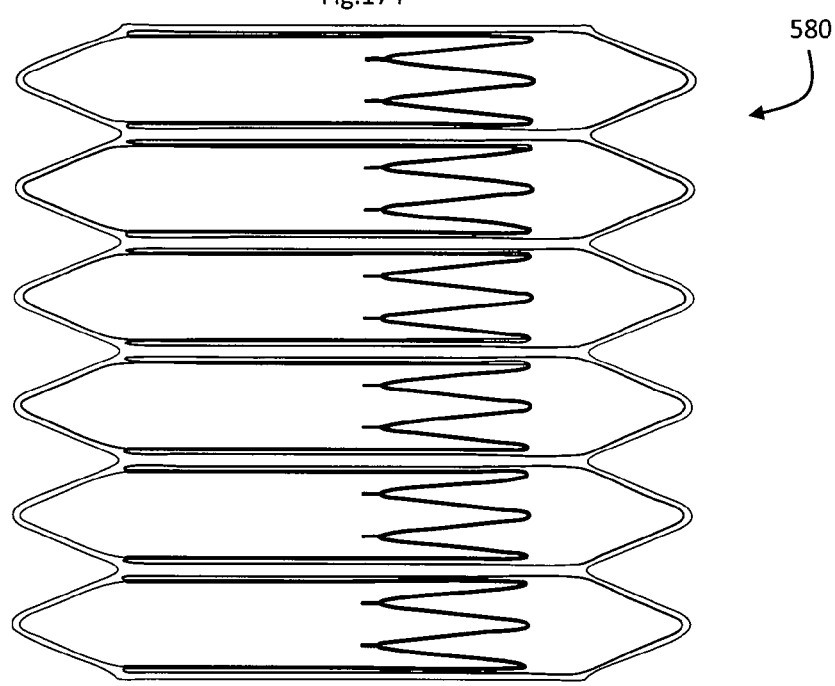

FIGS. 173 to 175

An alternative device, 580, with an M-shaped filter has a trellis retention feature. Note that only the top and bottom filter elements are shown in the vessel view of FIG. 173.

Referring to FIGS. 174 and 175 the filter trellis is shown in a compacted and expanded flat pattern respectively.

The trellis retention feature offers more surface area to trap a clot post conversion, if present. One or more proximal retention trellis peaks may be used. A porous membrane, woven fibres, or alternative filtration structure may be attached to the retention trellis to aid in trapping the clot post conversion, if present. This additional structure may incorporate biodegradable materials.

Figure 176:
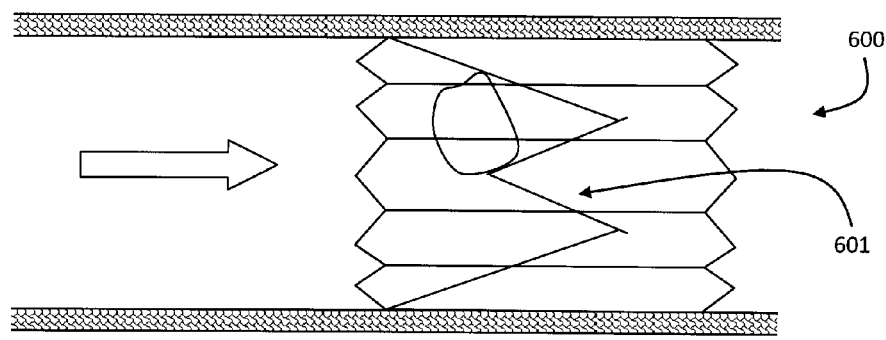
Figure 177:
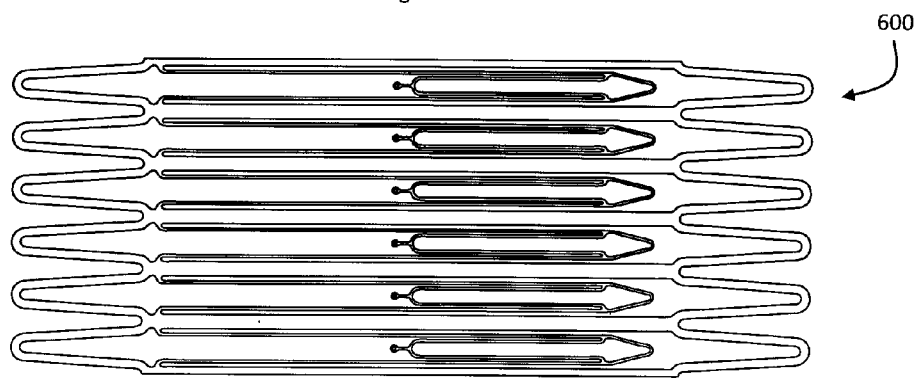
Figure 178:
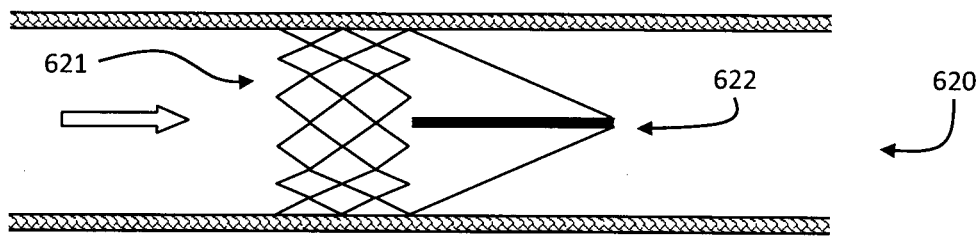
FIGS. 178 to 182 show a filter device with a proximal support trellis and a central filtration trellis.
Figure 179:
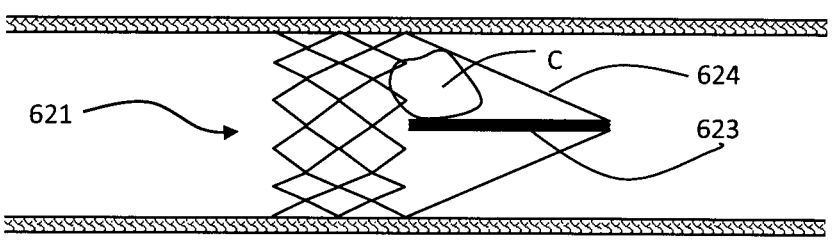
Figure 180:
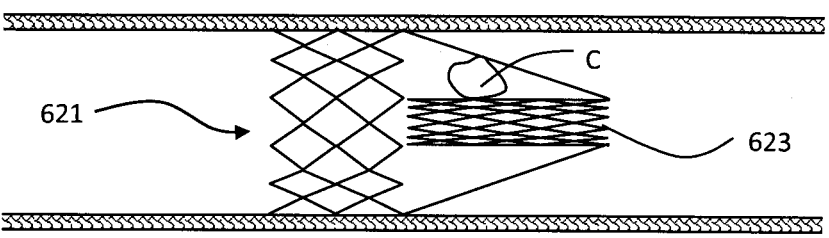
Figure 181:
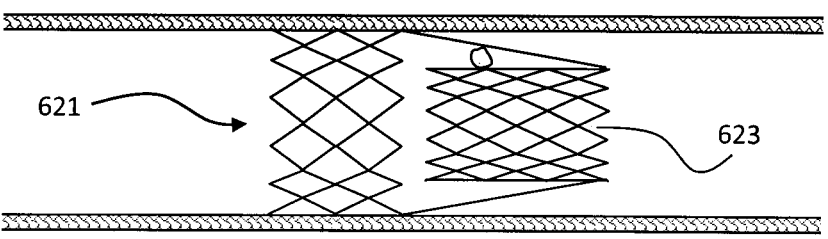
Figure 182:
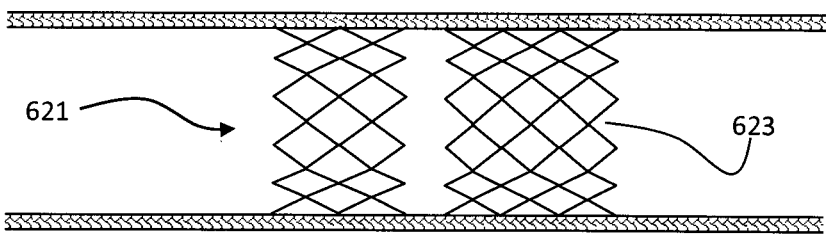
Figure 183:
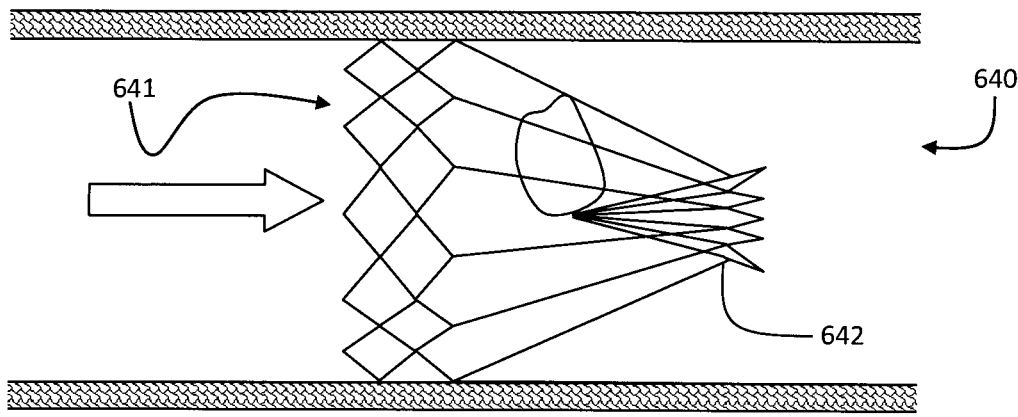
FIGS. 183 to 187 show a filter device with a proximal lattice ring-shaped support to which a filter is connected.
Figure 184:
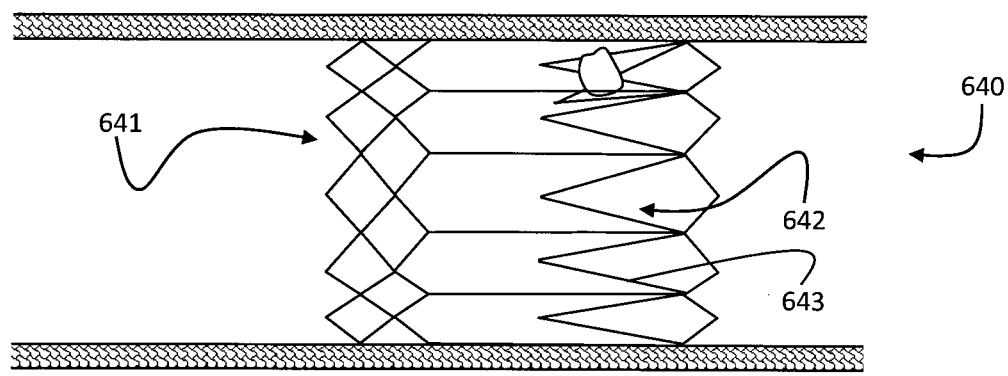
Figure 185:
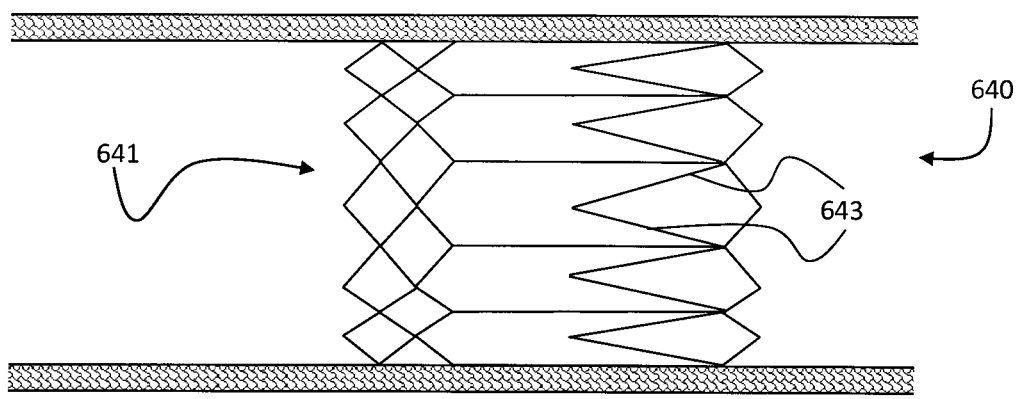

FIGS. 176 and 177

A device 600 has an M-shaped filter 601 has an alternative trellis retention filter. This includes a closed cell to offer improved structural rigidity and cell spacing when holding a clot. One or more retention cells may be used. Note that only the top and bottom capture arms are shown in the vessel view.

FIGS. 178 to 182

A filter device 620 is provided with a proximal support trellis 621. A filter 622 comprises a central filtration trellis 623 and filtration elements 624 linking the filtration trellis 623 to the support trellis 621. The filtration trellis 623 expands after a time determined by a holder in the form of a tie, ring, or tube to compact a clot C retained in an annular filtration area. Again, there is effective filtering while the filter is in the closed position, and even after release it retains a clot as illustrated and the trellis also provides additional radial force to aid in breaking down the clot through lyses.

FIGS. 183 to 187

A filter device 640 has proximal lattice ring-shaped support to which a filter 642 is connected. The filter 642 has an alternative trellis retention feature. The trellis retention feature has a zigzag arrangement 643 providing a closed cell to offer improved structural rigidity and cell spacing when holding a clot. This retention cell provides additional radial force to aid in breaking down the clot through lysis and becomes a distal support feature upon conversion.

Figure 186:
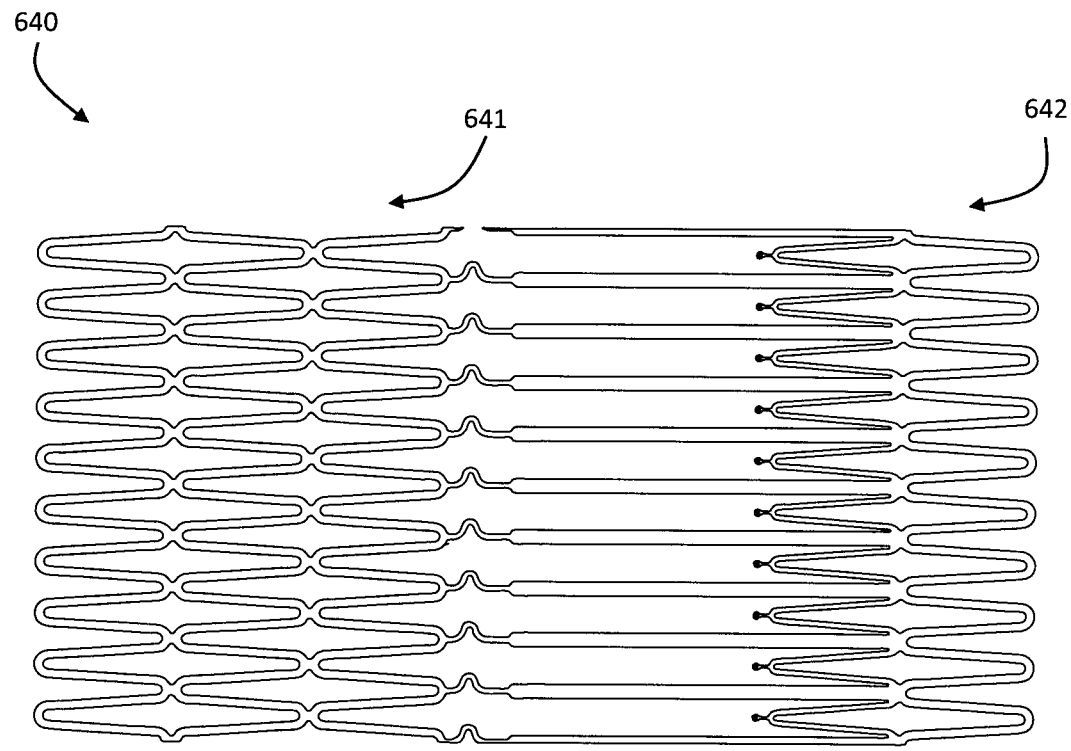
Figure 187:
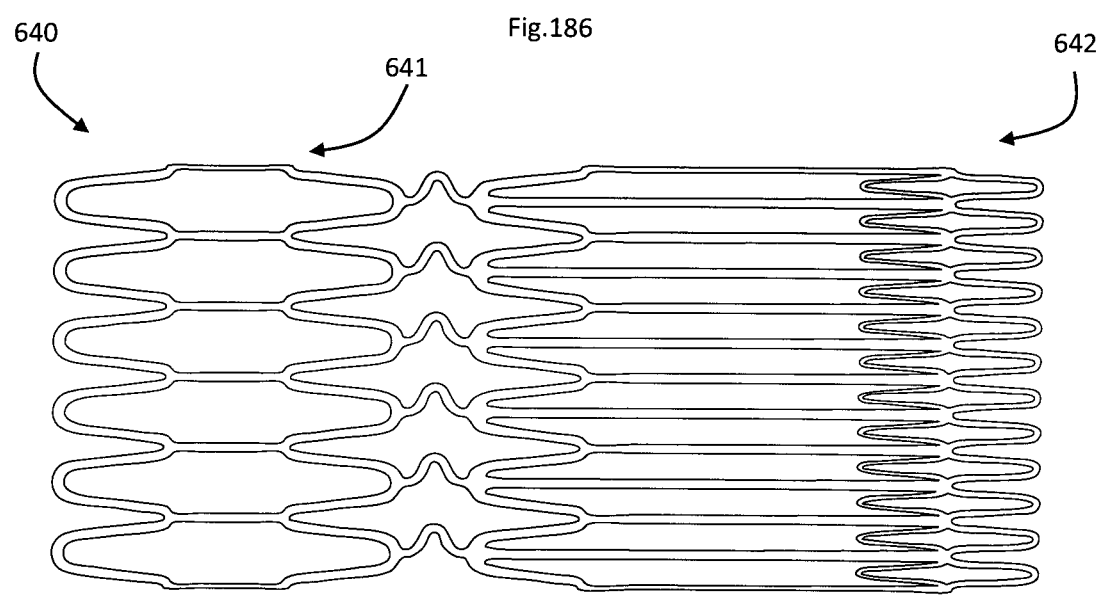
Figure 188:
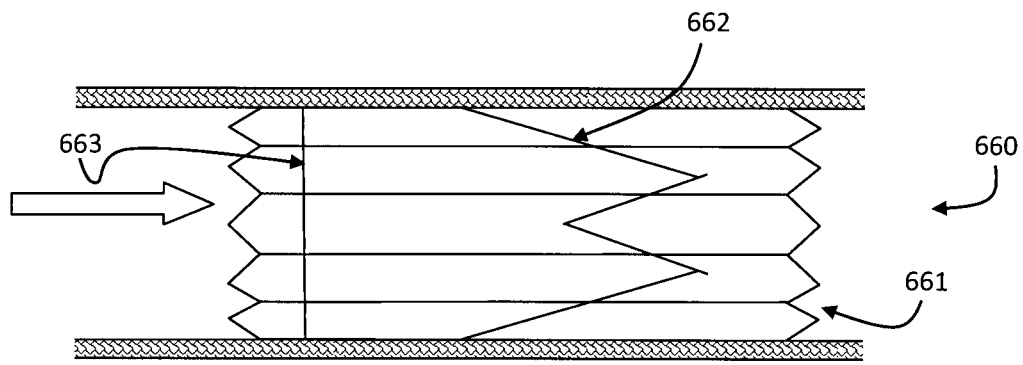
FIGS. 188 to 191 show a filter device with an M-shaped filter and diagonal filter elements upstream of the M-shaped filter.
Figure 189:
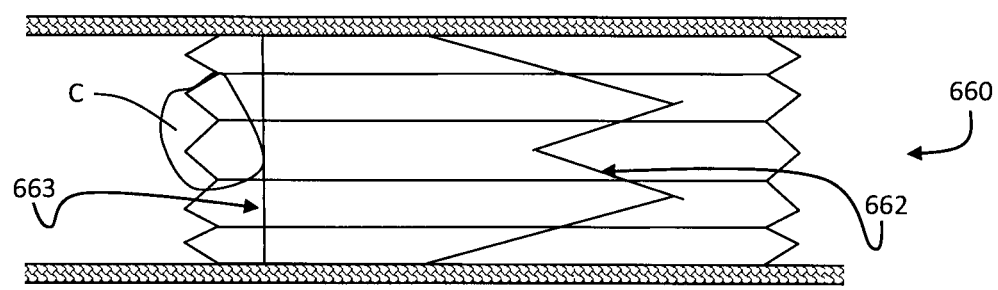
Figure 190:
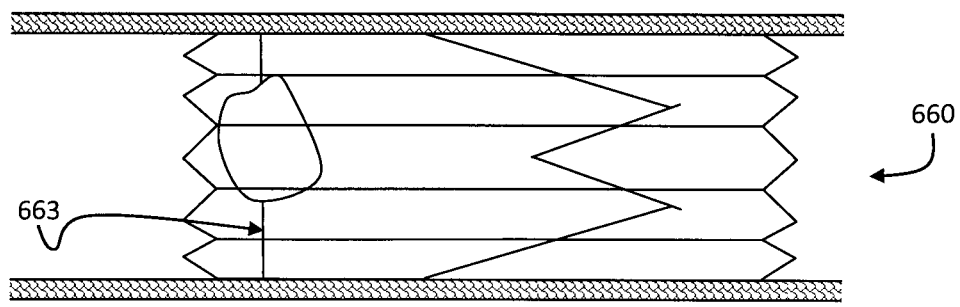
Figure 191:
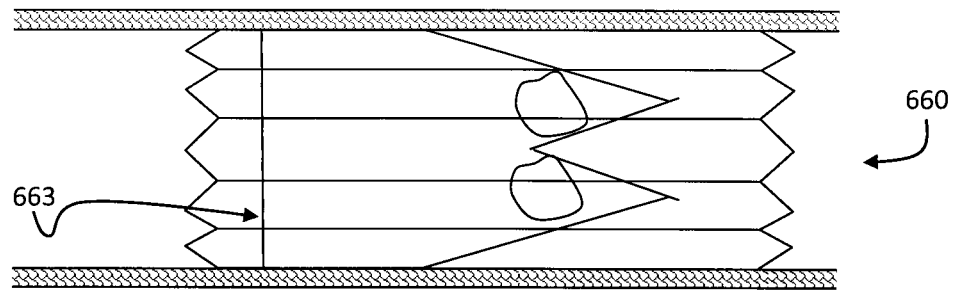
Figure 192:
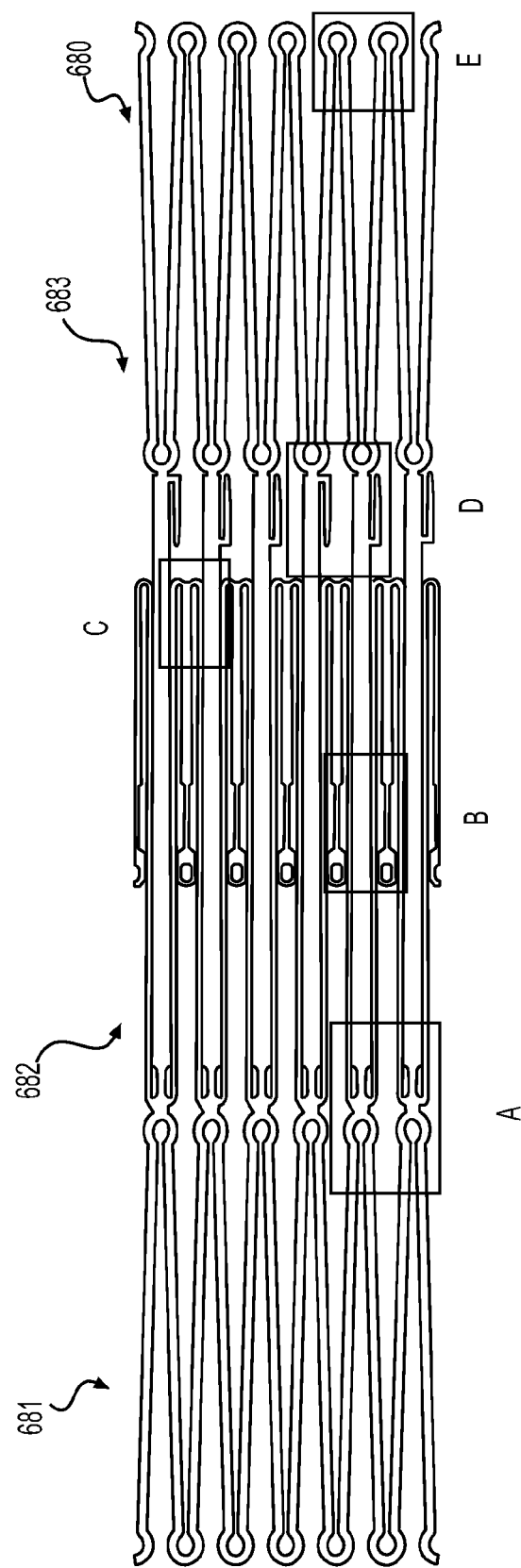
Figure 196:
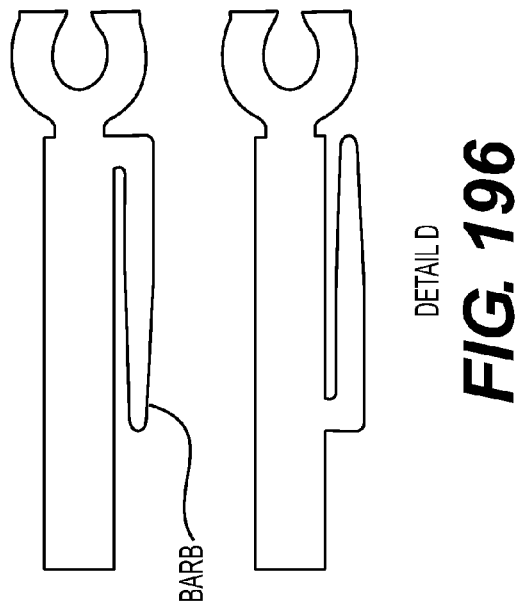
Figure 197:
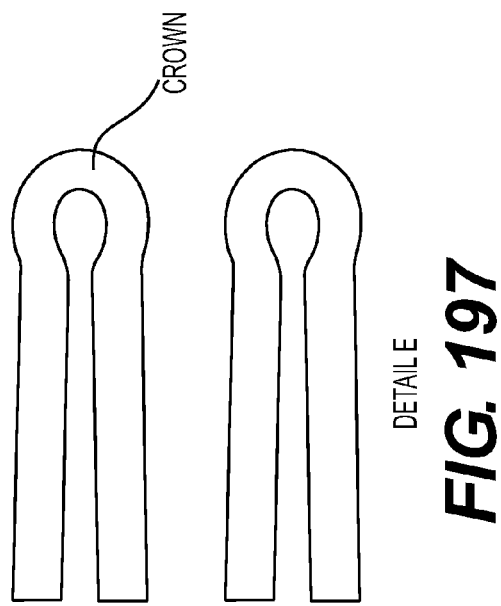
Figure 195:
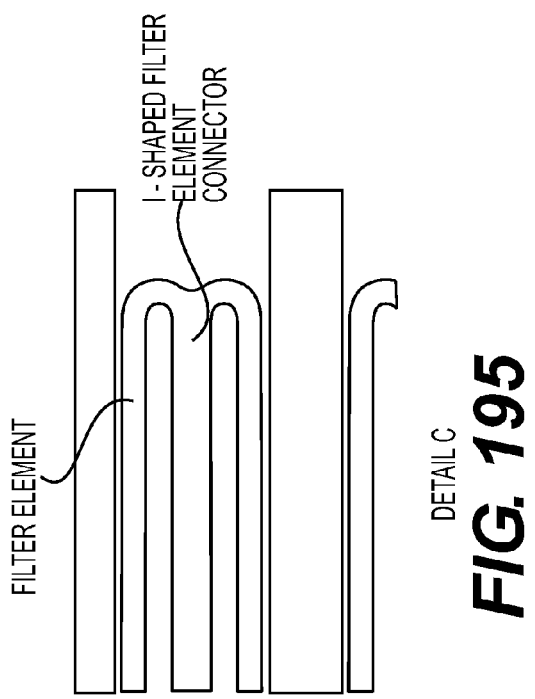
Figure 206:
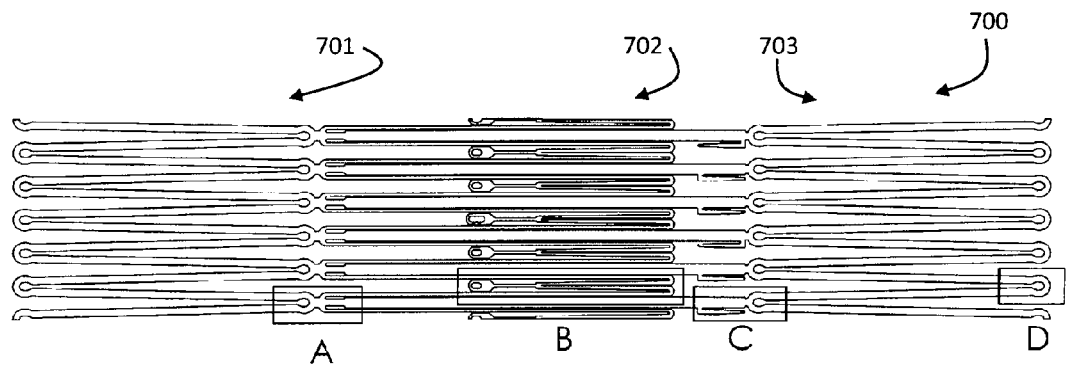
Figure 207:
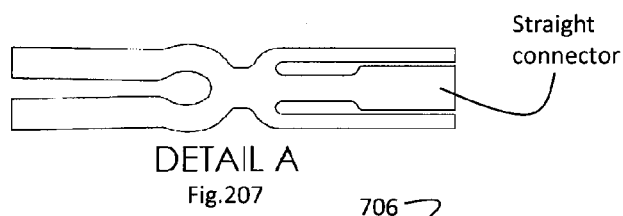
Figure 208:
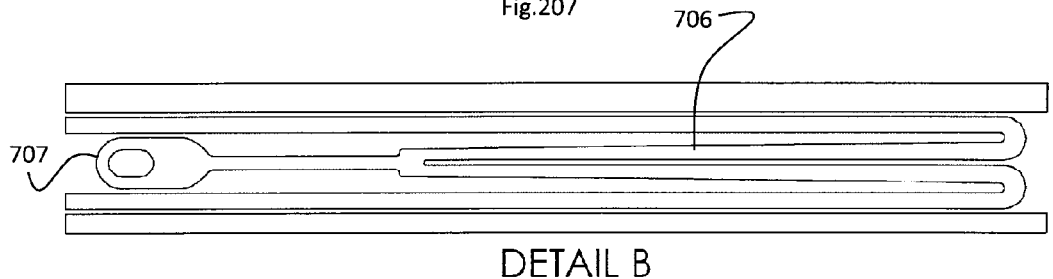
Figure 209:
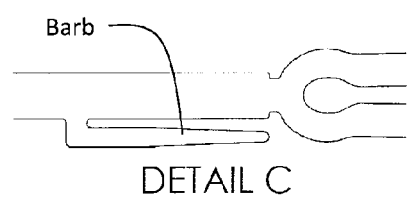
Figure 210:
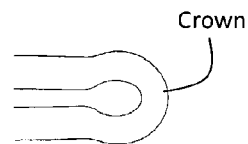
Figure 215:
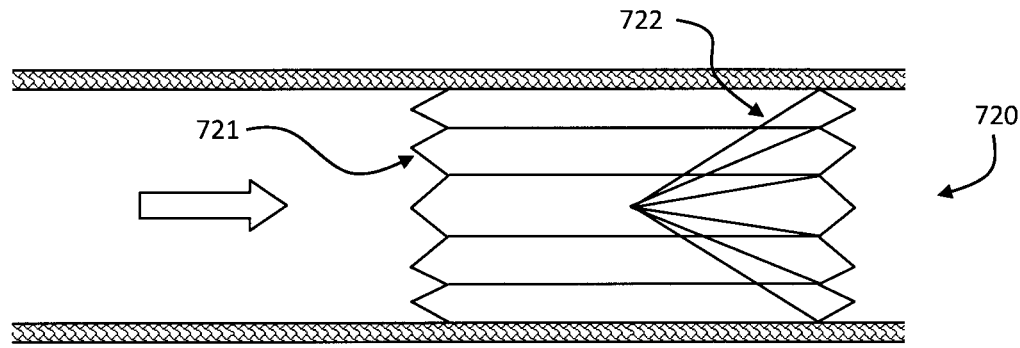
FIGS. 215 to 218 show a device with a filter in the configuration of a cone having an apex facing the proximal end.
Figure 216:
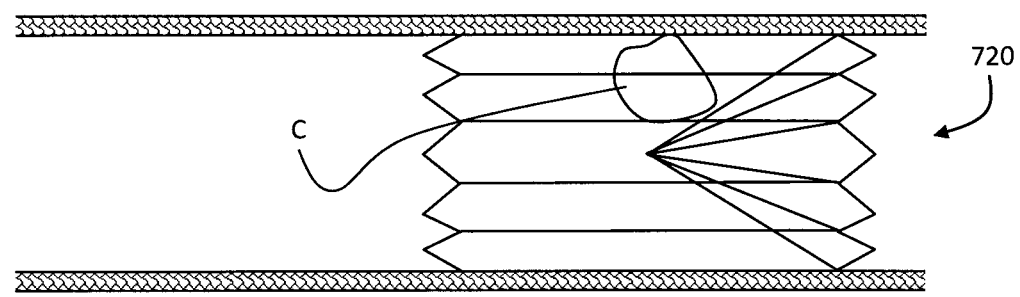
Figure 217:
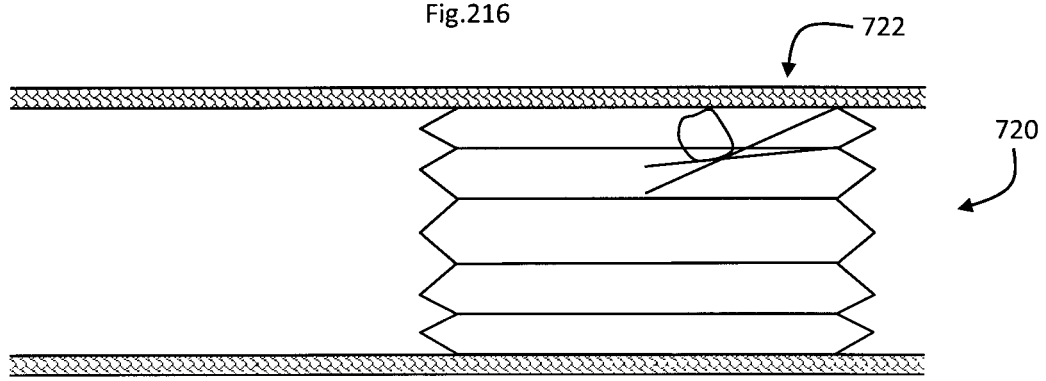
Figure 218:
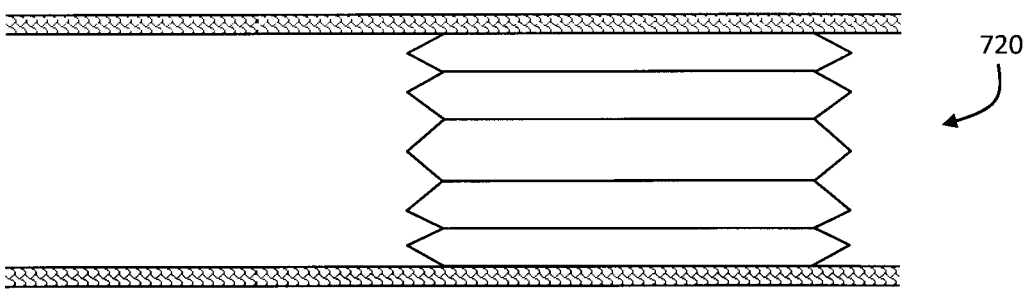
Figure 219:
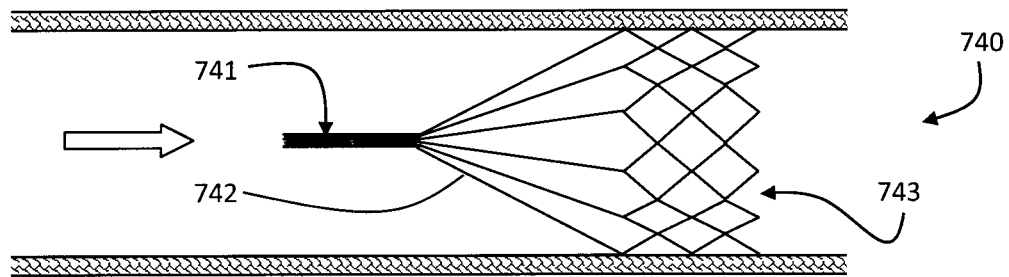
FIGS. 219 to 222 show a device with an expanding proximal trellis for clot lysis post conversion.
Figure 220:
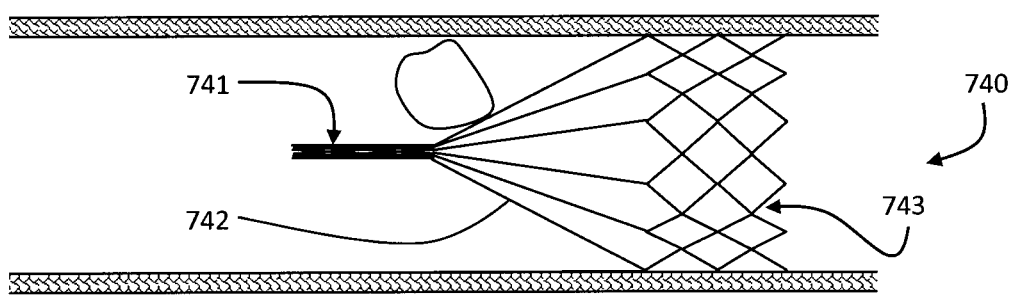
Figure 221:
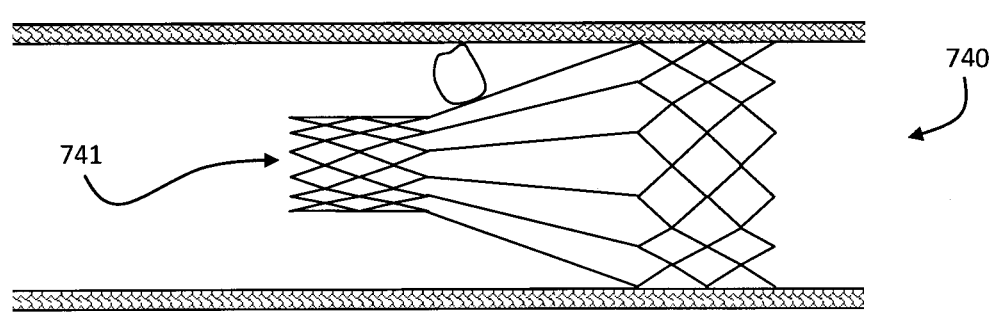
Figure 222:
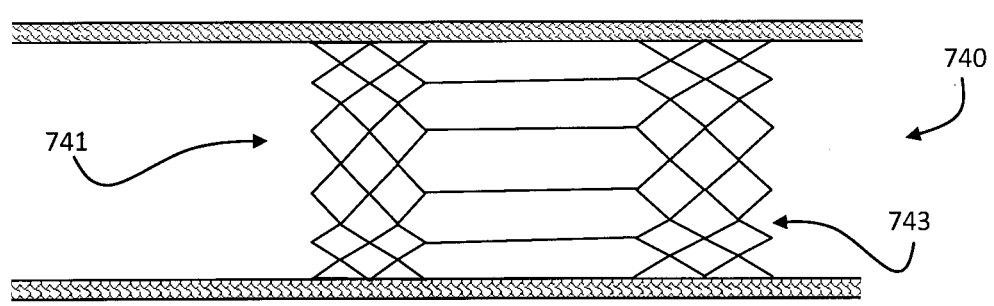
Figure 223:
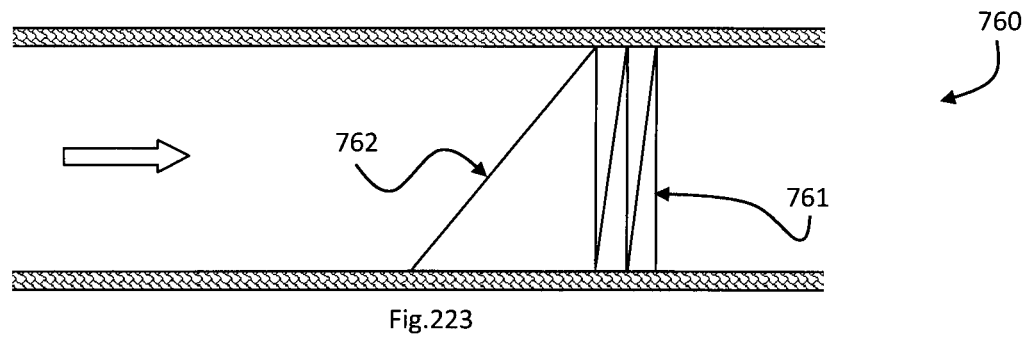
FIGS. 223 to 226 show a filter device with a helical coil distal support extending into a proximal loop.
Figure 224:
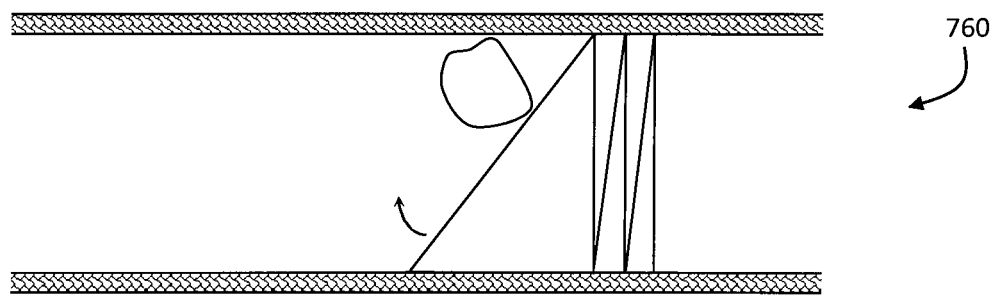
Figure 225:
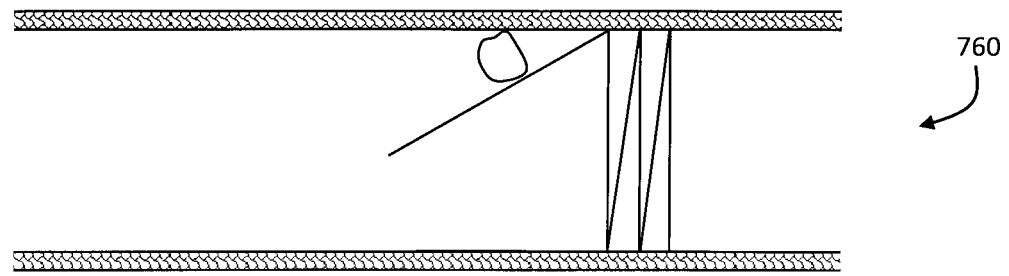
Figure 226:
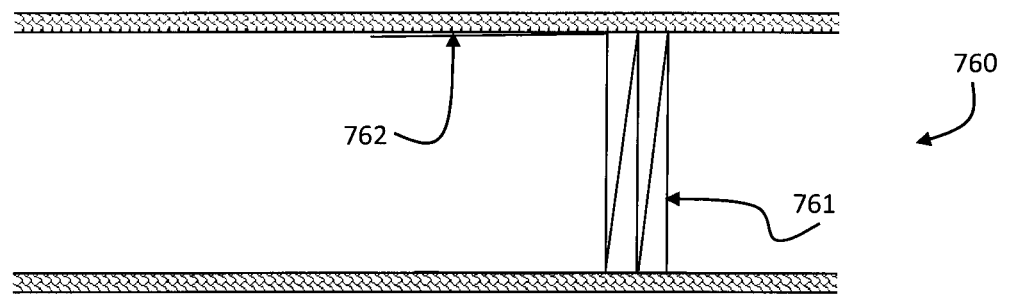

FIGS. 186 and 187 show the device in flat pattern to illustrate its configuration in more detail.

Additional proximal support rings may be added to improve tilting characteristics. Features may be added to the most distal peaks of the proximal hoops that offer flexibility between the proximal support and the capture arms. This will minimize lift-off of the support rings from the vessel wall. Larger proximal cells may be employed along with smaller distal cells to provide more proximal radial force and less distal radial force. This will aid in preventing lift off from the vessel wall.

FIGS. 188 to 191

A filter device 660 has a stent-like support 661, an M-shaped filter 662, and diagonal filter elements 663 upstream of the M-shaped filter 662. The proximal filter elements 663 are configured to cut a large clot before it reaches the reception space of the filter 641. The proximal filter elements 663 comprise biodegradable tethers extending vertically from one support arm to the opposing support arm so that it passes the centre of the vessel. As the vessel changes from cylindrical to oval during breathing, the tether imparts a cutting action to the clot. If three were used, the orientation of the filter in the vessel would not affect the cutting ability of the tethers. Inferior vena cava pulses in an axial direction unlike arteries that compress radially.

FIGS. 192 to 205

A filter device 680 comprises a proximal support hoop 681, intermediate struts 682, and a distal support hoop 683. Filter elements 684 extend with two arms distally until they converge and then a single arm extends proximally. Constructional details are shown in FIGS. 192 to 197. As shown in FIGS. 202 to 205, when closed the filter 684 is retained by a biodegradable holder and provides particularly effective filtering coverage.

FIGS. 206 to 214

A filter device 700 has a proximal support hoop 701, intermediate struts 702, and a distal support hoop 703. Filter elements 705 comprise a V-shaped filter element connector 706 and an eyelet 707. This is a particularly effective arrangement for an M-shaped filter.

FIGS. 215 to 218

A filter device 720 has a stent-like support 721, and a conical filter 722. The conical filter 722 operates in reverse to many of the above embodiments, directing a clot C to the vessel wall and breaking it down after release by the holder member at the apex. Again this device provides very effective filtering action when the filter is closed, and upon opening it retains a clot until it has broken down. The natural bias of the filter elements radially outwards contributes actively to clot lysis. V-shaped filter elements may also be used in place of the illustrated straight filter elements.

FIGS. 219 to 222

A filter device 740 is provided with a distal support trellis 743, a reverse cone filter 742, and a proximal trellis 741. The proximal trellis 741 is movable from a contracted state to an expanded state through biodegradation of a holder member or application of an energy stimulus. The proximal trellis 741 aids repeatable retention of clots if present during the conversion process. It will be appreciated that the radial force of the proximal trellis 741 contributes significantly to actively breaking down a clot.

FIGS. 223 to 226

A filter device 760 similar to the filter device 500 in reverse is provided with a helical coil distal support 761 extending into a proximal loop 762 with a planar filtration screen. Upon release of the screen, a clot if present is trapped between the vessel wall and the screen. Alternatively, a proximal and distal support hoop connected with longitudinal support members may be provided in place of the helical support where the planar filtration screen is attached between a proximal peak of the proximal support and a distal peak of the distal support. The planar filtration screen may have a radially curved surface in the open state so that it does not obstruct the blood flow.

Figure 227:
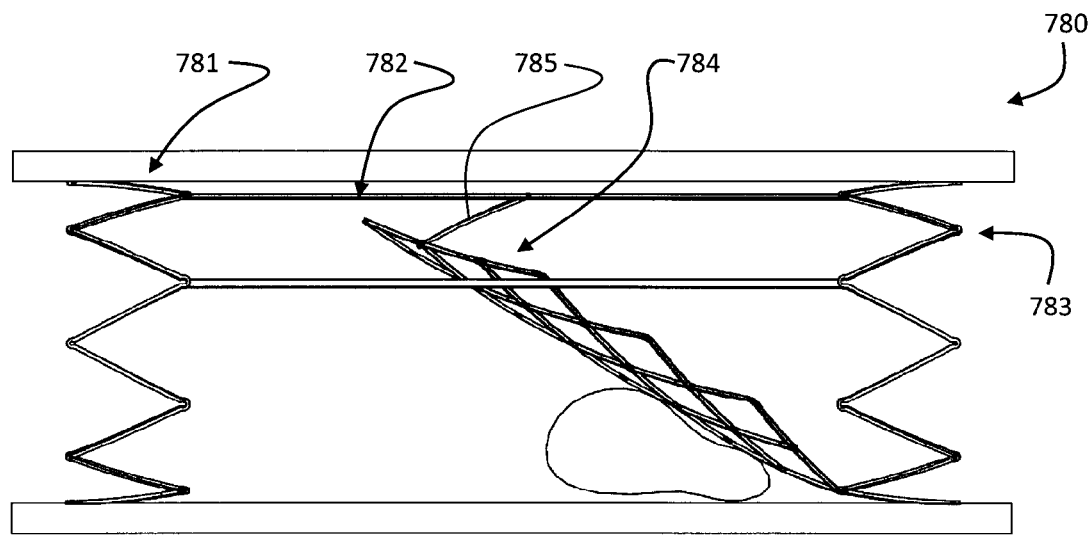
FIGS. 227 and 228 show a device with a lattice filter.
Figure 228:
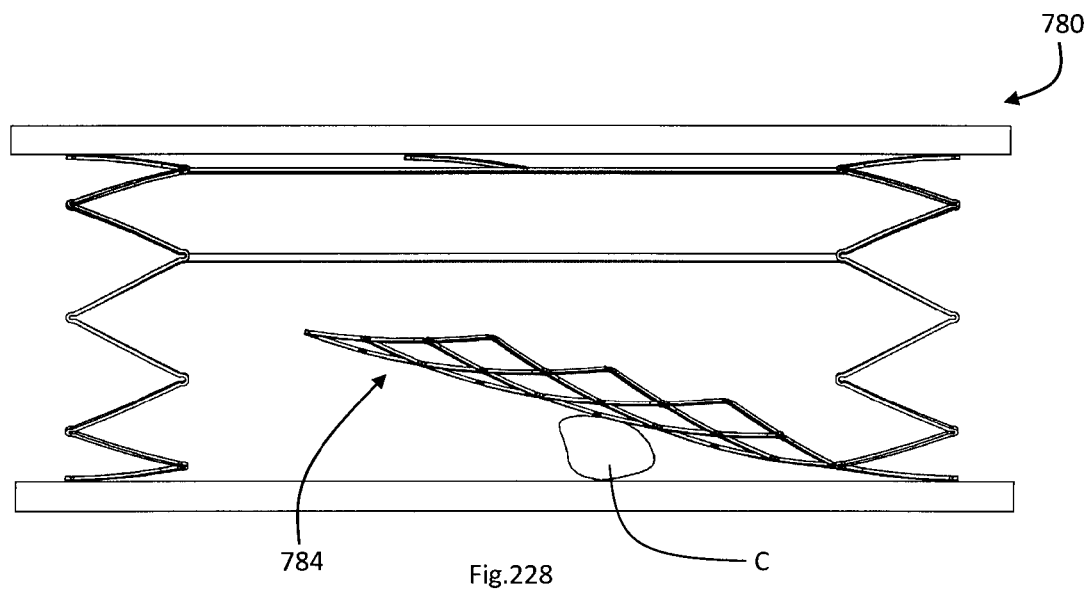
Figure 229:
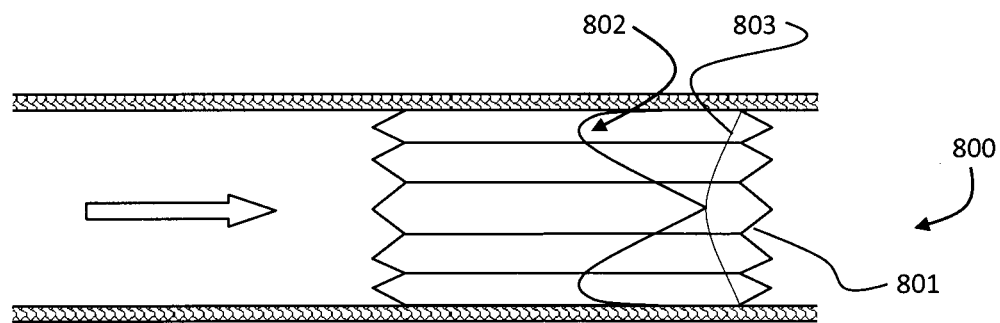
FIGS. 229 to 233 show a device with two-step filter conversion.
Figure 230:
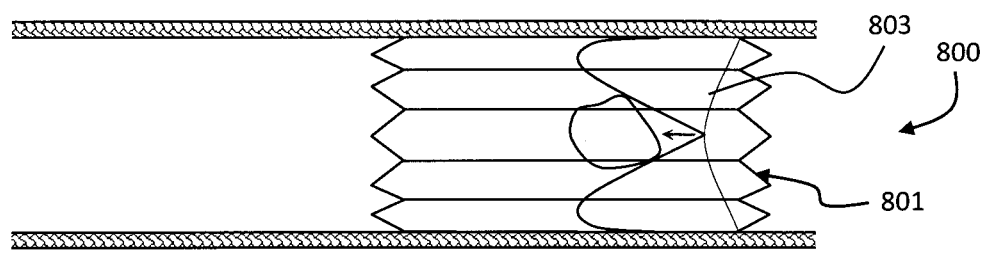
Figure 231:
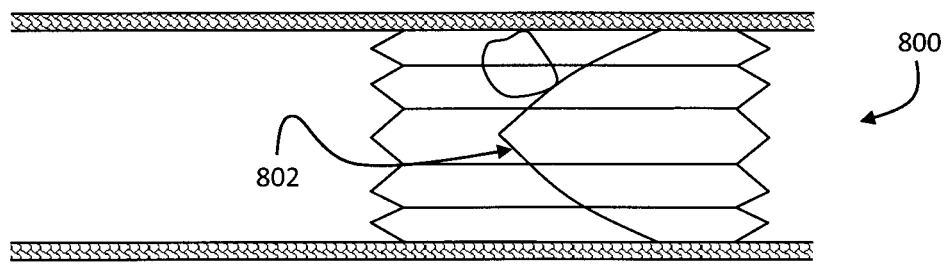
Figure 232:
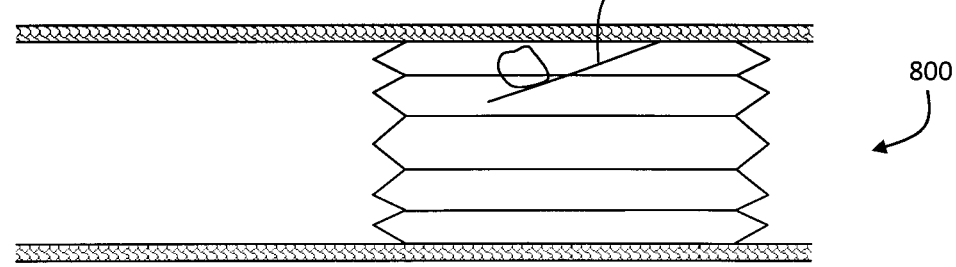
Figure 233:
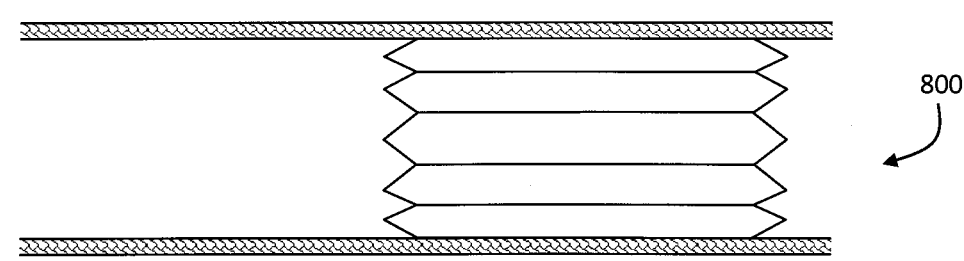

FIGS. 227 and 228

A filter device 780 comprises a proximal support hoop 781, intermediate struts 782, and a distal support hoop 783. The later supports a filter 784 having a lattice configuration. This is biased towards the vessel wall upon release by a biodegradable holder member that secures the free end of the filter lattice 784 and the v-shaped linking member 785. Clots become trapped at one side of the vessel wall in the closed state and are trapped between the vessel wall and the filter lattice 784 if present upon conversion to the open state. The filter lattice may be connected at one or more locations on the support frame. Additional connections will provide additional radial force to aid in pushing the lattice back to the vessel wall upon conversion. As depicted, the lattice is radially curved so that it does not obstruct blood flow in the open state. The lattice may also be provided in the form of a loop with a biodegradable/biostable filtration screen.

FIGS. 229 to 233

A filter device 800 has a stent-like support 801, and filter elements 802 extending from the support intermediate struts proximally and then bent to extend distally and meet on-axis where they are retained by a releasable tensioner 803 extending across the support. The releasable tensioner 803 extends through the apex of the cone from the distal support ring. Conversion may occur in one or two steps. One step conversion: the filter elements spring back to the vessel wall and trap clot if present against the vessel wall until lysis is completed. Two step conversion (as illustrated): (1) after the protection period, the inverted cone reverts to form a cone pointing proximally (2) after an additional period of time, the cone converts and traps clot if present against the vessel wall until lysis is completed.

FIGS. 234 to 239

Figure 234:
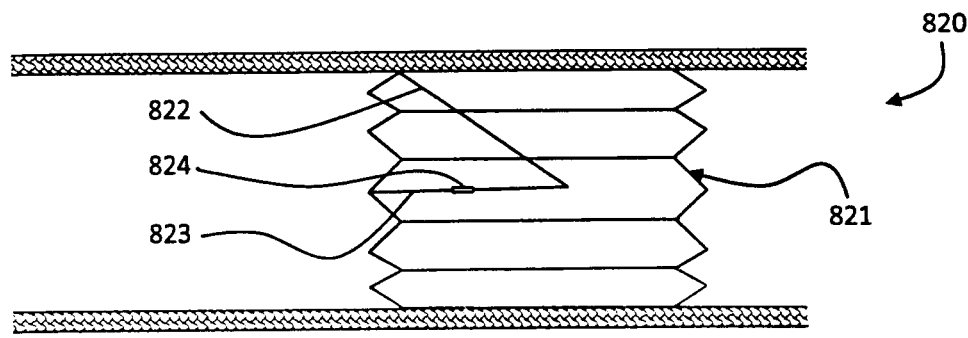
FIGS. 234 to 239 show a device having a filter which acts on a clot post conversion due to an un-twisting or un-winding action to release stored energy.
Figure 235:
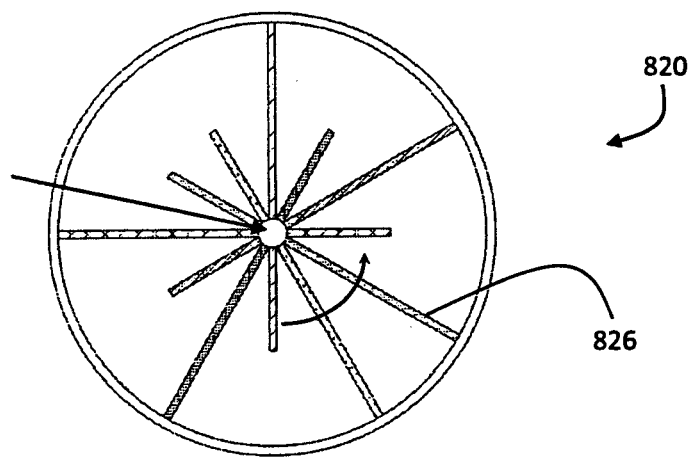
Figure 236:
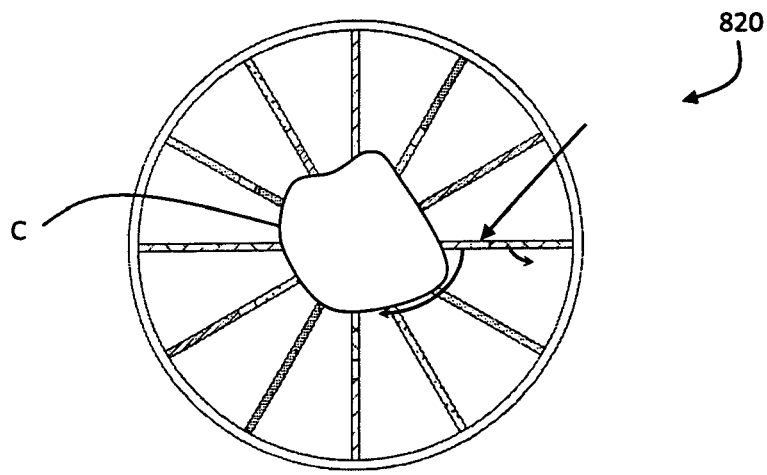
Figure 237:
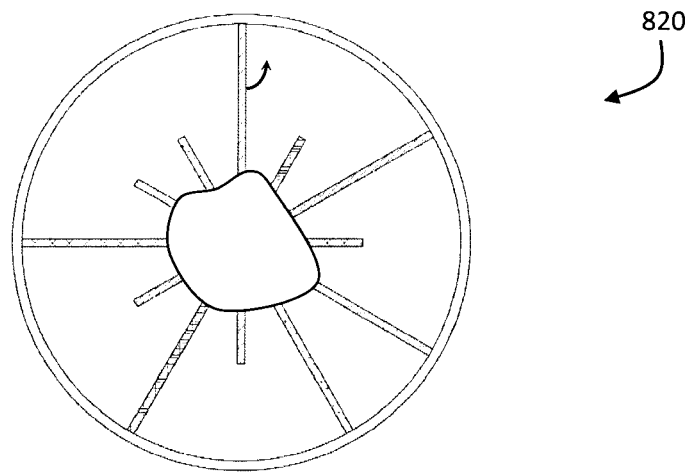
Figure 238:
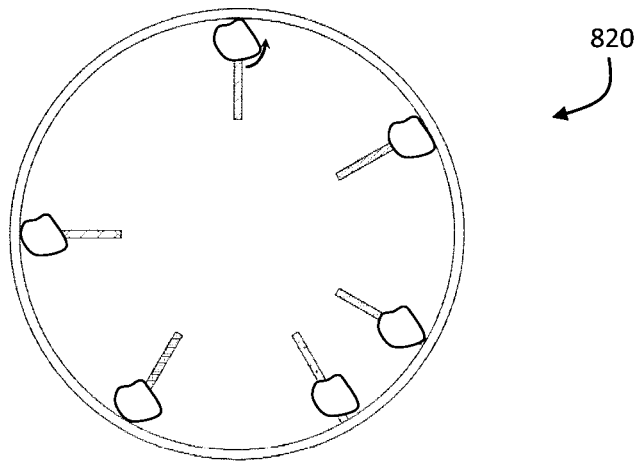
Figure 239:
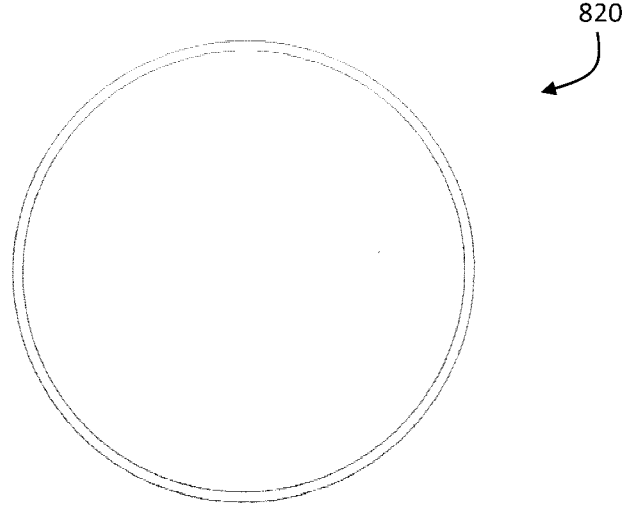

A filter device 820 is provided with clot agitation and rention features. It has a stent-like support 821, an L-shaped filter arm 822 connected to a straight filter arm 823 by a biodegradable coupler 824. A holder couples the L-shaped capture arms 822 at the apex of the L in the centre of the vessel (FIGS. 234 and 235). The short section of the L-shaped capture arm is then twisted and the biodegradable coupler 824 connects it to the adjacent straight capture arm. The couplers 824 preferrably degrade first. When this happens, the straight capture arms 823 return to the vessel wall and the twisted L-shaped arms 822 unwind to provide a cutting action to remove any clot protruding from the capture cone. The holder at the apex degrades second and also creates a cutting action, this time to break the clot into smaller pieces (FIGS. 237, 238). After cutting the clot, the L-shaped capture arms 822 return to the vessel wall along with a clot if attached, and provide a third cutting action to break the smaller clots into even smaller clots (FIGS. 238, 239). When all of the clot is removed, the L-shaped capture arms 822 take a shape non-obstructive to flow (FIG. 239). Note that FIG. 234 only shows one L-shaped capture arm and an adjacent straight capture arm.

These are examples of devices in which the filter elements are wound to store energy and unwind at conversion to impact on a captured clot. Hence, because in many cases the clot will be immediately broken down after conversion, retention time is either a) a short time where the clot is being broken down or b) the short time to break the clot down and an additional time where the broken down clot remains attached to the filter and is lysed by the body, where the lysing time is less than it would have been if the clot was not broken down.

FIGS. 240 to 243

A conical filter device 840 is provided with a number of straight capture arms and a number of profiled heat set capture arms. The profiled capture arm 842 includes a triangular shape 843 towards the distal end. It is appreciated that the profiled capture arm may encompass alternative shapes—curves, spirals, polygons. The straight capture arms are coupled together at the apex to form a cone with a first biodegradable restraint. The profiled capture arms 842 are twisted (0-180 degrees) so that the profile shape protrudes into the cone and are coupled together at the apex with a second biodegradable restraint. The second biodegradable restraint is coupled to the first biodegradable restraint. This stops the twisted profiled capture arms from unwinding. During the initial period of protection, a clot is captured in between the profiled capture arms and the straight capture arms. The coupling means between the first and second biodegradable restraint degrades first allowing the twisted capture arms to unwind and break up a clot, if present. The coupling means could be integral with either restraint having a reduced tensile strength than the restraints features to hold the capture arms. The capture arms may break their respective restraint in any intentional order. One could set the profiled capture arms to break their restraint before the straight capture arms, this may break up the clot further if the clot is attached to the profiled section and interacts with the straight connectors. Alternatively the straight capture arms may break their restraint first and return to the vessel wall. This would allow unobstructed passage of clot, attached to the profiled arms, to the vessel wall. Or both profiled and straight capture arms may break their restraints at the same time.

Figure 244:
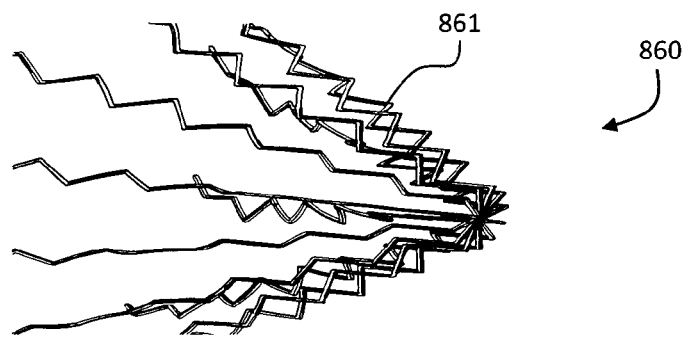
FIGS. 244 to 246 show a device with alternative profiled filter elements which are twisted and coupled at their apex.
Figure 245:
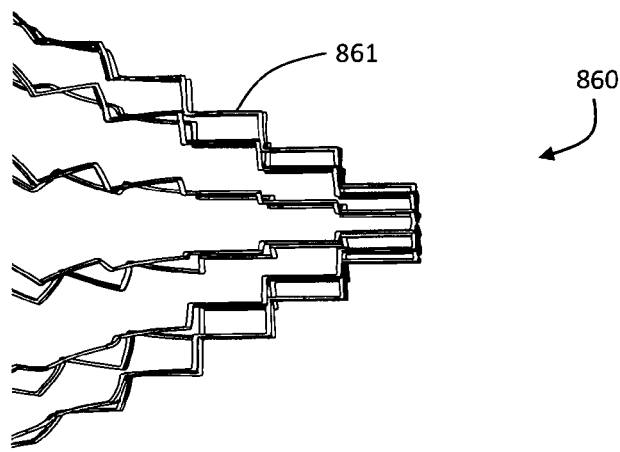
Figure 246:
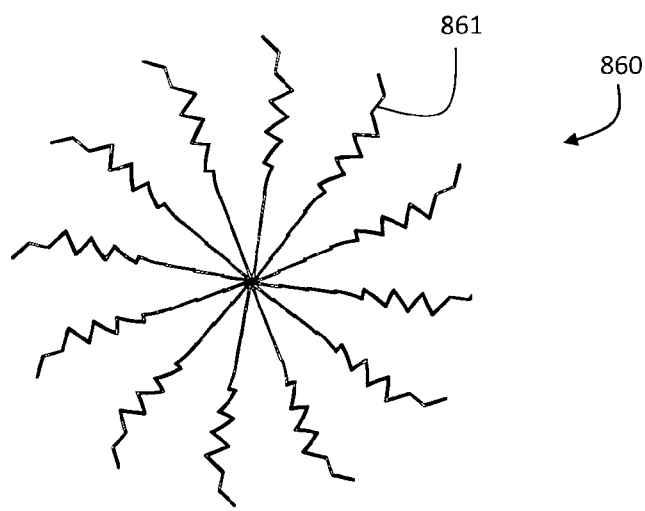
Figure 247:
FIGS. 247 to 252 show a filter device with a spiral/curved filter elements with clot-cutting properties.
Figure 248:
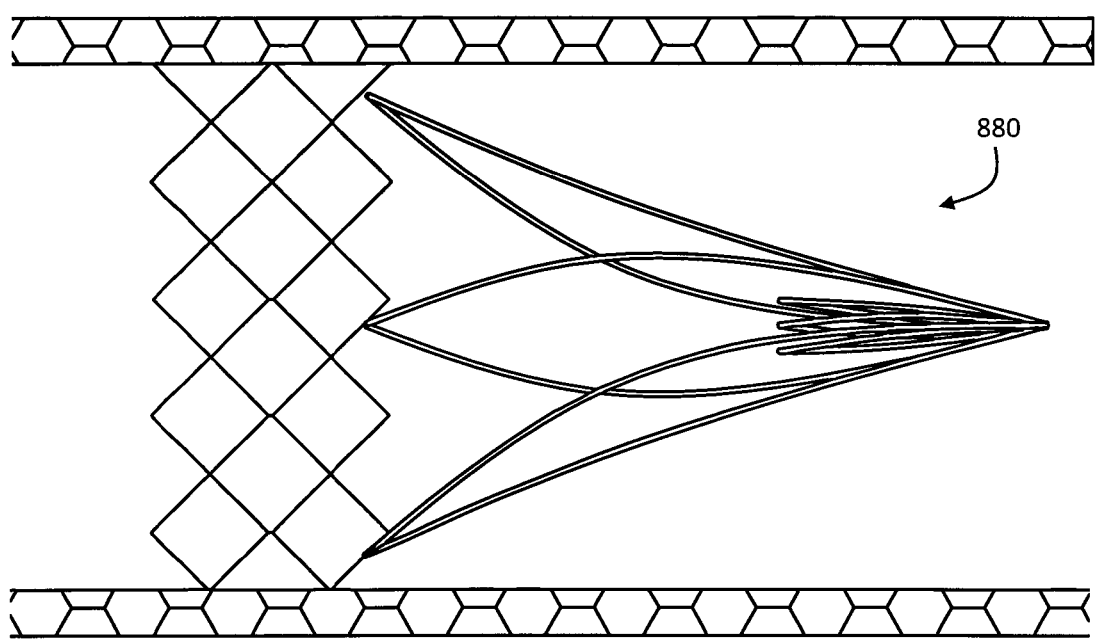
Figure 249:
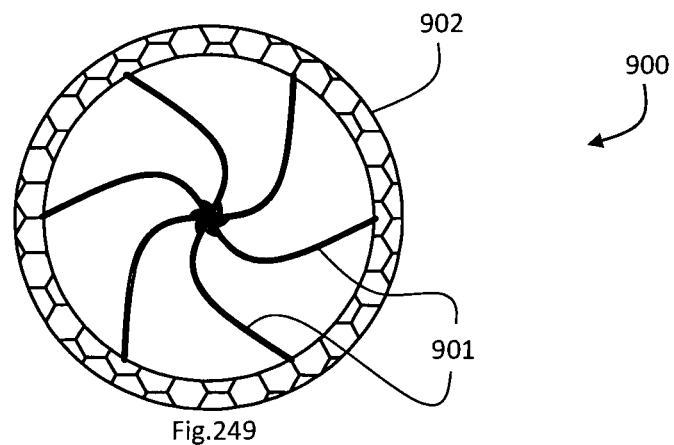
Figure 250:
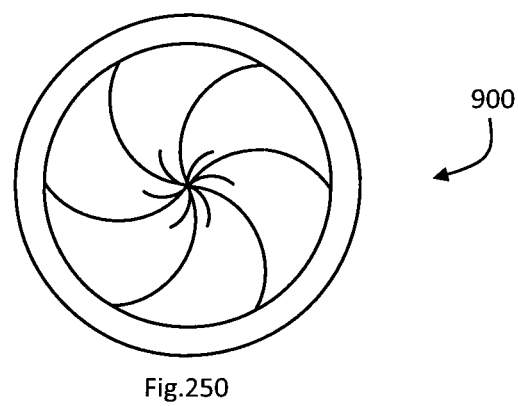
Figure 251:
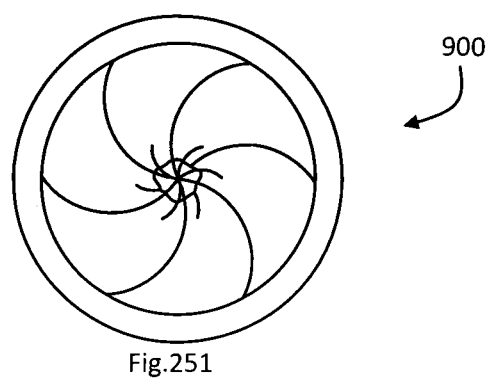

FIGS. 244 to 246

In a filter device 860 sinusoidal capture arms 861 are employed where all arms are twisted and coupled at the apex with a biodegradable holder. Eyelets may be configured to prevent the twisted arms from unwinding. Upon biodegradation, the twisted arms unwind cutting the clot into smaller pieces, if present. It is appreciated that the sinusoidal pattern may be provided in different orientations. For example, each capture arm could be orientated 90° along their central axis.

FIGS. 247 to 252

Figure 252:
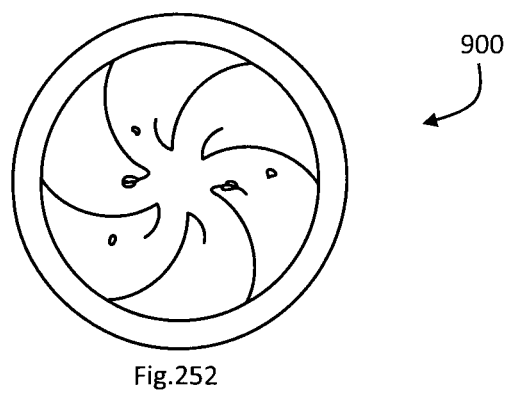

In a filter device 880 there is a spiral/curved filter that is substantially cone shaped with clot-cutting properties. Individual filter elements are best illustrated in FIG. 252. A proximal support hoop may be provided with a number of support rings. A distal support ring may also be provided with longitudinal supports in between. An axial view is shown in FIGS. 249 to 252, device 900 and arms 901 and vessel 902.

The capture arms 881/882 or 901 extend distally from the proximal support hoop or vessel wall to the apex of the cone in a spiral or curved pattern. At the apex, each or at least one capture arm changes direction to extend proximally outwardly. The capture arms are coupled together with a biodegradable material. If clot is present upon biodegradation, the portion of capture arm extending proximally breaks it into smaller pieces. Parts of the clot may still be attached to the filter elements 881 and 882 and if so, will be retained at the vessel wall where lysis can be completed. The spiral pattern may extend in a clockwise or anti-clockwise direction. The spiral pattern may be heat set to move out of plane upon conversion for example, instead of moving back to a point longitudinally in line with the proximal end connected to the vessel wall or support structure, it moves to a point longitudinally offset from its proximal end at the vessel wall.

Figure 253:
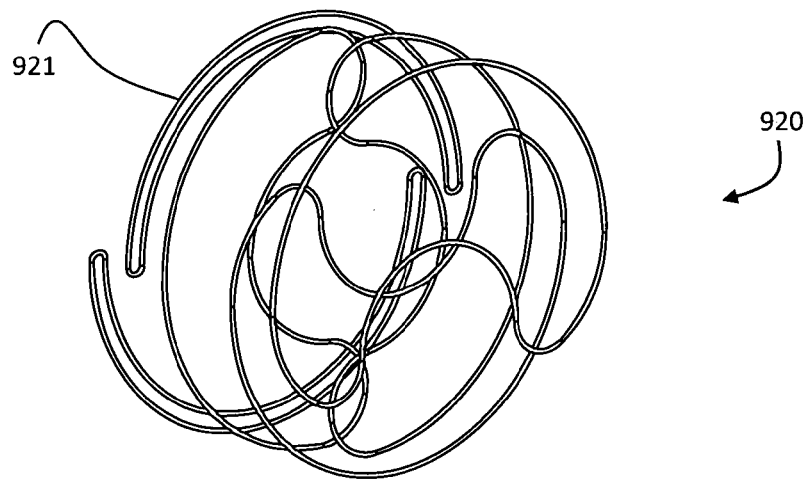
FIGS. 253 to 255 show a device with longitudinally spaced-apart rings with varying degrees of inversion.
Figure 254:
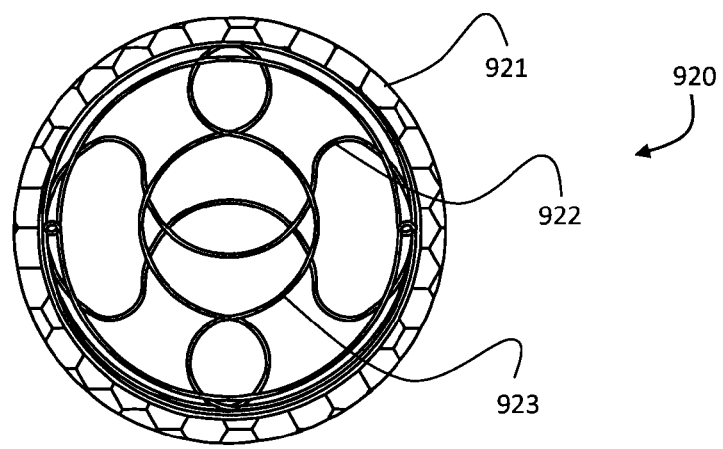
Figure 255:
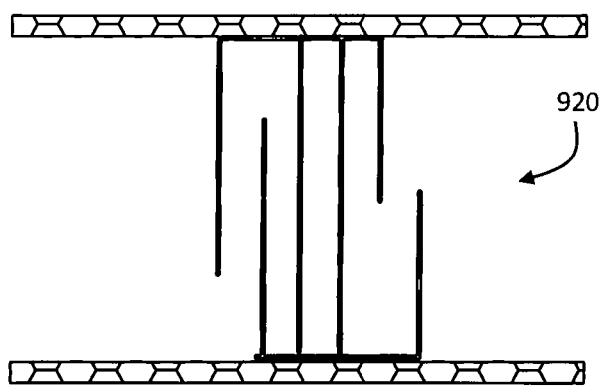
Figure 256:
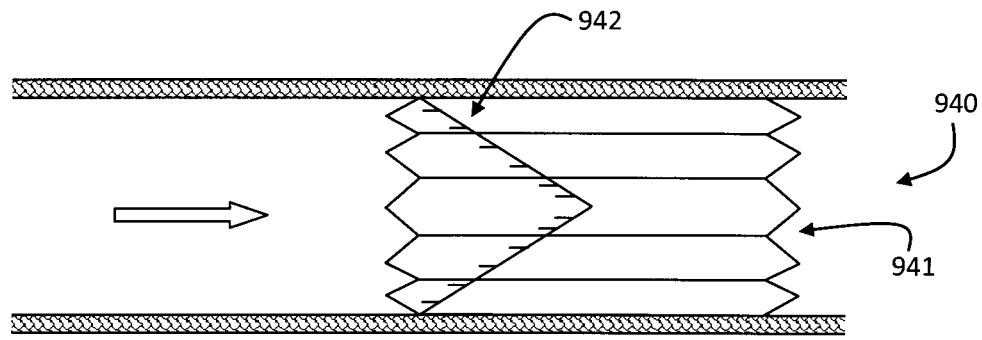
FIGS. 256 to 259 show a device with filter elements having spikes for clot retention.
Figure 257:
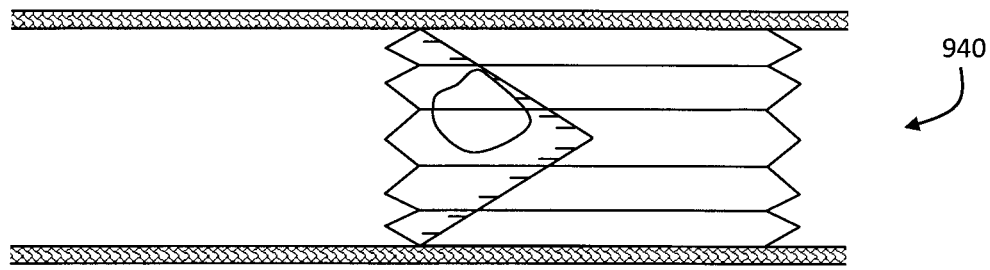
Figure 258:
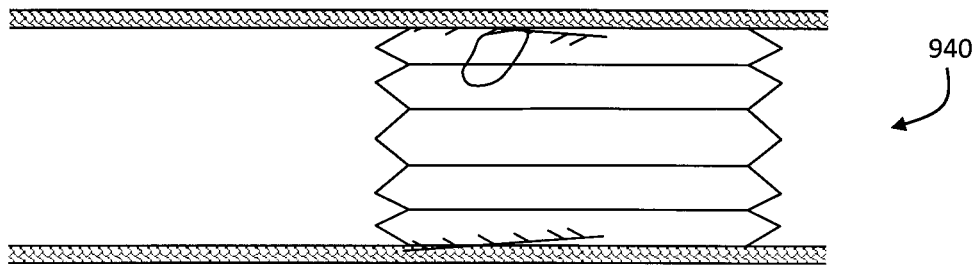
Figure 259:
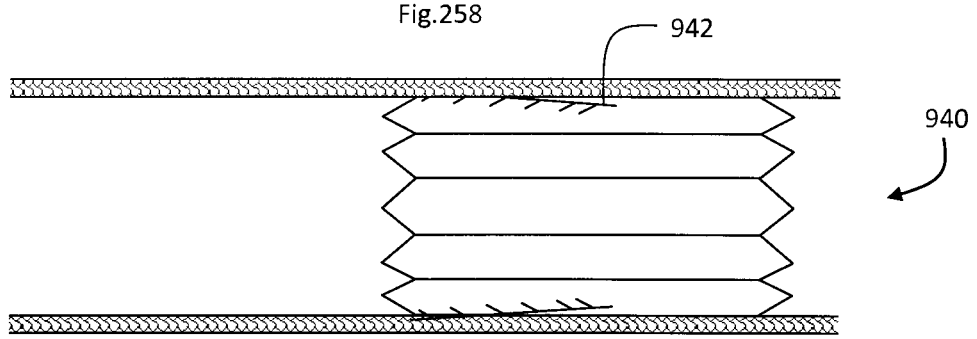
Figure 260:
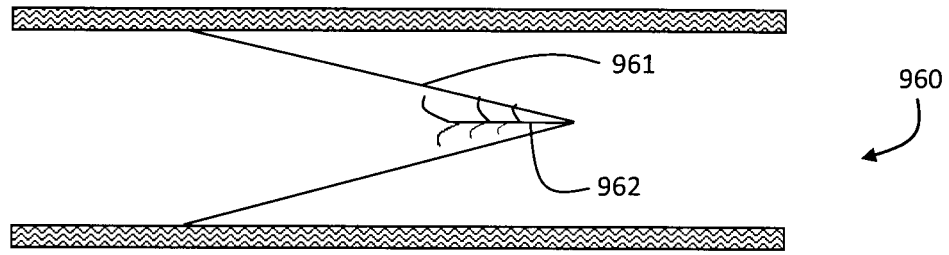
FIGS. 260 to 264 show use of clot retention barbed features on filter elements.
Figure 261:
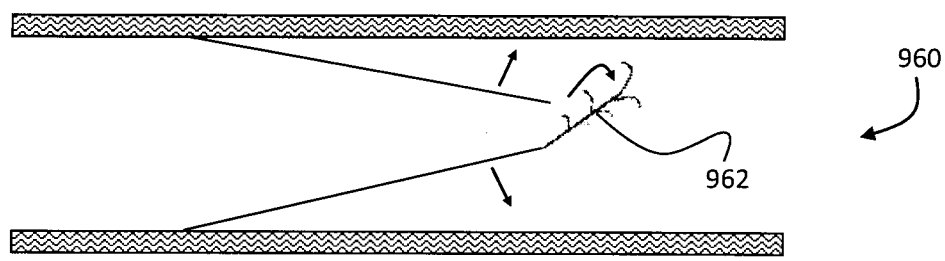
Figure 262:
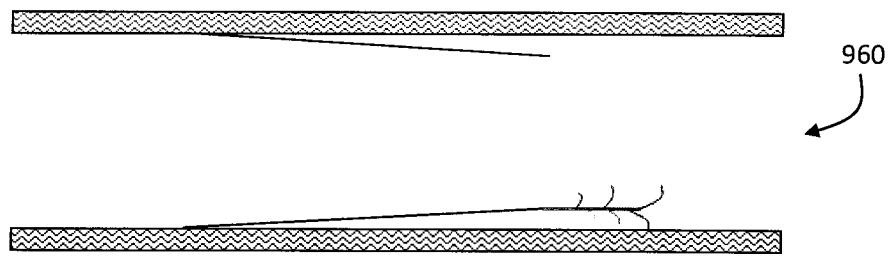

FIGS. 253 to 255

A ring filter device 920 is provided with a conical reception space for clot defined by a number of longitudinally spaced apart rings 922 and 923 with varying degrees of inversion. Inversion is where one side of the ring is pulled radially inwardly towards the other side of the ring where before inversion, an interior concave surface faces an opposing concave surface, and after inversion, an interior convex surface faces an opposing concave surface. The rings may be coupled together with a longitudinal support. The inverted rings are held inverted with a biodegradable coupler or tether. Upon biodegradation, the inverted rings unwind to form a set of non-inverted rings. During this process, a clot if present is pushed up to the vessel wall and/or cut into smaller pieces. FIG. 253 shows an isometric view of how the rings may be arranged. It is appreciated that varying degrees of inversion and orientation of inversion may be employed. FIGS. 254 and 255 show the end-on filtration profile and how each ring is spaced-apart with a longitudinal coupling member. Biodegradable coupling members and tethers are not shown. For instance, a notch may be provided at one set of opposing quadrants of each ring. One half of the ring is inverted and held in position with a biodegradable tether extending from one notch to the other. S-shaped curves may be provided to act as a hinge and aid inversion. Alternatively, the rings have a sinusoidal pattern that extends into a circle or short cylinder, the sinusoid pattern aiding inversion.

FIGS. 256 to 259

A conical filter 942 is provided in a filter device 940 having a stent-like support 941 with filter element spikes. The spikes hold on to a clot if present post conversion until the lysis process is complete. The spikes may be formed integrally with the filter elements or they may be attached as a biodegradable/biostable component. The biodegradable component is preferred.

FIGS. 260 to 264

In a device 960 a conical filter 961 is provided with a clot retention feature 962. If a clot is not completely lysed, the clot is formed around the retention feature. Upon conversion, the retention feature 962 springs distally/proximally so that the clot is retained against the vessel wall. It is appreciated that the retention feature may encompass retaining arms that are orientated in varying degrees around the retaining stem.

Figure 263:
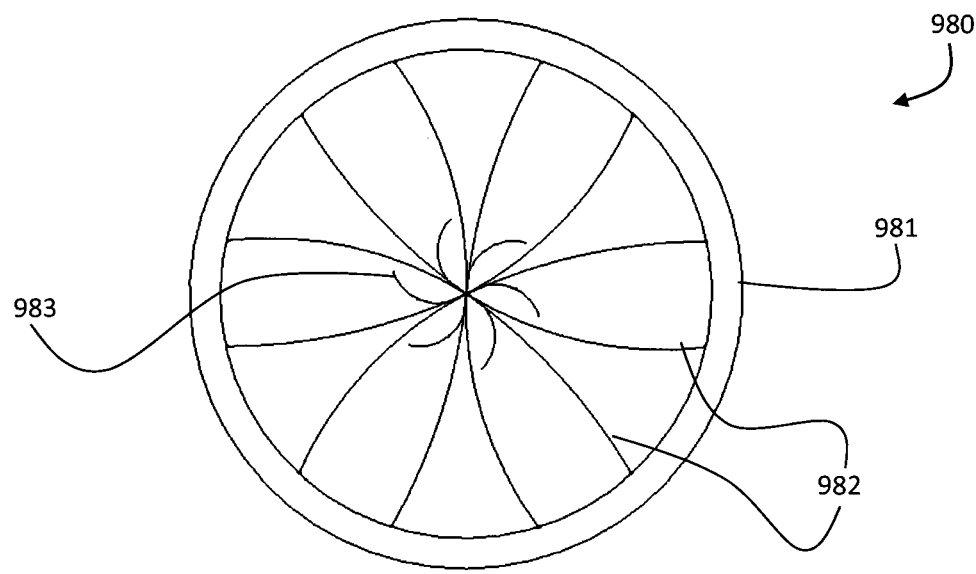
Figure 264:
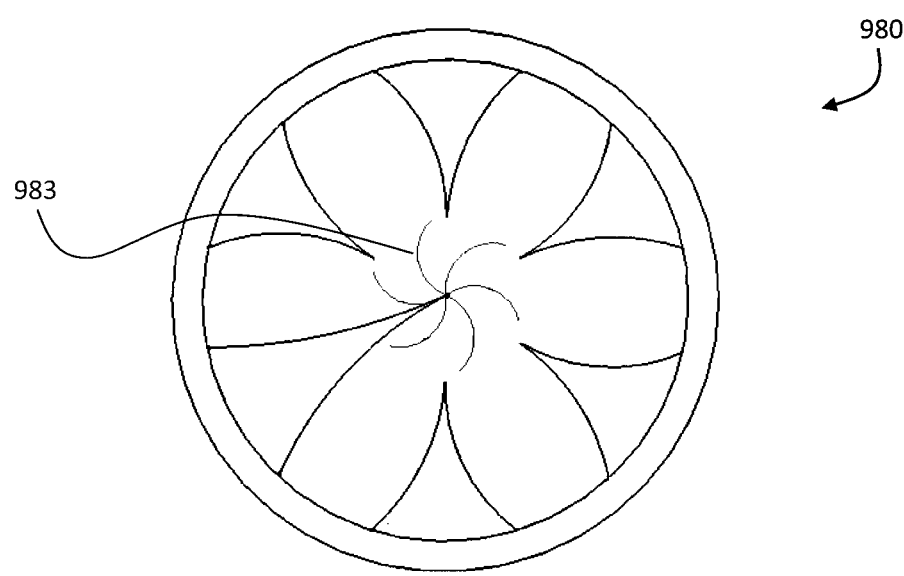
Figure 265:
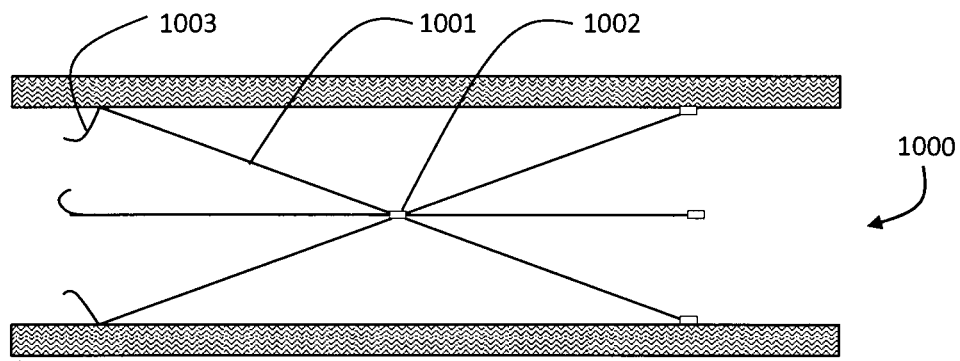
FIGS. 265 to 270 show a device with an arrangement to manually serrate a clot if present.
Figure 266:
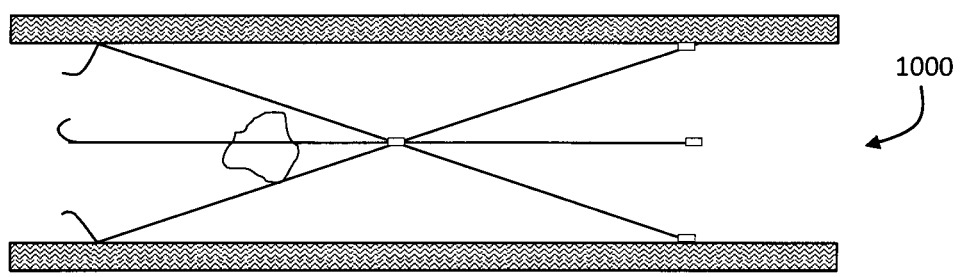
Figure 267:
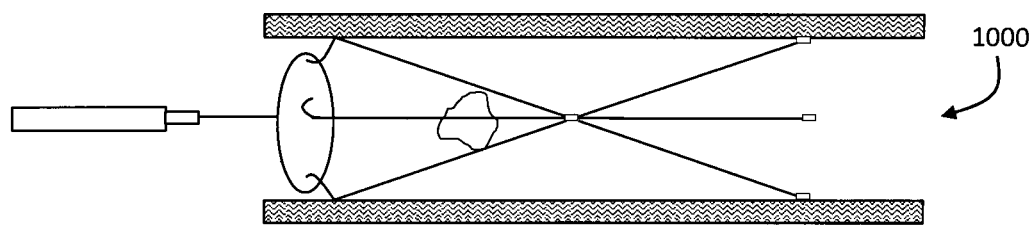
Figure 268:
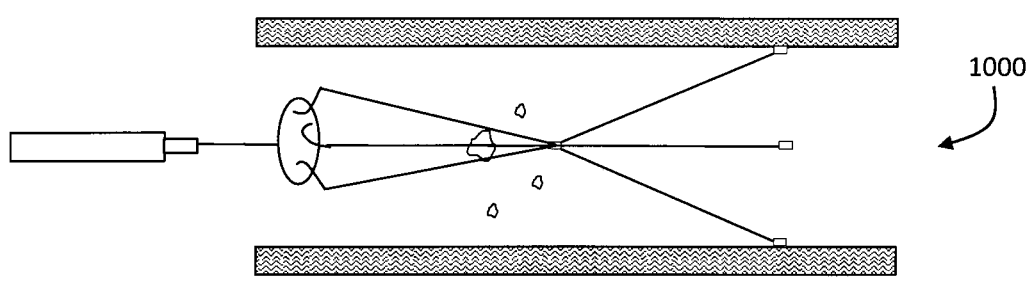
Figure 269:
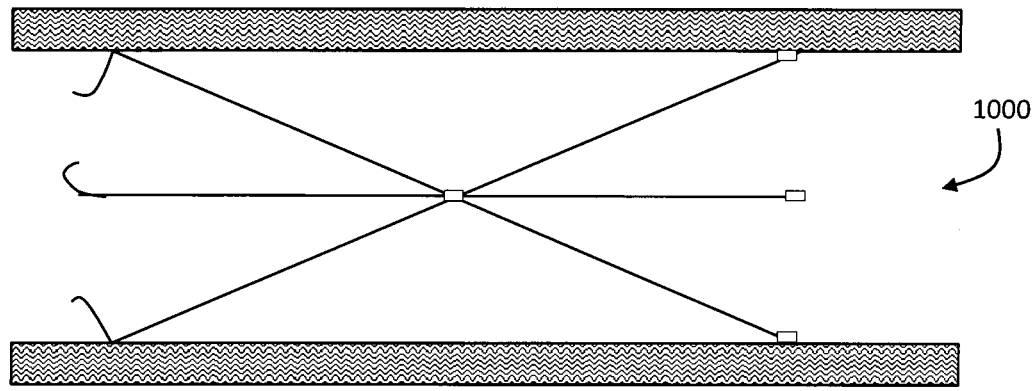
Figure 270:
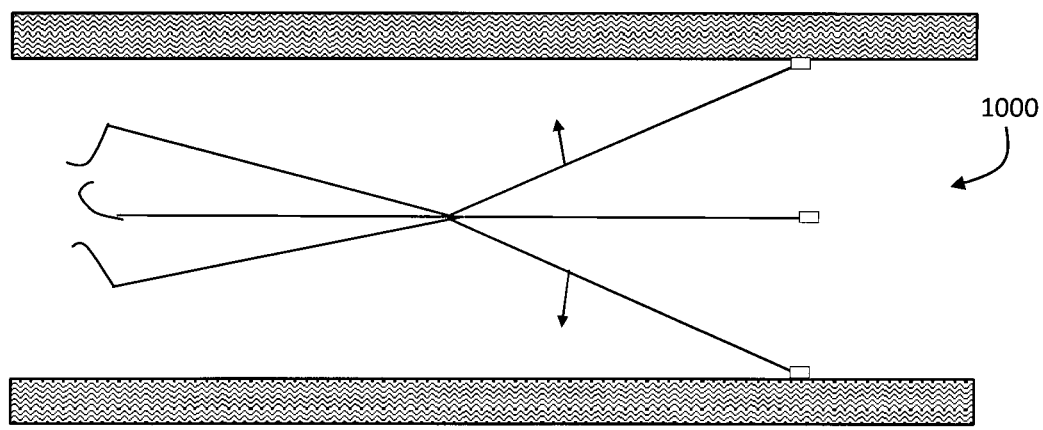
Figure 271:
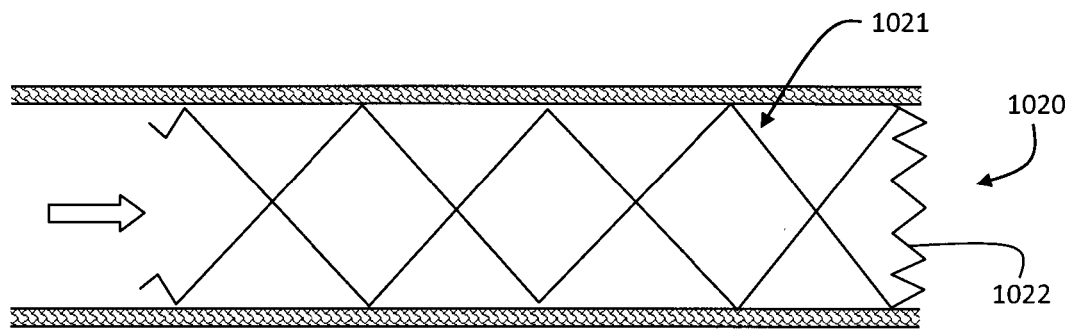
FIGS. 271 to 274 show a device with a filter having a scissors-type operation for breaking down a clot.
Figure 272:
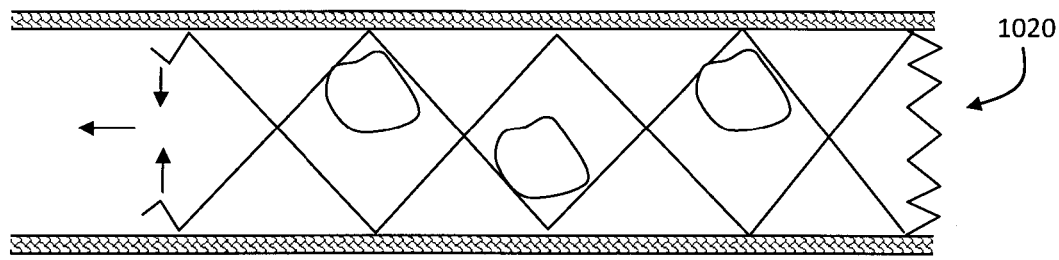
Figure 273:
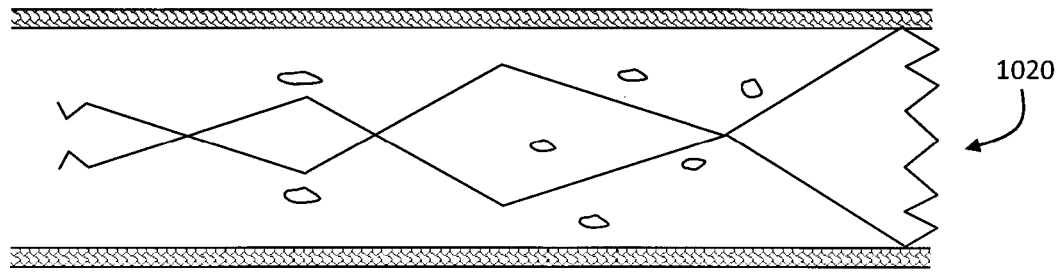
Figure 274:
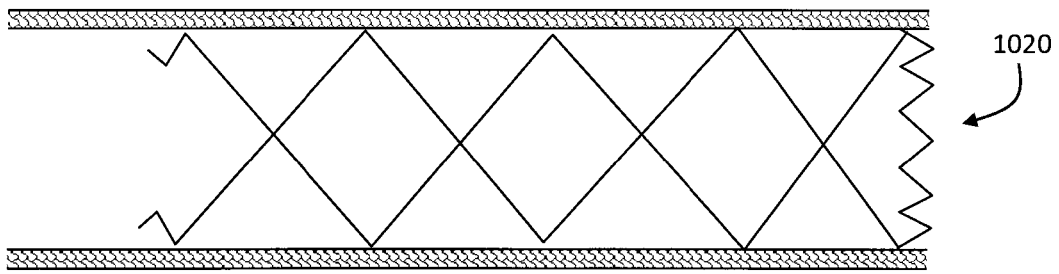

FIGS. 263 and 264

This is an axial view of a device 980 based on the principles described above. A support ring 981 supports V-shaped arms 982, in turn supporting retention features 983. A distal support ring may also be provided with longitudinal supports in between.

FIGS. 265 to 270

In a device 1000 a conical filter 1001 is provided with means 1003 to manually serrate a clot if present. A snare/lasso catheter is advanced to the proximal end where it catches proximal hooks 1003. When the snare/lasso is tightened, the proximal capture arms cut the clot into smaller pieces. The hooks may also be used to retrieve the device or alternatively the coupling member at the apex degrades and each capture arm returns to the vessel wall. A number of proximal and/or distal support rings may be provided. The holder 1002 degrades after a period of time allowing the filter to convert to an open state where blood flow is unobstructed.

FIGS. 271 to 274

In a device 1020 a scissors filter 1021 is provided with means to manually serrate a clot if present. A snare/lasso catheter is advanced to the proximal end where it catches the proximal hooks. When the snare/lasso is tightened, the proximal filter elements cut the clot into smaller pieces. When the tightened snare/lasso is pulled proximally, the scissors capture arm arrangement cuts the clot into even smaller pieces. The hooks may also be used to retrieve the device or alternatively, coupling members at the apex degrade and each capture arm returns to the vessel wall. It is appreciated that each cell of the scissors may have different orientations. This would provide more efficient filtration—for example, an end on view would illustrate the variable orientations of each closed cell whereas an end on view of FIGS. 271 to 274 would illustrate a single straight line extending across the centre of the vessel. A number of proximal and/or distal support rings may be provided.

FIGS. 275 to 283

In various embodiments, the filter element may be pre-formed or heat set to have an arc profile in the open state axial view in order not to obstruct the blood flow. Alternatively, the filter elements may be flexible so that they conform to the vessel wall in the open state in order not to obstruct the blood flow—this is advantageous over a pre-shaped profile as it will work in a wider range of vessel diameters. Preferably, the filter element has a steep angle to the degradable attachment—this allows the filter element to slide out of any endothelial growth with ease. Preferably, the filter element is attached to the support frame at an angle perpendicular to the plane of filter element movement during conversion. Filter elements may also be compressed or expanded to be shorter or longer in the closed state respectively. Upon conversion, the stored energy causes the filter element to return to an unconstrained state. Filter elements may also have a longitudinal curvature which provides a steeper angle to the degradable attachment—a filter element can be compressed in the closed state to have a longitudinal curve that reverts to a substantially longitudinally straight shape that is longer in the open state.

Figures 275, 276:
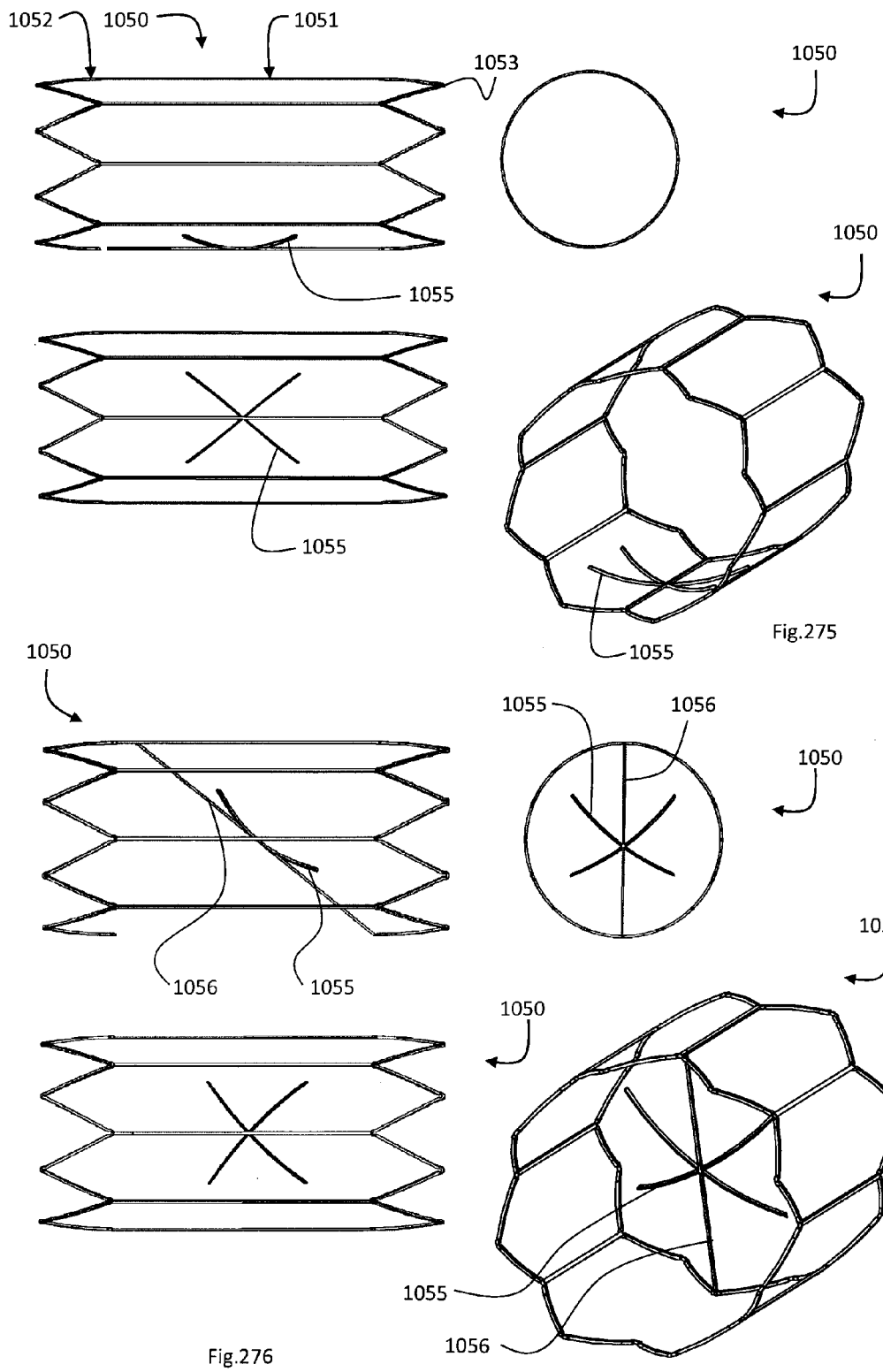
FIGS. 275 and 276 are various diagrams showing a device with a filter element which extends across the diameter of the support and is secured by a biodegradable coupling.
Figure 284:
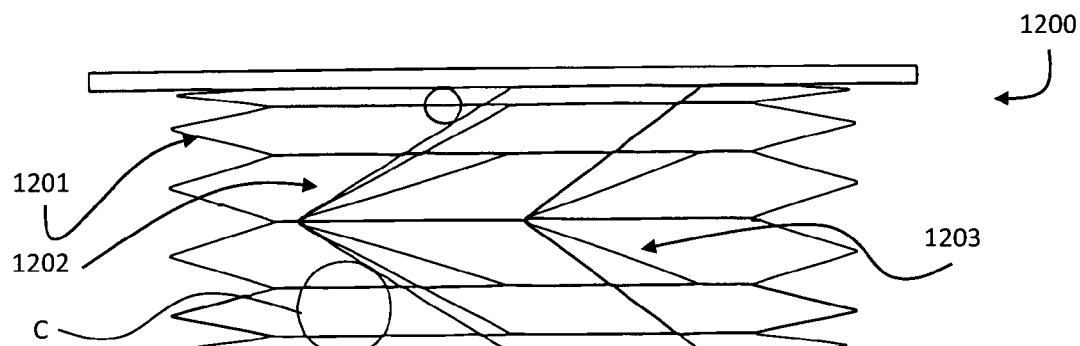
FIGS. 284 to 287 illustrate a further device of the invention, in this case having two reverse cone-shaped filters.
Figure 285:
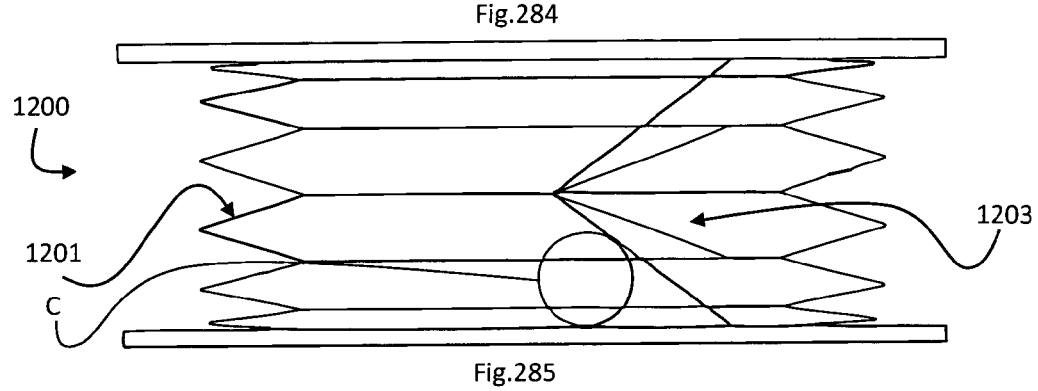
Figure 286:
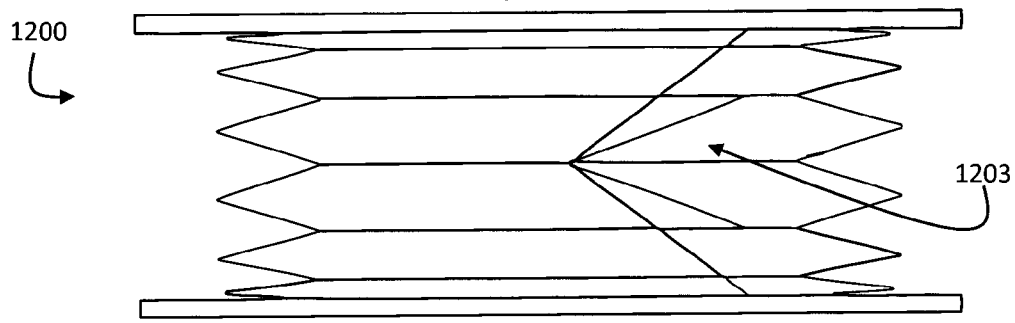
Figure 287:
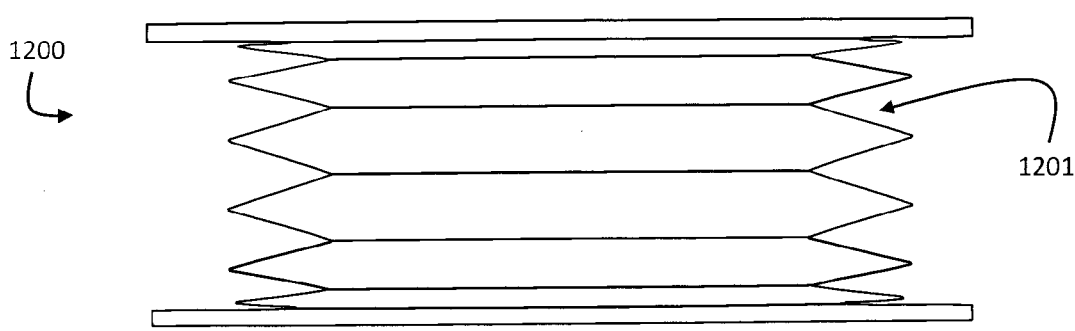
Figure 288:
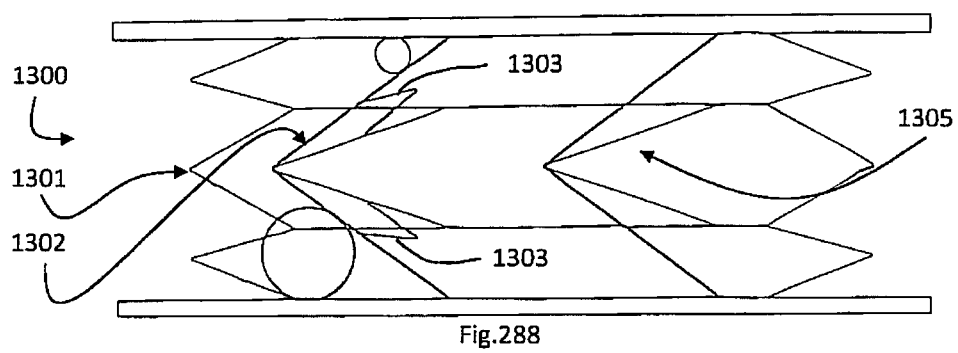
FIGS. 288 to 291 illustrate a still further filter device, also with two reverse cone-shaped filters.
Figure 289:
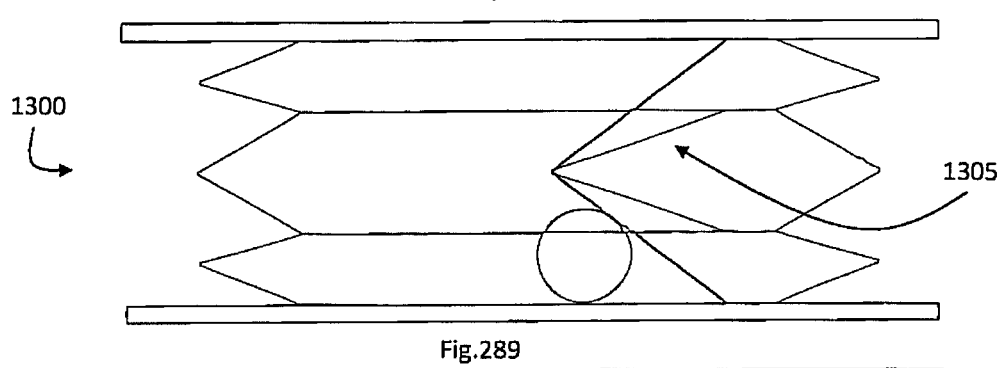
Figure 290:
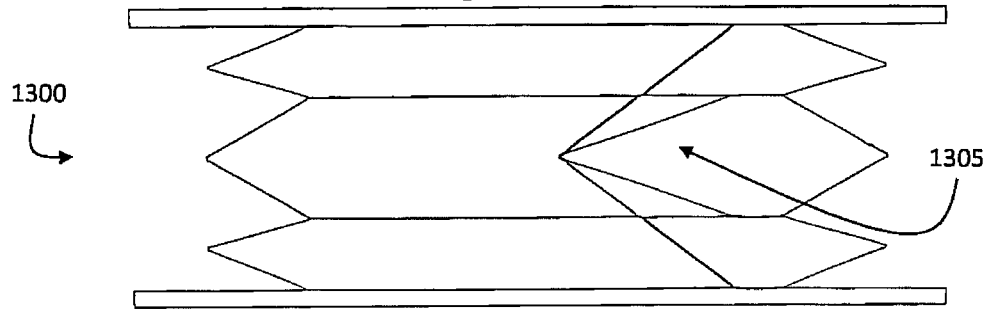
Figure 291:
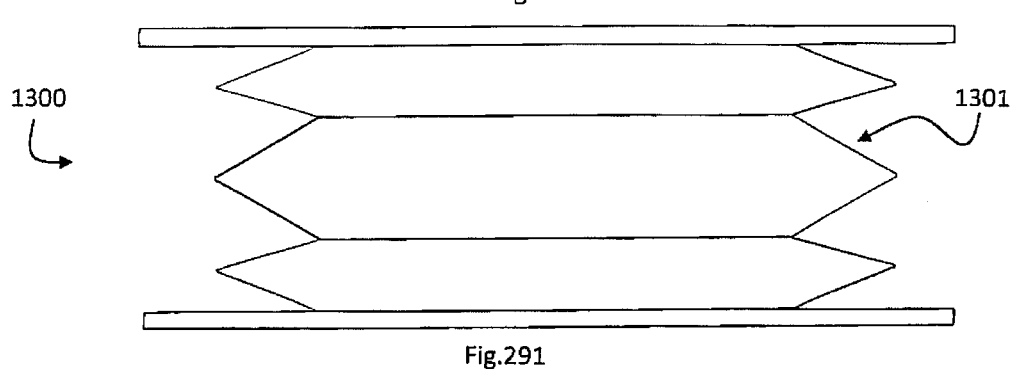
Figure 292:
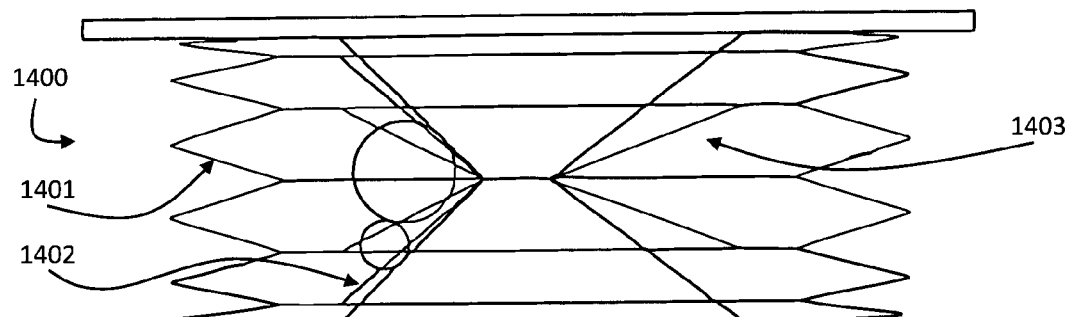
FIGS. 292 to 295 illustrate a further filter device, in this case with facing cone-shaped filters.
Figure 293:
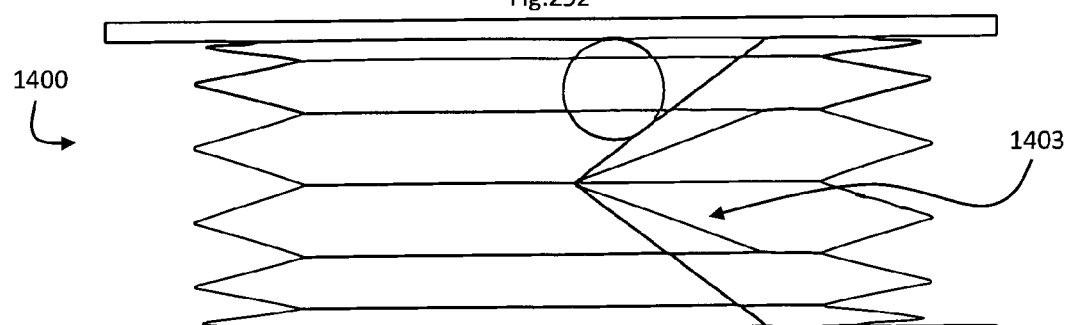
Figure 294:
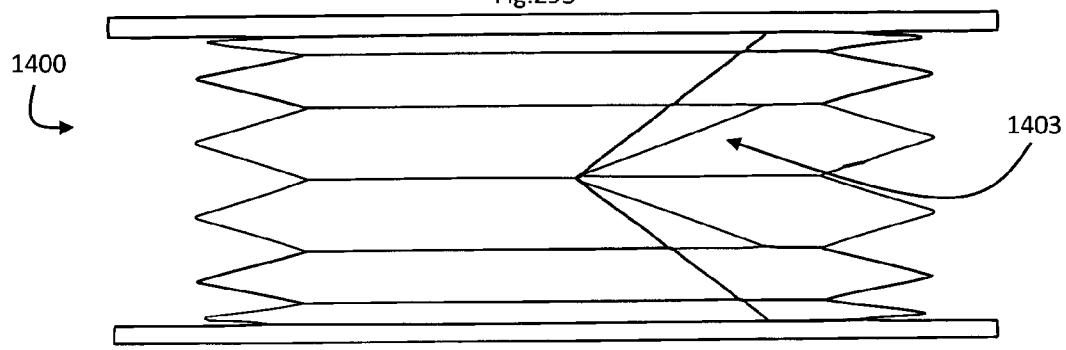
Figure 295:
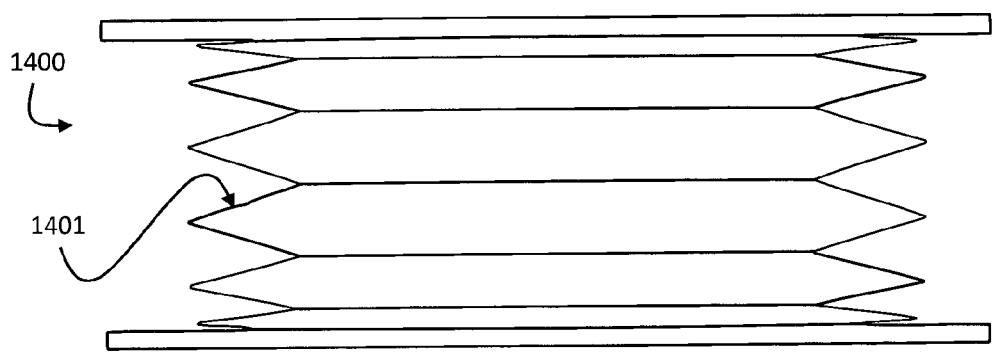
Figure 296:
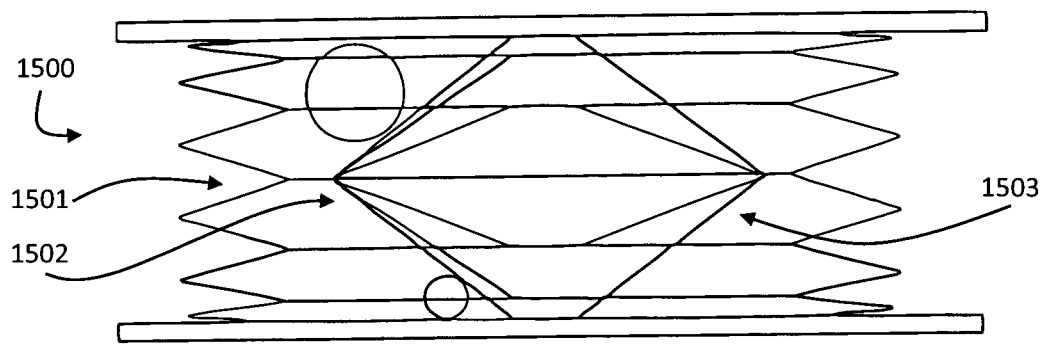
FIGS. 296 to 301 illustrate a further filter device, in this case with two cone-shaped filters the apexs of which face away from each other.
Figure 297:
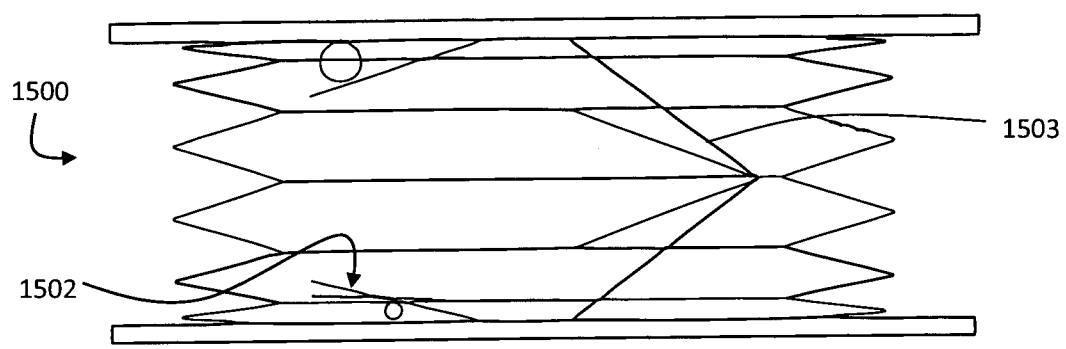
Figure 298:
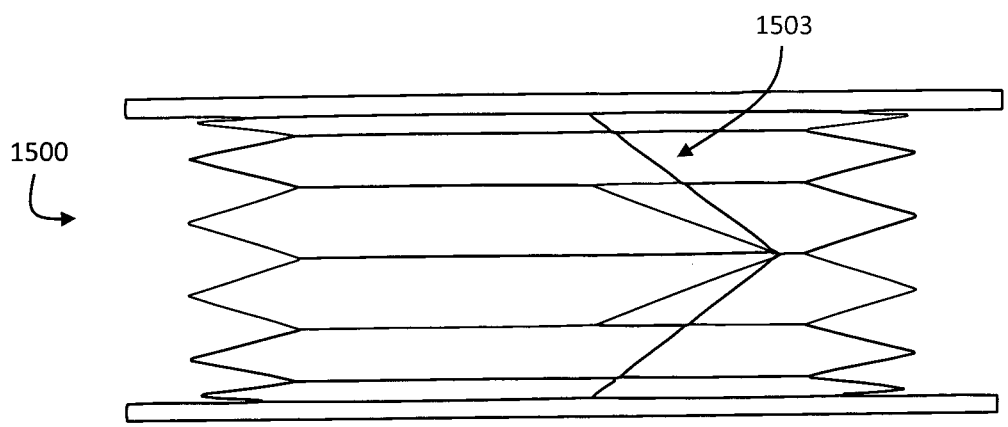
Figure 299:
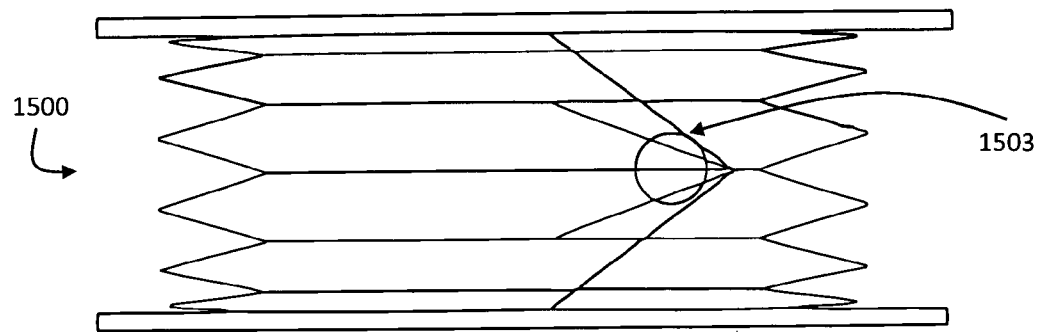
Figure 300:
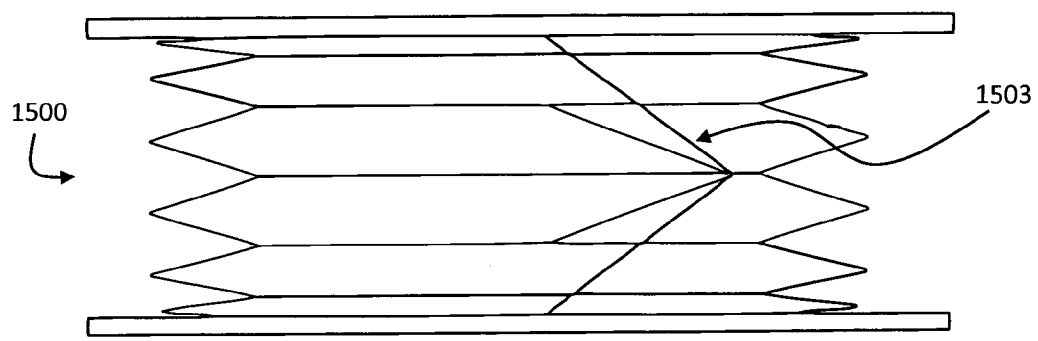
Figure 301:
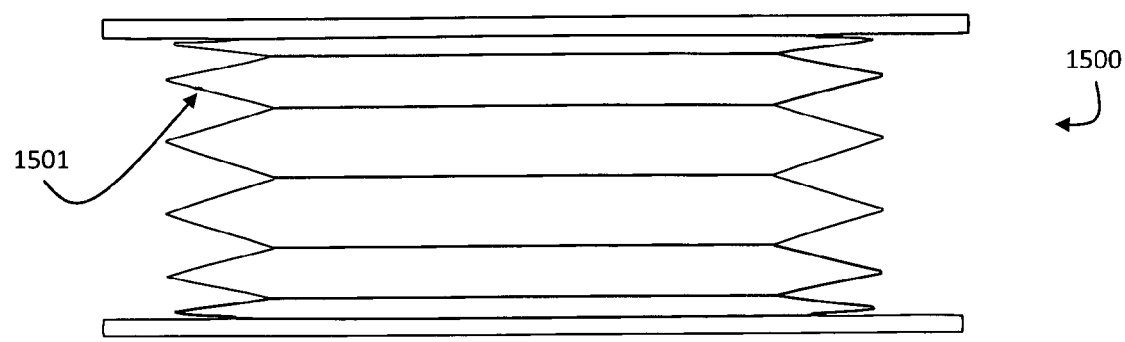

FIGS. 275 and 276 show a filter device 1050 with a proximal support hoop 1052, longitudinal struts 1051, and a distal support hoop 1053. A single filter element comprising a cross configuration 1055 on an arm 1056 extends across the diameter, connected to the support 1051 by a biodegradable coupling. In the closed state, FIG. 276, clots are directed to the vessel wall and upon conversion, the clot, if present, is compressed between the filter element and the vessel wall. Multiple cross configurations may be provided to enhance capture efficiency and clot retaining properties.

FIG. 277 shows a device 1100 with a proximal support hoop 1102, longitudinal struts 1101, and a distal support hoop 1103. A filter element comprises an arm 1105 extending across the support an angle and supporting loop 1106. A biodegradable coupling connects the arm 1105 to the support. FIGS. 278 and 279 show variations in which there are different numbers of loops held by the arm. There are four loops 1120 in the device of FIG. 278 and five loops 1130 in the device of FIG. 279. The arm is provided as loops in the device of FIG. 279.

FIG. 280 shows a device having a filter element arm 1151 supporting a loop 1152 and being connected to the support by a coupler 1153 at right angles to the support. This arrangement prevents endothelial growth from adversely affecting the biodegradable coupling.

FIG. 281 shows a device 1160 having a filter element 1161 which is stretched to be straight when closed, and is curved when slack so that it conforms better to the vessel side wall.

A flexible filter element unstretched will look the same as the device in FIG. 281, upon conversion, branches or loops will appear curved to conform the vessel wall as in FIG. 275.

FIGS. 282 and 283 show a device 1170 which has a filter element 1171 which is curved when closed, and straightens out when open. The filter element is fitted with flexible side branches 1172 that cannot be seen in the closed state, FIG. 282, as they extend in the same plane as the filter element 1171. FIG. 283 shows the open state where the filter element 1171 is lengthened out and straightened, the flexible side branches 1172 now being visible as they conform to the vessel wall. An axial view of the device would appear as a hollow cylinder where filter elements do not obstruct the blood flow.

FIGS. 284 to 287 (Double Reverse Cone-Shaped Filters)

In a device 1200 having a support 1201 a proximal cone-shaped filter 1202 has finer capture efficiency when compared to distal cone-shaped filter 1203. The proximal filter 1202 holder degrades first, providing protection for large and small clot particles for a first period of time.

Particles if present are retained after conversion at the vessel wall until lysis is complete. The distal cone-shaped filter 1203 degrades at a later stage and offers coarser filtration for a second period of time until conversion, and clots if present are trapped at the vessel wall until lysis is complete. Therefore in this embodiment there are two cycles of capture, conversion and retention. It is envisaged that a patient may require heightened capture efficiency in the early stages as pulmonary reserve may be compromised. After pulmonary reserve is restored, protection is only needed for large clots—this avoids potential for the distal filter 1203 to become blocked from excessive capture of small particles.

FIGS. 288 to 291 (Double Reverse Cone-Shaped Filters)

A device 1300 has a support 1301, a cone-shaped proximal filter 1302 with V-shaped members 1303 and a distal cone-shaped filter 1305. This operates much as the device 1200, but finer capture efficiency is provided by the V-shaped members 1303, which connect every second pair of filter elements in the proximal filter 1302.

FIGS. 292 to 295 (Double Facing Cone-Shaped Filters)

In a device 1400 there is a support 1401, a proximal cone-shaped filter 1402 with the apex facing distally, and a distal cone-shaped filter 1403 with the apex facing proximally. The proximal filter 1402 has finer capture efficiency when compared to the distal filter 1403. The proximal filter holder degrades first, providing protection for large and small particle for a first period of time. Particles if present are released to the distal filter 1403, smaller particles flowing through the distal filter 1403 but larger particles being trapped. The distal filter 1403 degrades at a later stage and offers coarser filtration for a second period of time until its conversion, and clots if present are retained at the vessel wall until lysis is complete. It is envisaged that a patient may require heightened capture efficiency in the early stages as pulmonary reserve may be compromised. After pulmonary reserve is restored, protection is only needed for larger clots—this avoids potential for the distal cone to become blocked from excessive capture of small particles.

FIGS. 296 to 301. (Double Opposing Cone-Shaped Filters)

A device 1500 has a support 1501, a cone-shaped proximal filter 1502 with to apex facing proximally, and a cone-shaped distal filter 1503 with the apex facing distally. The proximal filter 1502 has finer capture efficiency when compared to the distal filter 1503. The proximal filter holder degrades first, providing protection for large and small particle for a first period of time. Particles if present are retained at the vessel wall until lysis is complete. The distal filter 1503 degrades at a later stage and offers coarser filtration for a second period of time. It is envisaged that a patient may require heightened capture efficiency in the early stages as pulmonary reserve may be compromised. After pulmonary reserve is restored, protection is only needed for large clots—this avoids potential for the distal cone to become blocked from excessive capture of small particles.

It is thus appreciated that a filter of the invention may be provided with two stages of filtration as described above, or indeed more than two as further distal filters may be provided. Although it is preferred that a single filter in the device performs clot retention after conversion, it is possible that clot retention is achieved by presence of the second or subsequent distal filter which has a holder with later conversion.

It is appreciated that the double cone device may have the apices facing distally It is appreciated that a multistage filter may be provided with one or more completely degradable filter(s) and one or more convertible filter(s) with a holder(s)

It will be appreciated that the invention successfully addresses the problem of a clot being released into the blood stream after a filter opens. This provides an additional degree of confidence in use of a convertible filter instead of a permanent one.

Individual biodegradable restraints may be employed to allow each capture arm to convert at different points in time. This provides a cutting action.

Biodegradable membranes and tethers may be added to the capture arms to offer additional temporary support for clots trapped against the vessel wall.

Biodegradable capsules filled with anti-thrombogenic drugs/alternative treatment may be attached to the filter. The capsule may be programmed to release the drug before conversion, during conversion, or after conversion, preferably moments before conversion.

Upon conversion filter, there is a risk that a trapped clot that has not completed the lyses process may be released. In order to prevent the clot from being released, it can be retained by the filter post conversion until the clot has completed lysis. It is advantageous to retain the clot in the centre of the blood vessel where the higher flow rates offer optimal lysis time.

It is appreciated that any of the filters may be attached to a support frame consisting of proximal and distal support hoops with longitudinal support members connected in between. Proximal support hoops may have fewer or more peaks than the distal support and the longitudinal support may be straight or curved to provide space for filter elements in the open configuration. Alternatively; single, double, triple, or more support hoops may be supplied. Such support structures provide a stable platform with centred positioning from which the filters can operate.

Filter elements may extend from any point on the support frame. Filter elements that extend from longitudinal supports have optimal radial conversion force to aid in their return to the vessel wall; additional cross-sectional thickness may be supplied to the longitudinal supports and/or sections of the filtration elements local to their connection points to enhance this further. Where filter elements extend from peaks of the support hoops, additional cross-sectional thickness may be imparted to the support hoops, locally or entirely, and perhaps to a section of the filter elements local to their connection points to provide additional radial conversion force. Filter elements extending from two or more connection locations will have higher radial conversion forces than that with one connection location.

Higher radial conversion force aids in holding a clot, if present, against the wall and/or breaking it up. Apart from varying thickness and/or cross-section of the filter elements and support frame, this effect could also be applied by imparting an outwardly biased heat set on the filter elements in the open state.

Loop and cell filter embodiments may be provided with single, double, triple, quadruple, or more loops/cells. The loops or cells may be interlocked as described earlier to provide a centred conversion where the apex stays centred along the axis of the vessel during conversion. Loops or cells can be arranged axially so that the two smallest cells oppose each other, are equidistant, or, increase in size in a clockwise or anti-clockwise direction. Opposing and equidistant arrangements offer a balanced and reliable conversion.

Barbs may be supplied on the support frame to prevent axial translation during deployment and use.

Any of the embodiments may be fitted with a releasable biostable holder in the form of a pin, cap, ring, or tube. The biostable holder ideally has a hook that can be snared or a magnetic insert that can be grasped by a magnetic catheter to facilitate removal of the biostable holder. Preferably, a biostable pin is provided with flexible stops to prevent the eyelets from sliding off and a hook that can be grasped by a snare. The snaring catheter having a reception space so that the catheter is pressed against the filter elements as the pin is pulled inside—this stabilizes the pin removal force thus preventing damage to the vessel wall. The flexible bumps deform as they are pulled through the eyelets.

Stored energy may be imparted to the filter elements through bending or twisting and held in place with a releasable coupling. Release of the coupling then allowing the filter elements to actively break down clot if present.

An intervention may be performed to extend the protection period either temporarily or permanently. For example, a catheter would grasp a hook or feature near the holder and deliver a claw, c-tube, coil, or memory wire to prevent the filter elements from opening. The claw, c-tube, or coil moving from an expanded state on the delivery catheter to a biased collapsed state where it retains the filter elements in the closed state.

It is appreciated that the filter embodiments discussed above can be used for general embolic protection in any blood vessel.

The invention is not limited to the embodiments hereinbefore described, with reference to the accompanying drawings, which may be varied in construction and detail.

The invention claimed is:

1. A vascular filter device comprising:
   a central longitudinal axis;
   a support;
   a filter having an open state and a closed filtering state, wherein the support provides an outer circumference of an unrestricted open channel when the filter is in the open state, the filter further comprising
      a plurality of filter elements, each of the plurality of filter elements having a free end with a bend in the direction of movement of the respective filter element toward the open state, the free end being free in both the open state and the closed filtering state;
   a holder for holding the plurality of filter elements in the closed filtering state and for releasing the plurality of filter elements to convert the filter to the open state;
   wherein at least a portion of the plurality of filter elements are configured to capture thrombus centrally in the vessel; and
   wherein the plurality of filter elements are arranged to open towards the vessel wall for unrestricted blood flow in the absence of a thrombus, wherein each of the plurality of filter elements move first toward, and then away from the central longitudinal axis when converting from the closed filtering state to the open state.

2. The filter device of claim 1, wherein the plurality of filter elements form a double cone configuration in the closed filtering state.

3. The filter device of claim 1, wherein the holder is configured to passively release the plurality of filter elements to convert the filter toward the open state after a period of time.

* * * * *